US007098324B2

(12) United States Patent
Haigler et al.

(10) Patent No.: US 7,098,324 B2
(45) Date of Patent: Aug. 29, 2006

(54) CHITINASE ENCODING DNA MOLECULES FROM COTTON EXPRESSED PREFERENTIALLY IN SECONDARY WALLED CELLS DURING SECONDARY WALL DEPOSITION AND A CORRESPONDING PROMOTER

(75) Inventors: Candace H. Haigler, Lubbock, TX (US); Hong Zhang, Lubbock, TX (US); Chunfa Wu, Lubbock, TX (US); Chun-Hua Wan, Gaithersburg, MD (US); Deshui Zhang, Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 169 days.

(21) Appl. No.: 10/350,696

(22) Filed: Jan. 23, 2003

(65) Prior Publication Data

US 2004/0049808 A1 Mar. 11, 2004

Related U.S. Application Data

(63) Continuation-in-part of application No. 09/918,083, filed on Jul. 30, 2001, now abandoned.

(51) Int. Cl.
*C12N 15/29* (2006.01)
*C12N 15/82* (2006.01)

(52) U.S. Cl. ............... 536/24.1; 435/320.1; 800/287; 800/314

(58) Field of Classification Search ............. 536/24.1; 435/320.1, 419, 468; 800/287, 278, 298, 800/290, 314
See application file for complete search history.

(56) References Cited

U.S. PATENT DOCUMENTS

| | | | |
|---|---|---|---|
| 5,004,863 A | 4/1991 | Umbeck | |
| 5,474,925 A | 12/1995 | Maliyakal et al. | |
| 5,495,070 A * | 2/1996 | John | 800/287 |
| 5,521,078 A | 5/1996 | John | |
| 5,530,187 A | 6/1996 | Lamb et al. | |
| 5,597,718 A | 1/1997 | John et al. | |
| 5,620,882 A | 4/1997 | John | |
| 5,981,834 A | 11/1999 | John et al. | |
| 6,096,950 A | 8/2000 | John | |
| 6,169,174 B1 | 1/2001 | Hasegawa et al. | |
| 6,211,430 B1 | 4/2001 | John | |
| 6,225,536 B1 | 5/2001 | Kasukabe et al. | |
| 6,259,003 B1 | 7/2001 | Fujisawa et al. | |
| 6,329,570 B1 | 12/2001 | Martineau | |

FOREIGN PATENT DOCUMENTS

EP 0 834 566 A2 4/1996

OTHER PUBLICATIONS

Rinehart et al. Plant Physiol (1996) 112:1331-1341.*

Chlan et al., "Class I Chitinases in Cotton (*Gossypium hirsutum*): Characterization, Expression and Purification," *Plant Science* 161:143-154 (2001).
John et al., "Gene Expression in Cotton (*Gossypium hirsutum* L.) Fiber: Cloning of the mRNAs," *Proc. Natl. Acad. Sci. USA*, 89(13): 5769-5773 (1992).
John, "Characterization of a Cotton (*Gossypium hirsutum* L.) Fiber mRNA (Fb-B6)," *Plant Physiol.*, 107(4): 1477-1478 (1995).
Ma et al., "Differential Expression of a Lipid Transfer Protein Gene in Cotton Fiber," *Biochim. Biophysica Acta*, 1257(1): 81-84 (1995).
John et al., "Characterization of mRNA for a Proline-Rich Protein of Cotton Fiber," *Plant Physiol.*, 108(2): 669-676 (1995).
John et al., "Structural Characterization of Genes Corresponding to Cotton Fiber mRNA, E6: Reduced E6 Protein in Transgenic Plants by Antisense Gene," *Plant Mol. Biol.*, 30(2): 297-306 (1996).
Rinehart et al., "Tissue-Specific and Developmental Regulation of Cotton Gene FbL2A. Demonstration of Promoter Activity in Transgenic Plants," *Plant Physiol.*, 1 12(3): 1331-1341 (1996).
Orford et al., "Abundant mRN As Specific to the Developing Cotton Fibre," *Theor. Apl. Genet.*, 94:909-918 (1997).
Orford et al., "Characterization of a Cotton Gene Expressed Late in Fibre Cell Elongation," *Theor. Apl. Genet.*, 98: 757-764 (1999).
Orford et al., "Expression of a Lipid Transfer Protein Gene Family During Cotton Fibre Development," *Biochim. Biophysica Acta*, 1483(2): 275-284 (2000).
Ihara et al., "Cloning and Sequencing of Cotton Homologs of besA Gene Encoding Cellulose 4-β-glucosyltransferase," *Wood Res.* 84:1-6 (1997) (abstract).
Yamamoto, "Isolation and Characterization of cDNAs that are Preferentially Expressed in Cotton Fibre (*Gossypium hirsutum*)," Texas Tech Univ., Univ. Microfilms Int., DA 9522349, Diss. Abstr. Int. 56 (3), 1263 (1995) (abstract).
Pear et al., "Higher Plants Contain Homologs of the Bacterial celA Genes Encoding the Catalytic Subunit of Cellulose Synthase," Proc. Natl. Acad. Sci. USA 93:12637-12642 (1996).
Levorson et al., GenBank Accession No. Q39799 (Jul. 15, 1998).
Levorson et al., GenBank Accession No. Q39785 (Jul. 15, 1999).
Levorson et al., GenBank Accession No. AAD11255 (Feb. 1, 1999).
Hudspeth et al., GenBank Accession No. S72528 (Jun. 22, 1999).
Hamel et al., GenBank Accession No. Q09023 (Oct. 1, 1994).

(Continued)

*Primary Examiner*—David T. Fox
*Assistant Examiner*—Stuart F. Baum
(74) *Attorney, Agent, or Firm*—Nixon Peabody LLP

(57) ABSTRACT

The present invention relates to isolated nucleic acid molecules encoding endogenous cotton chitinases and corresponding promoters, which are preferentially expressed in secondary walled cells during secondary wall deposition. The polypeptide encoded by the nucleic acid molecule, a DNA construct linking the isolated nucleic acid molecule with a promoter, the DNA construct incorporated in an expression system, a host cell, a plant, or a plant seed are also disclosed. The present invention also relates to a DNA construct linking the isolated promoters with a second DNA as well as expression systems, host cells, plants, or plant seeds containing the DNA construct. Methods of imparting resistance to insects and fungi, regulating the fiber cellulose content, and methods of expressing a gene preferentially in secondary walled cells during secondary wall deposition are also disclosed.

2 Claims, 12 Drawing Sheets

OTHER PUBLICATIONS

Danhash et al., GenBank Accession No. Q05537 (Oct. 1, 1994).
Samac et al., GenBank Accession No. P19171 (Jul. 15, 1998).
Broglie et al., GenBank Accession No. P06215 (Oct. 1, 1994).
Broglie et al., GenBank Accession No. P36361 (Oct. 1, 1994).
Ohme-Takagi et al., GenBank Accession No. BAA33971 (Apr. 14, 2000).
Nishizawa et al., GenBank Accession No. S39979 (Jul. 10, 1998).
Chang et al., GenBank Accession No. P21226 (Jul. 15, 1999).
Kellman et al., GenBank Accession No. S65069 (Jun. 22, 1999).
Song et al., GenBank Accession No. 1310888 (Jun. 24, 1995).
Sato et al., GenBank Accession No. BAA94976 (Jul. 19, 2000).
Liu et al., GenBank Accession No. AAF29391 (Feb. 1, 2000).
Bishop et al., GenBank Accession No. AAF69789 (May 13, 2000).
Dubery et al., "Induced Defense Responses in Cotton Leaf Disks by Elicitors from *Verticillium dahliae*," Phytochemistry 44(8):1429-1434 (1997) (abstract).
Hudspeth et al., "Characterization and Expression of Chitinase and 1,3-beta-glucanase Genes in Cotton," Plant Mol. Biol. 31(4):911-916 (1996) (abstract).
Liu et al., "Detection of Pathogenesis-Related Proteins in Cotton Plants," Physiological and Molecular Plant Pathology 47(6):357-363 (1995) (abstract).
Hiilovaara-Teijo et al., "Snow-Mold-Induced Apoplastic Proteins in Winter Rye Leaves Lack Antifreeze Activity," Plant Physiology 121(2):665-673 (1999) (abstract).
Petruzzelli et al., "Distinct Ethylene- and Tissue-Specific Regulation of beta-1,3-glucanases and Chitinases During Pea Seed Germination," Planta. 209(2):195-201 (1999) (abstract).
Nishizawa et al., "Enhanced Resistance to Blast (*Magnaporthe grisea*) in Transgenic Japonica Rice by Constitutive Expression of Rice Chitinase," Theoretical and Applied Genetics 99(3/4):383-390 (1999) (abstract).
Vannini et al., "Antifungal Properties of Chitinases from *Castanea sativa* Against Hypovirulent and Virulent Strains of the Chestnut Blight Fungus *Cryphonectria parasitica*," Physiological and Molecular Plant Pathology 55(1):29-35 (1999) (abstract).
Bliffeld et al., "Genetic Engineering of Wheat for Increased Resistance to Powdery Mildew Disease," Theoretical and Applied Genetics 98 (6/7):1079-1086 (1999) (abstract).
Ancillo et al., "A Distinct Member of the Basic (Class I) Chitinase Gene Family in Potato is Specifically Expressed in Epidermal Cells," Plant Mol. Biol. 39(6):1137-1151 (1999) (abstract).
Yang et al., "A Pathogen- and Salicylic Acid-Induced WRKY DNA-Binding Activity Recognizes the Elicitor Response Element of the Tobacco Class I Chitinase Gene Promoter," The Plant Journal 18(2):141-149 (1999) (abstract).
Nishizawa et al., "Regulation of the Chitinase Gene Expression in Suspension-Cultured Rice Cells by n- Responsive Genes," acetylchitooligosaccharides: Differences in the Signal Transduction Pathways Leading to the Activation of Elicitor-Plant Mol. Biol. 39(5):907-914 (1999) (abstract).
Bushnell et al., "Genetic Engineering of Disease Resistance in Cereals," Canadian Journal of Plant Pathology 20(2):137-149 (1998) (abstract).
Hengel, "Expression Pattern of the Carrot EP3 Endochitinase Genes in Suspension Cultures and in Developing Seeds," Plant Physiol. 117(1):43-53 (1998) (abstract).
Egertsdotter et al., "Development of Somatic Embryos in Norway Spruce," Journal of Experimental Botany 49(319):155-162 (1998) (abstract).
Hamel et al., "Structural and Evolutionary Relationships Among Chitinases of Flowering Plants," Journal of Molecular Evolution 44(6):614-624 (1997) (abstract).
Dong et al., "Endochitinase and beta-1,3-glucanase Genes are Developmentally Regulated During Somatic Embryogenesis in *Picea glauca*," Planta. 201(2):189-194 (1997) (abstract).
Patil et al., "Possible Correlation Between Increased Vigour and Chitinase Activity Expression in Tobacco," Journal of Experimental Botany 48(316):1943-1950 (1997) (abstract).

Clendennen et al., "Differential Gene Expression in Ripening Banana Fruit," Plant Physiol. 115(2):463-469 (1997) (abstract).
Kragh et al., "Characterization of Chitinases Able to Rescue Somatic Embryos of the Temperature-Sensitive Carrot Variant ts11," Plant Mol. Biol. 31(3):631-645 (1996) (abstract).
Sahai et al., "Chitinases of Fungi and Plants: Their Involvement in Morphogenesis and Host-Parasite Interaction," FEMS Microbiology Reveiws 11(4):317-338 (1993) (abstract).
Punja et al., "Plant Chitinases and Their Roles in Resistance to Fungal Diseases," Journal of Nematology 25(4):526-540 (1993) (abstract).
Campillo et al., "Occurrence of 9.5 Cellulase and Other Hydrolases in Flower Reproductive Organs Undergoing Major Cell Wall Disruption," Plant Physiol. 99(3):1015-1020 (1992) (abstract).
Graham et al., "Cellular Coordination of Molecular Responses in Plant Defense," Molecular Plant-Microbe Interactions 4(5):415-422 (1991) (abstract).
Neale et al., "Chitinase, beta-1,3-glucanase, Osmotin, and Extensin are Expressed in Tobacco Explants During Flower Formation," The Plant Cell 2(7):673-684 (1990) (abstract).
Blee et al., "Proteomic Analysis Reveals a Novel Set of Cell Wall Proteins in a Transformed Tobacco Cell Culture that Synthesises Secondary Walls as Determinded by Biochemical and Morphological Parameters," *Planta*, 212:404-415 (2001).
Jefferson, *Plant Molecular Biology Reporter*, 5(4):387-405 (1987).
Kagaya et al., *Mol. Gen. Genet.*, 248:668-674 (1995).
Benfey et al., *Science*, 250:959-966 (1990).
Benfey et al., *EMBO J.*, 8(8):2195-2202 (1989).
Busch et al., *Science*, 285:585-587 (1999).
Lohmann et al., *Cell*, 105:793-803 (2001).
Oommenn et al., *The Plant Cell*, 6:1789-1803 (1994).
Hu et al., *Nature Biotechnology*, 17:808-812 (1999).
Kajita et al., *Plant Science*, 128:109-118 (1997).
Piquemal et al., *Plant Journal*, 13(1):71-83 (1998).
Sasaki et al., GenBank Accession No. BAC55635 (Jan. 22, 2003).
Zhong et al., "Mutation of a Chitinase-Like Gene Causes Ectopic Deposition of Lignin, Aberrant Cell Shapes, and Overproduction of Ethylene," *Plant Cell*, 14(1):165-179 (2002).
Zhang et al., "Molecular Cloning, Differential Expression, and Functional Characterization of a Family of Class I Ubiquitin-Conjugating Enzyme (E2) Genes in Cotton (*Gossypium*)," *Biochim. Biophys. Acta*, 1625(3):269-279 (2003).
Cedroni et al., "Evolution and Expression of *MYB* Genes in Diploid and Polyploid Cotton," *Plant. Mol. Biol.*, 51(3):313-325 (2003).
Li et al., "Molecular Characterization of the Cotton *GhTUBI* Gene That is Preferentially Expressed in Fiber," *Plant.Physiol.*, 130(2):666-674 (2002).
Sunilkumar et al., "Cotton α-Globulin Promoter: Isolation and Functional Characterization in Transgenic Cotton, *Arabidopsis*, and Tobacco," *Transgenic Res.*, 11(4):347-359 (2002).
Xiao et al., "Cloning and Characterization of a LRR Resistance Like (*GhLRR-RL*) Protein Gene from Cotton (*Gossypium hirsutum* L.)," *Acta Genetica Sinica.*, 29(7):653-658 (2002).
Zhao et al., "Isolation of a Cotton RGP Gene: A Homolog of Reversibly Glycosylated Polypeptide Highly Expressed During Fiber Development," *Biochim. Biophys. Acta*, 1574(3):370-374 (2001).
Luo et al., "Cloning and Characterization of *D-113* Gene Promoter from Cotton," *Acta Genetica Sinica*, 29(2):161-165 (2002).
Tan et al., "Cloning and Expression Analysis of Two Cotton (*Gossypium hirsutum* L.) Genes Encoding Cell Wall Proline-Rich Proteins," *DNA Seq.*, 12(5-6):367-380 (2001).
Cui et al., "A Putative Plant Homolog of the Yeast β-1,3-Glucan Synthase Subunit *FKSI* From Cotton (*Gossypium hirsutum* L.) Fibers," *Planta*, 213(2):223-230 (2001).

\* cited by examiner

*FIG. 10a*
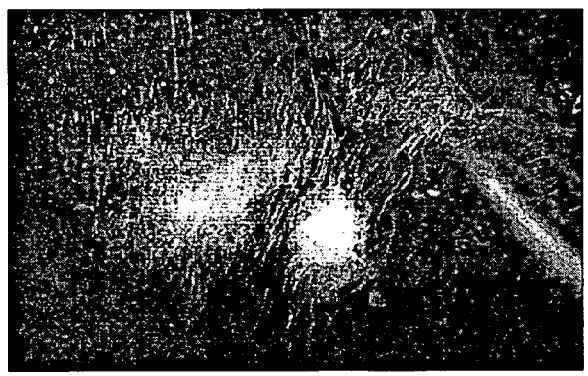
*FIG. 10b*
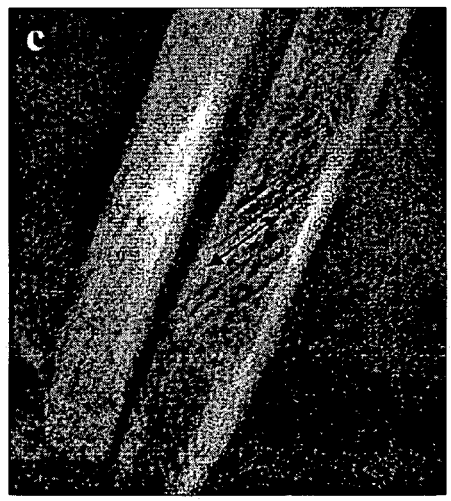 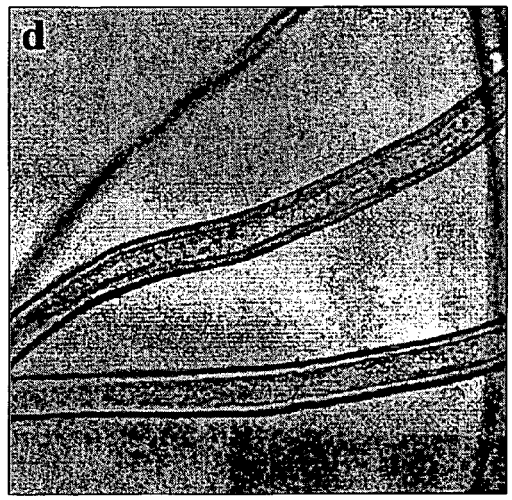
*FIG. 10c*  *FIG. 10d*

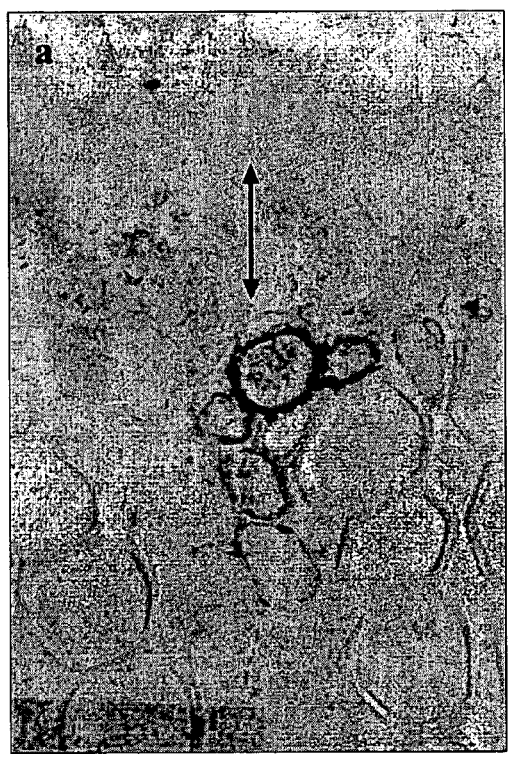 
FIG. 11a  FIG. 11b

CHITINASE ENCODING DNA MOLECULES FROM COTTON EXPRESSED PREFERENTIALLY IN SECONDARY WALLED CELLS DURING SECONDARY WALL DEPOSITION AND A CORRESPONDING PROMOTER

This is a continuation-in-part of U.S. patent application Ser. No. 09/918,083, filed Jul. 30, 2001, now abandoned, which is hereby incorporated by reference in its entirety.

FIELD OF THE INVENTION

The present invention relates to a gene that is expressed in secondary walled cells during secondary cell wall deposition and the promoter of the corresponding gene.

BACKGROUND OF THE INVENTION

Fiber cells of cotton (*Gossypium hirsutum* L. and other *Gossypium* species including *G. barbadense* L., *G. arboreum* L., and *G. herbaceous* L.), a crop of enormous economic importance to world-wide agriculture, are differentiated epidermal cells of the seed coat. At maturity, the fiber cell, considered from inside to outside, consists of a cell lumen, secondary cell wall, primary cell wall, and thin waxy cuticle. The primary cell wall is made up of pectic compounds, hemicellulose components, cellulose, and protein. The secondary cell wall consists mainly (about 95%) of cellulose with small percentages of other components not yet conclusively identified.

Cotton fiber development is characterized by the stages of initiation, primary cell wall deposition, secondary cell wall deposition, and dessication. During the primary wall stage of fiber development, primary wall deposition occurs to facilitate fiber elongation. During the secondary wall stage of fiber development, secondary wall deposition occurs to accomplish fiber thickening. Primary and secondary wall deposition involve the synthesis of all the cell wall components characteristic of each stage and the assembly of the molecules into an organized cell wall outside the plasma membrane. Many hundred of genes are required for the differentiation and development of plant fiber. Work on in vitro translated fiber proteins (Delmer et al., "New Approaches to the Study of Cellulose Biosynthesis," *J. Cell Sci. Suppl.*, 2:33–50 (1985)), protein isolated from fiber (Graves and Stewart, "Analysis of the Protein Constituency of Developing Cotton Fibers," *J. Exp. Bot.*, 39:59–69 (1988)), and analysis of particular genes (Wilkins et al., "Molecular Genetics of Developing Cotton Fibers," in Basra, ed., *Cotton Fibers: Developmental Biology, Quality Improvement, and Textile Processing*, Haworth Press:New York, p. 231–270 (1999)) clearly suggests differential gene expression during various developmental stages of the cell. However, only a few of the genes involved in the biosynthesis of the large numbers of fiber-specific or fiber-enhanced structural proteins, enzymes, polysaccharides, or waxes have been identified (John et al., "Gene Expression in Cotton (*Gossypium hirsutum* L.) Fiber: Cloning of the mRNAs," *Proc. Natl. Acad. Sci. USA*, 89:5769–5773 (1992); John, "Characterization of a Cotton (*Gossypium hirsutum* L.) Fiber mRNA (Fb-B6)," *Plant Physiol.*, 107: 1477–1478 (1995)). Since these genes and their interactions with environment determine the quality of fiber, their identification and characterization is considered to be an important aspect of cotton crop improvement.

In particular, how secondary cell walls are synthesized, how they aid plant function, adaptation, and defense, and how their properties translate into industrial utility are important questions related to basic biological mechanisms, ecology, and plant improvement. Plant secondary cell walls are synthesized in some specialized cell types to facilitate particular functions, such as long-range conduction of water (tracheary elements), control of transpiration (guard cells), and dispersal of seeds (cotton fibers). These secondary cell walls have a higher content of high tensile strength cellulose, usually exceeding 40% by weight, and are much thicker than primary cell walls. Consequently, their hemicellulose, pectin, and protein content is reduced, with the most extreme reduction occurring in the case of cotton fiber secondary cell walls which are about 95% cellulose. On the other hand, during primary wall deposition, the cellulose content is typically 9–30% (w/w) (Meinert et al., "Changes in Biochemical Composition of the Cell Wall of the Cotton Fiber During Development," *Plant Physiol.*, 59:1088–1097 (1977); Darvill et al., "The Primary Cell Walls of Flowering Plants," *The Biochemistry of Plants*, 1:91–162 (1980); Smook, *Handbook for Pulp and Paper Technologists*, Vancouver, Canada:Angus Wilde Publications, p. 15 (1992)). Because secondary cell walls are strong and represent a bulk source of chemical cellulose, they have been exploited as important renewable resources, for example in wood and cotton fibers.

Cotton fiber cells have two distinct developmental stages that include secondary wall deposition. Many studies of fiber length and weight increase, morphology, cell wall composition, cellulose synthesis rates, and gene expression have confirmed the summary of the stages of fiber development presented below, and recent reviews contain many primary references to confirm these facts (Delmer, "Cellulose Biosynthesis in Developing Cotton Fibers," in Basra, ed., *Cotton Fibers: Developmental Biology, Quality Improvement, and Textile Processing*," New York, N.Y.: Haworth Press, pp. 85–112 (1999); Ryser, "Cotton Fiber Initiation and Histodifferentiation," in Basra ed., *Cotton Fibers: Developmental Biology, Quality Improvement, and Textile Processing*," New York, N.Y.:Haworth Press, pp. 1–46 (1999); Wilkins et al., "Molecular Genetics of Developing Cotton Fibers, in Basra, ed., *Cotton Fibers: Developmental Biology, Quality Improvement, and Textile Processing*," New York, N.Y.:Haworth Press, pp. 231–270 (1999)). Following fiber initiation by bulging of an epidermal cell above the surface, fiber elongation begins. Primary wall deposition is required to facilitate fiber elongation, and primary wall deposition continues alone for at least 12 days after fiber initiation. This period represents exclusively the primary wall stage of fiber development. Then, secondary wall deposition begins while primary wall deposition continues, albeit usually at a slower rate. This stage of fiber development represents the transition between primary and secondary wall deposition, and it typically begins in *G. hirsutum* L. between 14–17 days post anthesis (DPA). Subsequently, fiber elongation and primary wall deposition cease, typically between 18–24 DPA, and secondary wall deposition persists exclusively until 34–50 DPA. Variation in the time of initiation and duration of each phase of fiber development depends on the cotton cultivar and the temperature conditions (DeLanghe, "Lint Development" in Mauney, eds., *Cotton Physiology*, pp. 325–349, The Cotton Foundation, Memphis, Tennessee (1986); Haigler et al., "Cultured Cotton Ovules as Models for Cotton Fiber Development Under Low Temperatures," *Plant Physiol.*, 95:88–96 (1991); Thaker et al., "Genotypic Variation and Influence of Diurnal Temperature on Cotton Fiber Development," *Field Crops Research*, 22:129–141 (1989)). For example, in field-grown *G. barbadense* L., extensive secondary wall deposition did not occur until after 20 DPA, elongation continued until 39 DPA, and secondary wall deposition ceased at 48 DPA (Schubert et al., "Growth and Development of the Lint Fibers of Pima S-4 Cotton," *Crop Sci.*, 16:539–543 (1976)).

The rates of cellulose synthesis change from low, to medium, to high, respectively, at the primary wall, transition, and secondary wall stages of fiber development (Meinert et al., "Changes in Biochemical Composition of the Cell Wall of the Cotton Fiber During Development," *Plant Physiol.*, 59:1088–1097 (1977); Martin, "Cool-Temperature-Induced Changes in Metabolism Related to Cellulose Synthesis in Cotton Fibers, Ph.D. dissertation, Texas Tech University, Lubbock, Tex., U.S.A. (1999)). An example is found in fibers developing on cultured cotton ovules at an optimum temperature of constant 34° C., which maximizes the rate of progression through the stages of fiber development. Combining results from fibers on ovules of two cotton cultivars of *G. hirsutum* L. cultured under this condition, primary wall deposition along with a low rate of cellulose synthesis occurs until 12–14 DPA, the transition between primary and secondary wall deposition and an intermediate rate of cellulose synthesis begins at 14–16 DPA, and secondary wall deposition continues along with a high rate of cellulose synthesis beginning at 16–21 DPA (Martin, "Cool-Temperature-Induced Changes in Metabolism Related to Cellulose Synthesis in Cotton Fibers, Ph.D. dissertation, Texas Tech University, Lubbock, Tex. U.S.A. (1999)). Other biochemical features demonstrate that the initiation of secondary wall deposition via an intermediate rate of cellulose synthesis at the transition stage marks a distinct developmental event: the cellulose content of new wall material rises sharply so that the overall percentage of cellulose in the whole fiber wall doubles in one day (Meinert et al., "Changes in Biochemical Composition of the Cell Wall of the Cotton Fiber During Development," *Plant Physiol.*, 59:1088–1097 (1977)), the respiration rate transiently declines, and the intercellular pools in the fiber of UDP-glucose and glucose-6-P begin to rise (Martin, "Cool-Temperature-Induced Changes in Metabolism Related to Cellulose Synthesis in Cotton Fibers, Ph.D. dissertation, Texas Tech University, Lubbock, Tex. U.S.A. (1999)). These are signs of an abrupt onset of secondary wall deposition (DeLanghe, "Lint Development" in Mauney, eds., *Cotton Physiology*, pp. 325–349, The Cotton Foundation, Memphis, Tenn. (1986)).

Primary and secondary wall deposition appear to be controlled by different genetic factors (Kohel et al., "Fiber Elongation and Dry Weight Changes in Mutant Lines of Cotton," *Crop Sci.*, 14:471–474 (1974)), and both stages can likely be manipulated independently by genetic engineering to achieve the longer, stronger, finer (smaller diameter), and more mature (as related to the secondary wall thickness) fiber that the textile industry desires. However, this goal can only be achieved by knowing more about the genes that control and contribute to each stage of fiber development.

After the fibers mature, the protective boll opens and the dried fiber often hangs for several weeks on the plant until the whole crop matures (unless stopped by killing cold temperatures) and vegetative growth dies or is killed chemically to allow harvest. During this period, fibers are subject to degradation by enzymatic activity of fungi, which is often enhanced by wet fall weather (Simpson et al., "The Geographical Distribution of Certain Pre-Harvest Microbial Infections of Cotton Fiber in the U.S. Cotton Belt," *Plant Disease Reporter*, 55:714–718 (1971)). In some years, this field-waiting time causes substantial deterioration of the grade of the fiber so that the producer receives a discounted price and the production of quality yarns and fabrics is jeopardized. Therefore, cotton production efficiency will be improved by more knowledge of how to bring the fibers undamaged from the field to textile plant. Relevant to achieving this goal is a better understanding of endogenous protections against fungal degradation that could be introduced or enhanced in the fiber.

Particularly because of their defensive role in plants (Gooday, "Aggressive and Defensive Roles for Chitinases," in Jolles, eds., *Chitin and Chitinases*, Birkhäuser Verlag: Basel, pp. 157–170 (1999)), numerous chitinase genes and proteins have been characterized in diverse plant species. The chitinase gene and protein family has been the subject of many reviews (including Graham et al., "Cellular Coordination of Molecular Responses in Plant Defense," *Molecular Plant-Microbe Interactions: MPMI*, 4:415–422 (1991); Cutt et al., "Pathogenesis-Related Proteins," in Boller, eds., *Genes Involved in Plant Defense*, Springer Verlag/N.Y. pp. 209–243 (1992); Meins et al., "The Primary Structure of Plant Pathogenesis-Related Glucanohydrolases and Their Genes," in Boller, eds., *Genes Involved in Plant Defense*, Springer Verlag/N.Y., p. 245–282 (1992); Collinge et al., "Plant Chitinases," *Plant J.*, 3:31–40 (1993); Sahai et al., "Chitinases of Fungi and Plants: Their Involvement in Morphogenesis and Host-Parasite Interaction," *FEMS Microbiology Rev.*, 11:317–338 (1993); Meins et al., "Plant Chitinase Genes," *Plant Molecular Biology Reporter*, 12:522–528 (1994); Hamel et al., "Structural and Evolutionary Relationships Among Chitinases of Flowering Plants," *Journal of Molecular Evolution*, 44:614–624 (1997)) and of an edited book (Jolles, eds. *Chitin and Chitinases*, Birkäuser Verlag:Basel, 340 pp (1999)). These sources contain many primary references to the well known facts summarized below. Chitinases are among a group of genes that are inducible in plants by pathogen attack, corresponding to the frequent occurrence of chitin in fungal cell walls and insect exoskeletons. In their defensive role, chitinases catalyze the hydrolysis of chitin. Structural chitin occurs as crystalline microfibrils composed of a linear homopolymer of $\beta$-1,4-linked N-acetyl-D-glucosamine residues, $(GlcNAc)_n$. Chitin hydrolysis defends the plant against predators or pathogens, particularly invading fungi, by weakening or dissolving their body structure. Especially in combination with $\beta$-1,3-glucanases that serve to uncoat the chitin microfibrils, chitinases can inhibit the growth of many fungi by causing hyphal tip lysis due to a weakened hyphal wall. This has been shown by inhibition of fungal growth in cultures as well as in transgenic plants that exhibit reduced pathogen damage in correlation with increased chitinase activity. Gene expression or activity of chitinases with a probable defensive function have previously been characterized in cotton leaves and roots (Liu et al., "Detection of Pathogenesis-Related Proteins in Cotton Plants," *Physiological and Molecular Plant Pathology*, 47:357–363 (1995); Hudspeth et al., "Characterization and Expression of Chitinase and 1,3-$\beta$-Glucanase Genes in Cotton," *Plant Molecular Biology*, 31:911–916 (1996); Dubery et al., "Induced Defence Responses in Cotton Leaf Disks by Elicitors From *Verticillium dahliae*," *Phytochemistry*, 44: 1429–1434 (1997)).

Some chitinases are induced upon fungal invasion, accumulating around invading fungal hyphae (Benhamou et al., "Subcellular Localization of Chitinase and Its Potential Substrate in Tomato Root Tissues Infected With *Fusarium*

Oxysporium F.Sp. Radicislycopersici," Plant Physiology, 92:1108–1120 (1990); Wubben et al., "Subcellular Localization of Plant Chitinases and 1,3-β-Glucanases in Cladosporium Fulvum (Syn. Fulvia Fulva)-Infected Tomato Leaves," Physiological and Molecular Plant Pathology 41:23–32 (1992)). Other chitinases apparently occur constitutively in plant parts that are particularly susceptible to invasion such as epidermal cells, root cortical cells, stomates, flower parts, and vascular cells. These conclusions arise from both localization of chitinase mRNA by in situ hybridization and analysis of patterns of expression of the GUS reporter gene under control of chitinase promoters (Samac et al., "Developmental and Pathogen-Induced Activation of the Arabidopsis Acidic Chitinase Promoter," The Plant Cell, 3:1063–1072 (1991); Zhu et al., "Stress Induction and Developmental Regulation of a Rice Chitinase Promoter in Transgenic Tobacco," The Plant Journal, 3:203–212 (1993); Büchter et al., "Primary Structure and Expression of Acidic (Class II) Chitinase in Potato," Plant Molecular Biology, 35:749–761 (1997); Ancillo et al., "A Distinct Member of the Basic (Class I) Chitinase Gene Family in Potato is Specifically Expressed in Epidermal Cells,". Plant Molecular Biology, 39:1137–1151 (1999)). In another case of possible anticipation of fungal invasion in disrupted tissues, ethylene induces chitinase in bean abscission zones (del Campillo et al., "Identification and Kinetics of Accumulation of Proteins Induced by Ethylene in Bean Abscission Zones," Plant Physiology, 98:955–961 (1991)). None of these studies included analysis of cotton fibers or showed the presence of chitinase activity or chitinase-related proteins in cotton fibers.

Other studies show that some chitinases have a developmental role in plants, although authentic structural chitin is not a natural part of the plant body (Meins et al., "The Primary Structure of Plant Pathogenesis-Related Glucanohydrolases and Their Genes," In Boller, eds., Genes Involved in Plant Defense, Springer Verlag/N.Y., p. 245–282 (1992)). It has been shown that chitinase isoforms with developmental roles are at least sometimes distinct from those with roles in stress responses and defense (Mauch et al., "Antifungal Hydrolases in Pea Tissue. I. Purification and Characterization of Two Chitinases and Two β-1,3-Glucanases Differentially Regulated During Development and in Response to Fungal Infection," Plant Physiology, 87:325–333 (1988)). Defensive chitinases bind to short stretches (probably 3–6 residues) of a single N-acetyl-glucosamine chain prior to cleaving the inter-sugar bond (Robertus et al., "The Structure and Action of Chitinases," in Jolles, eds., Chitin and Chitinases, Birkäuser Verlag:Basel, pp. 125–136 (1999)). Therefore, enzymes in the chitinase family can also bind to oligomers of N-acetyl-glucosamine within other molecules such as glycoproteins or signalling molecules. Such molecules may have roles in signal transduction to regulate gene expression cascades required for developmental transitions or in the biosynthetic processes that implement the developmental program.

Previous research on the regulation of secondary wall deposition or function at the molecular level focused on a few genes involved in cellulose, hemicellulose, lignin, or protein biosynthesis. Among these pathways, lignin synthesis has been most fully explored and manipulated in transgenic plants (Merkle et al., "Forest Biotechnology," Current Opinion in Biotechnology, 11:298–302 (2000)). However, cotton fibers contain no lignin (Haigler, "The Functions and Biogenesis of Native Cellulose," in Zeronian, eds., Cellulose Chemistry and Its Applications, Ellis Horwood:Chichester, England, pp. 30–83 (1985)). Hemicellulose polysaccharides within some secondary walls include xylans and glucomannans, but cotton fiber secondary walls do not contain significant quantities of any similar molecule (Haigler, "The Functions and Biogenesis of Native Cellulose," in Zeronian, eds., Cellulose Chemistry and Its Applications, Ellis Horwood:Chichester, England, pp. 30–83 (1985)). Only two proteins with possible structural roles in the cotton fiber secondary wall have been identified. One of these, H6, is an arabinogalactan-type protein that accumulates to detectable levels during secondary wall deposition, although the expression of its gene begins during rapid elongation including primary wall deposition (John et al., "Characterization of mRNA for a Proline-Rich Protein of Cotton Fiber," Plant Physiology, 108:669–676 (1995)). The second, FbL2A, lacks homology to any known protein, but its highly repetitive sequence and high hydrophilicity suggest that it may have a structural role or protect cotton fibers during dessication. The expression of its gene begins weakly at the primary to secondary wall transition (15 DPA) and is stronger by 20 DPA (Rinehart et al., "Tissue-Specific and Developmental Regulation of Cotton Gene FbL2A," Plant Physiology, 112:1331–1341 (1996)).

Enzymes that increase in gene expression and/or activity during cotton fiber secondary wall deposition and that relate to the regulation of cellulose synthesis include cellulose synthase, sucrose synthase, sucrose phosphate synthase, and UDP-glucose pyrophosphorylase (Basra et al., "Sucrose Hydrolysis in Relation to Development of Cotton (Gossypium spp.) Fibres," Indian Journal of Experimental Botany, 28:985–988 (1990); Wäfler et al., "Enzyme Activities in Developing Cotton Fibres," Plant Physiology and Biochemistry, 32:697–702 (1994); Amor et al., "A Membrane-Associated Form of Sucrose Synthase and its Potential Role in Synthesis of Cellulose and Callose in Plants," Proc. Nat'l. Acad. Sci. U.S.A., 92:9353–9357 (1995); Pear et al., "Higher Plants Contain Homologs of the Bacterial celA Genes Encoding the Catalytic Subunit of Cellulose Synthase," Proc. Nat'l. Acad. Sci. U.S.A., 93:12637–12642 (1996); Tummala, "Response of Sucrose Phosphate Synthase Activity to Cool Temperatures in Cotton," M.S. thesis, Texas Tech University, Lubbock, Tex. (1996)). UDP-glucose pyrophosphorylase converts glucose-1-P to UDP-glucose or mediates the reverse reaction. In the context of cellulose synthesis, sucrose synthase is thought to degrade sucrose and supply UDP-glucose to cellulose synthase. Cellulose synthase transfers the glucose to the elongating β-1,4-linked cellulose polymer while free UDP is recycled to sucrose synthase. Sucrose phosphate synthase may use fructose-6-P (e.g. that derived from the fructose released by the degradative action of sucrose synthase) and UDP-glucose to synthesize additional sucrose to support cellulose synthesis (Delmer, "Cellulose Biosynthesis in Developing Cotton Fibers," in Basra, ed., Cotton Fibers: Developmental Biology, Quality Improvement, and Textile Processing, Haworth Press:New York, pp. 85–112 (1999)).

All of the enzymes just discussed operate within the pathways of sugar metabolism leading to the formation of the β-1,4-linked glucan polymer. Evidence from other systems and cotton fibers implicates other possible points of regulation of cellulose synthesis coincident with or after formation of the glucan polymer, although the relevant pathways and proteins are incompletely understood. Examples of other relevant proteins include β-1,4-glucanase that may act as a glucan chain editor or in some other role (Delmer, "Cellulose Biosynthesis: Exciting Times For a Difficult Field of Study," Ann. Rev. Plant Physiol. Mol. Biol., 50:245–276 (1999)) and glycoproteins that may act as primers for cellulose biosynthesis (Lukowitz et al., "Arabidopsis cyt1 Mutants are Deficient in a Mannose-1-Phosphate Guanyltransferase and Point to a Requirement of N-Linked Glycosylation for Cellulose Biosynthesis," *Proc. Nat'l. Acad. Sci. U.S.A.*, 98:2262–2267 (2001)). Mutations that down-regulate β-1,4-glucanase or glycoprotein synthesis cause reduced cellulose content in other systems (Nicol et al., "Plant Cell Expansion: Scaling the Wall," *Current Opinion in Cell Biology*, 1:12–17 (1998); Lukowitz et al., "*Arabidopsis cyt1* Mutants are Deficient in a Mannose-1-Phosphate Guanyltransferase and Point to a Requirement of N-Linked Glycosylation for Cellulose Biosynthesis," *Proc. Nat'l. Acad. Sci. U.S.A.*, 98:2262–2267 (2001)). In *Arabidopsis,* mutation of xylem secondary wall specific cellulose synthase genes causes reduced cellulose content and weak xylem walls (Turner et al., "Collapsed Xylem Phenotype of *Arabidopsis* Identifies Mutants Deficient in Cellulose Deposition in the Secondary Cell Wall," *Plant Cell*, 9:689–701 (1997)). In cotton, increased expression of spinach sucrose phosphate synthase causes increased cellulose content in fiber walls of plants growing under a cool night cycle (Haigler et al., "Transgenic Cotton Over-Expressing Sucrose Phosphate Synthase Produces Higher Quality Fibers With Increased Cellulose Content and Has Enhanced Seed Cotton Yield," Abstract 477. In: *Proceedings of Plant Biology* 2000, July 15–19, San Diego, Calif., American Society of Plant Physiologists, Rockville, Md., (2000)). These findings indicate that it is possible to manipulate the quantity of cellulose in secondary walls, but presently there is insufficient identification of target genes that might be beneficially manipulated.

Studies that identify genes that are under tissue-specific and developmental regulation are important in understanding the roles of proteins in fiber development and cell-wall architecture (John, "Structural Characterization of Genes Corresponding to Cotton Fiber mRNA, E6: Reduced E6 Protein in Transgenic Plants by Antisense Gene," *Plant Mol. Biol.*, 30:297–306 (1996)). In addition, such genes and their regulatory elements are important tools for fiber modification through genetic engineering (John, "Prospects for Modification of Fibers Through Genetic Engineering of Cotton," in Gebelein, eds., *Industrial Biotechnological Polymers*, Lancaster, Pa.:Technomic, pp. 69–79 (1995); John, "Genetic Engineering Strategies for Cotton Fiber Modification. In: A. S. Basra (ed.), *Cotton Fibers: Developmental Biology, Quality Improvement, and Textile Processing*, The Haworth Press, New York, pp. 271–289 (1999)).

In many instances, it would be desirable for a transgene to be developmentally regulated to have exclusive or preferential expression in fiber cells at a proper developmental stage. This regulation can be most expeditiously accomplished by a promoter capable of preferential promotion.

Promoters are DNA elements that direct the transcription of RNA in cells. Together with other regulatory elements that specify tissue and temporal specificity of gene expression, promoters control the development of organisms. Thus, there has been a concerted effort in identifying and isolating promoters from a wide variety of plants and animals.

Many promoters function properly in heterologous systems. For example, promoters taken from plant genes such as rbcS, Cab, chalcone synthase, and protease inhibitor from tobacco and Arabidopsis are functional in heterologous transgenic plants. (Benfey et al., "Regulated Genes in Transgenic Plants," *Science*, 244:174–181, (1989)). Specific examples of transgenic plants include tissue-specific and developmentally regulated expression of soybean 7s seed storage protein gene in transgenic tobacco plants (Chen et al., "A DNA Sequence Element That Confers Seed-Specific Enhancement to a Constitutive Promoter," *EMBO J.*, 7:297–302, (1988)) and light-dependent organ-specific expression of *Arabidopsis thaliana* chlorophyll a/b binding protein gene promoter in transgenic tobacco (Ha et al., "Identification of Upstream Regulatory Elements Involved in the Developmental Expression of the *Arabidopsis thaliana* Cab-1 Gene," *Proc. Natl. Acad. Sci. USA*, 85:8017–8021, (1988)). Similarly, anaerobically inducible maize sucrose synthase-1 promoter activity was demonstrated in transgenic tobacco (Yang et al., "Maize Sucrose Synthase-1 Promoter Directs Phloem Cell-Specific Expression of Gus Gene in Transgenic Tobacco Plants," *Proc. Natl. Acad. Sci. USA*, 87: 4144–4148, (1990)). Tomato pollen promoters were found to direct tissue-specific and developmentally regulated gene expression in transgenic Arabidopsis and tobacco (Twell et al., "Pollen-Specific Gene Expression in Transgenic Plants Coordinate Regulation of Two Different Tomato Gene Promoters During Microsporogenesis," *Development*, 109:705–714, (1990)). Thus, some plant promoters can be utilized to express foreign proteins in plant tissues in a developmentally regulated fashion.

Tissue-specific and developmentally regulated expression of genes has also been shown in fiber cells. Several of these, such as E6, vacuolar ATPase, and lipid transfer-type proteins, have strong expression in cotton fibers during primary wall deposition (Wilkins et al., "Molecular Genetics of Developing Cotton Fibers," in Basra, ed., *Cotton Fibers: Developmental Biology, Quality Improvement, and Textile Processing*, Haworth Press:New York, p. 231–270 (1999); Orford et al., "Expression of a Lipid Transfer Protein Gene Family During Cotton Fibre Development," *Biochimica and Biophysica Acta*, 1483:275–284 (2000)). Other genes show transient expression during fiber development. For example, Rac is transiently expressed at the primary to secondary wall stage transition (Delmer et al., "Genes Encoding Small GTP-Binding Proteins Analogous to Mammalian Rac are Preferentially Expressed in Developing Cotton Fibers," *Mol. Gen. Genet.*, 248:43–51 (1995)) and another lipid transfer-type protein, FS18A (Orford et al., "Characterization of a Cotton Gene Expressed Late in Fibre Cell Elongation," *Theoretical and Applied Genetics*, 98:757–764 (1999)), is transiently expressed at 24 DPA during secondary wall deposition. Another gene, H6, is expressed between 10–24 DPA, which includes both primary and early secondary wall deposition, but, after the promoter of this gene has commenced activity during primary wall deposition, there is post-transcriptional control of gene expression so that H6 protein accumulates only during secondary wall deposition at 15–40 DPA (John et al., "Characterization of mRNA for a Proline-Rich Protein of Cotton Fiber," *Plant Physiology*, 108:669–676 (1995)). At the level of gene expression, only certain cellulose synthase genes have been previously shown to have preferential and prolonged expression in cotton fibers during secondary wall deposition, although there were lower levels of expression during primary wall deposition and in other parts of the plant. In addition, cellulose synthase did not show strong expression until 20 DPA, with only weak expression observed at 17 DPA (Pear et al., "Higher Plants Contain Homologs of the Bacterial celA Genes Encoding the Catalytic Subunit of Cellulose Synthase," *Proc. Nat'l. Acad. Sci. U.S.A.*, 93:12637–12642 (1996)). Another gene, FbL2A, is up-regulated at the primary to secondary wall transition (weakly at 15 DPA and strongly at 20 DPA) (Rinehart et al., "Tissue-Specific and Developmental Regulation of Cotton Gene FbL2A," *Plant Physiology*, 112:1331–1341 (1996)).

Any of the genes expressed in cotton fibers are candidates for containing useful promoters, with a particular class of useful promoter being those that are preferentially expressed in fibers and/or secondary walled cells compared to other cell types and/or developmental stages. Promoters expressing preferentially during the primary wall stage of fiber development will also have particular uses. It may also be advantageous to have promoters that express in cotton fibers and certain restricted classes of cells (for example, secondary walled cells) in other parts of the cotton plant. Promoters with different strength are also valuable because different genetic engineering goals may be best accomplished with different amounts of the foreign protein being present in the cell or tissue. The biotechnology industry dealing with any particular species will ultimately desire and need a "toolbox" of promoters so that the most appropriate one for any particular use may be chosen. Each promoter will have a combination of unique characteristics in terms of cell, tissue, or developmental specificity of driving gene expression, strength of gene expression, degree of susceptibility to positional effects of gene insertion on level of gene expression, susceptibility to gene silencing, and any number of other similar phenomena that affect transcription.

A few promoters of genes expressed in cotton fibers have been isolated and tested in stably transformed cotton and with relationship to two or more time points in the time course of fiber development, where the testing involved promoter fusions with "reporter" genes or genes that are part of putatively useful genetic engineering strategies. Three major patterns were observed, one typified by the Gh10 promoter (for an acyl carrier protein), which drives foreign gene expression throughout fiber development (Song et al., "Expression of a Promoter from a Fiber-Specific Acyl Carrier Protein Gene in Transgenic Cotton Plants," *Proc. Beltwide Cotton Conf.*, 1:486–488 (1998)). A second pattern was typified by the E6 promoter, which drives gene expression preferentially at the primary wall stage of cotton fiber development (U.S. Pat. No. 5,521,078 to John). A third pattern was shown by the promoter of the FbL2A gene. This promoter was tested by fusion to two reporter genes (polyhydroxyalkanoic acid synthase or PHA synthase, an enzyme that was detected with a specific antibody, and acetoacetyl-CoA reductase, an enzyme with activity that was monitored by enzyme assay) and transformation of cotton (Rinehart et al., "Tissue-Specific and Developmental Regulation of Cotton Gene FbL2A," *Plant Physiology*, 112:1331–1341 (1996)). However, by use of the two promoter/reporter gene constructs, somewhat contradictory data were provided on the utility of the promoter of FbL2A. When the acetoacetyl-CoA reductase gene was under control of the FbL2A promoter, acetoacetyl-CoA reductase activity was detected in cotton fibers during primary wall deposition at 5–10 DPA, and there was consistent, substantial activity by 20 DPA during secondary wall deposition, peak activity at 35 DPA, and continued activity until 45 DPA among a family of independently transformed plants (Rinehart et al., "Tissue-Specific and Developmental Regulation of Cotton Gene FbL2A," *Plant Physiology*, 112:1331–1341 (1996)). However, the enzyme activity after 20 DPA could be due to long-lived messenger RNA or protein synthesized at 15–20 DPA, which is the period when the data directly show FbL2A gene expression under control of its own promoter. In contrast, when the PHA synthase gene was under the control of the FbL2A promoter, Western blotting to detect PHA synthase immunologically in a transformed plant showed only very weak signal during secondary wall deposition at 20 DPA, a trace signal at 25 DPA, and no signal at 30 or 35 DPA (Rinehart et al., "Tissue-Specific and Developmental Regulation of Cotton Gene FbL2A," *Plant Physiology*, 112:1331–1341 (1996)). Furthermore, the PHA synthase gene under the control of the putatively consitutive 35S promoter from CaMV virus correlated with detection of PHA synthase protein strongly during primary wall deposition at 10 DPA and weakly continuing through 35 DPA of secondary wall deposition. The comparative patterns during secondary wall deposition are consistent with transient expression of the FbL2A promoter around 20 DPA of secondary wall deposition. The data also show that the FbL2A promoter will drive weak foreign gene expression in cotton fibers during primary wall deposition (Rinehart et al., "Tissue-Specific and Developmental Regulation of Cotton Gene FbL2A," *Plant Physiology*, 112:1331–1341 (1996)). Further, graphical data in U.S. Pat. No. 6,211,430 to John showed that the FbL2A promoter activity was not substantial until 20 DPA (about 5 days past the onset of secondary wall deposition) and that 50% of maximal foreign acetoacetyl-CoA reductase activity was not detectable until 31 DPA (about 16 days past onset of secondary wall deposition).

Thus, it would be useful to have a promoter that would drive gene expression preferentially and strongly in secondary walled cells—fibers, in particular—throughout secondary wall deposition, i.e., strongly and continuously (e.g. at $\geq 50\%$ of its maximal activity) from the initiation of secondary wall deposition to its termination. The initiation of secondary wall deposition is defined as the time when the dry weight/unit length of a cotton fiber begins to increase or when the dry weight/unit surface area of any cell begins to increase via synthesis of new wall material containing more than 30% (w/w) of cellulose. In the case of cotton fiber of *G. hirsutum* L., this is expected to occur between 14–17 DPA when cotton plants are grown under typical conditions in the greenhouse or the field (day temperature of 26–34° C., night temperature of 20–26° C., light intensity greater than or equal to 1000 µeinsteins/m$^2$/s, with adequate water and mineral nutrition). Furthermore, it would be useful to have a promoter that would drive gene expression only or preferentially in secondary walled cells such as fibers while excluding or minimizing expression in other cell types.

The present invention is directed to achieving these objectives.

SUMMARY OF THE INVENTION

The present invention relates to an isolated nucleic acid molecule from cotton encoding an endogenous cotton protein related to chitinase, where the nucleic acid molecule is expressed preferentially in secondary walled cells during secondary wall deposition. A polypeptide encoded by the isolated nucleic acid molecule is also disclosed.

Another aspect of the present invention relates to a DNA construct including a DNA promoter operably linked 5' to a second DNA to induce transcription of the second DNA, the second DNA, which is the isolated nucleic acid molecule, and a 3' regulatory region operably linked to the second DNA. The DNA construct can be incorporated in an expression system, a host cell, a plant, or a plant seed.

Another aspect of the present invention relates to an isolated DNA promoter suitable for inducing expression of a protein encoded by a second DNA operably associated with the DNA promoter. The DNA promoter is isolated from cotton and drives expression preferentially in secondary walled cells during secondary wall deposition.

Another aspect of the present invention relates to a DNA construct including the isolated DNA promoter, a second DNA encoding a protein or polypeptide, where the DNA promoter is operably linked 5' to the second DNA to induce transcription of the second DNA, and a 3' regulatory region operably linked to the second DNA. The DNA construct may be incorporated in an expression system, a host cell, a plant, or a plant seed.

Also disclosed is a method of imparting resistance to plants against insects and fungi involving transforming a plant with the isolated nucleic acid molecule of the present invention.

Another aspect of the present invention relates to a method of regulating the cellulose content of a plant fiber involving transforming a plant with the isolated nucleic acid molecule of the present invention.

A further aspect of the present invention is directed to a method of expressing a gene preferentially in secondary walled cells during secondary wall deposition in a plant involving transforming a plant with the DNA construct including the isolated DNA promoter of the present invention.

The finding that the isolated nucleic acid molecule disclosed in the present invention is expressed preferentially in secondary walled cells such as fibers during secondary wall deposition when cellular activity is strongly skewed toward cellulose synthesis is consistent with a developmental role for the corresponding chitinase-related protein in cellulose synthesis. Alternatively, the protein could be "stored" in the cotton fiber cell wall awaiting fungal attack after boll opening. However, any chitinase with this defensive function in cotton fibers may be relatively ineffective because cotton fibers can be infected and greatly damaged by several fungal species (Simpson et al., "The Geographical Distribution of Certain Pre-Harvest Microbial Infections of Cotton Fiber in the U.S. Cotton Belt," *Plant Disease Reporter*, 55:714–718 (1971)). Whether acting developmentally or defensively, manipulating the expression of these chitinase-related proteins in fibers could have important consequences for fiber crop production and quality. For example, fiber cellulose content could be enhanced or diminished during biosynthesis and/or protected from fungal degradation during crop harvesting and processing.

In addition, a promoter of a gene that is expressed preferentially in secondary walled cells such as fibers during secondary wall deposition of normal plants can be valuable for genetic engineering of fiber to achieve: (1) improved agricultural productivity under normal and stressed conditions and (2) improved fiber properties that depend on modification during secondary wall deposition. Since there is no known gene that encodes a functional protein that is preferentially and strongly expressed in secondary walled cells such as fibers throughout secondary wall deposition, there is no promoter to drive foreign gene expression preferentially and strongly throughout the whole duration of fiber secondary wall deposition. The promoter disclosed in the present invention allows these goals to be met while avoiding or minimizing pleiotropic effects on plant growth and development or other stages of fiber development that could reduce the benefit of the targeted effects.

DPA (FIG. 9B) is from lines 2.2-7-14b, 2.2-47-5a, and 2.2-55-1a, respectively. Consistent results were observed for many lines of all three promoter lengths. Incubation with substrate occurred for 1 h. No blue color was evident at 13 DPA, very faint blue in some areas of fiber occurred by 14 DPA, intense blue in some areas had developed by 16 DPA, and uniform brilliant blue occurred by 17 DPA. The intense blue color persisted in living fibers until at least 40 DPA, the last day tested. Some fiber was pulled away from the 27 DPA seed to show that the non-fiber cells of the seed epidermis did not express GUS.

FIGS. 10A–D illustrate that short linters remained white, while lint fiber was intensely blue. FIG. 10A shows that, when lint fiber was removed from the seed, a fringe of white linters overlay the remaining blue lint fiber (line 2.2-47-1c). FIG. 10B shows that the short linters (center of picture) were pulled off selectively and laid next to the blue lint fiber that was still attached to the seed (upper right corner) (line 2.2-47-5a). FIGS. 10C–D show that the linters (line 1.4-8-8a) were alive and engaged in secondary wall deposition, as shown by helical microfibrils (FIG. 10C, DIC and arrow) and thick walls surrounding a granular protoplast (FIG. 10D, brightfield).

FIGS. 11A–B show micrographs of the same area of embedded and sectioned petiole tissue (line 2.2-2-2a) shown in brightfield optics (FIG. 11A) and polarization optics (FIG. 11B). White birefringence in polarization optics indicates the presence of crystalline material such as cellulose, and thick secondary walls with highly ordered cellulose microfibrils show much brighter birefringence. A microwave-assisted method of paraffin embedding (Ruzin, *Plant Microtechnique and Microscopy*, 322 pp, Oxford Univ. Press, Oxford (1999), which is hereby incorporated by reference in its entirety) allowed the delicate cambium (FIG. 11A, double arrow), which contains birefringent crystals, to be preserved. The xylem is on the bottom and the phloem is in the top, left, corner. In FIG. 11A, blue color arising from GUS activity is faint in two phloem cells and intense in some xylem cells. Comparison of the polarization image shows that all blue cells have thicker cell walls, as indicated by bright white birefringence, and that GUS is often not expressed in adjacent cells that have not started to thicken their walls. The cells with the thickest walls (visible via DIC and polarization) were not expressing GUS because they had already completed their developmental program and died to become conducting cells or supporting fibers in the vascular tissue.

Figure 12A:
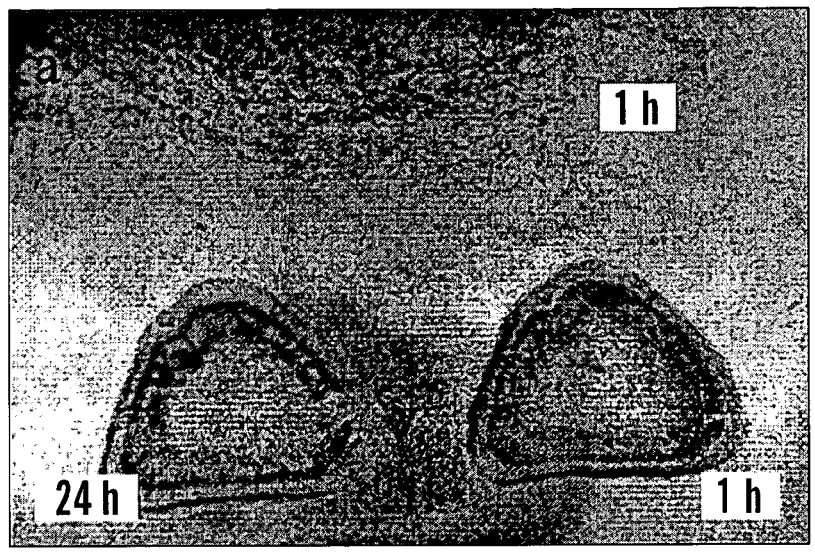
Figure 12B:
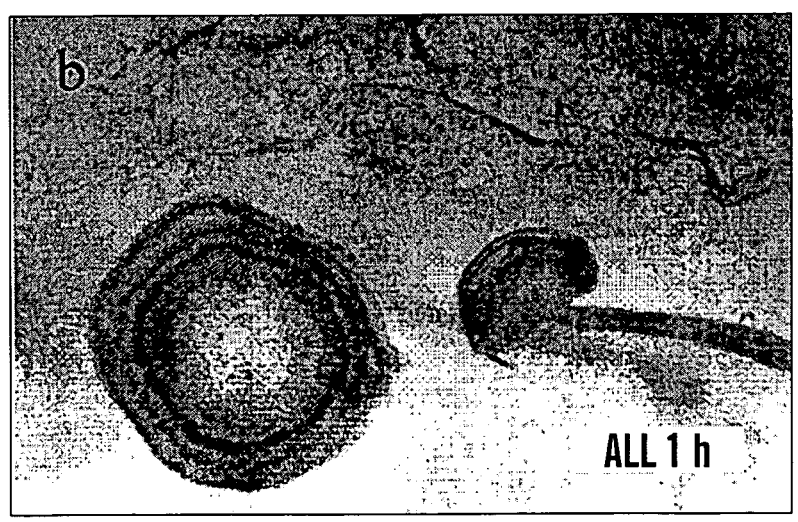

FIGS. 12A–B illustrate comparison of staining intensity in fibers compared to other tissues. Fiber ≧17 DPA stained strong blue after 1 h (FIGS. 12A and B), but vegetative tissues in moderately expressing lines had visible staining only after 4–24 h (FIG. 12A; line 1.8-16-7b). (Staining for 4 h was usually equivalent to staining for 24 h. The 1 h and 24 h sections were adjacent in the plant.) In the strongest expressing lines, vegetative tissues also had visible staining after 1 h (FIG. 12B; line 2.2-47-5a).

DETAILED DESCRIPTION OF THE INVENTION

The present invention relates to an isolated nucleic acid molecule from cotton encoding an endogenous cotton chitinase. The nucleic acid molecule is expressed preferentially in secondary walled cells during secondary wall deposition.

Preferential expression in secondary walled cells during secondary wall deposition means gene expression in the secondary walled cell during secondary wall deposition at a level more than 100 times higher than in other cell types or at other stages of cell development. Comparative levels of gene expression can be assessed by various standard molecular biological techniques including semi-quantitative Northern blotting and real-time quantitative PCR.

"Secondary wall" defines a plant cell wall that is typically greater than or equal to 0.2 μm thick and contains greater than or equal to 30% (w/w) cellulose among other components that may include other polysaccharides, proteins, phenolic molecules, and/or lignin. Cells with secondary walls can have any shape and be alive or dead at maturity. Typically, secondary walled cells are commonly found in fibers but are also found in other cell types including some thickened epidermal or parenchyma cells.

The word "fiber" is often used to unify a diverse group of plant cell types that share in common the features of having an elongated shape and abundant cellulose in thick cell walls, usually, but not always, described as secondary walls. Such walls may or may not be lignified, and the protoplast of such cells may or may not remain alive at maturity. Such fibers have many industrial uses, for example in lumber and manufactured wood products, paper, textiles, sacking and boxing material, cordage, brushes and brooms, filling and stuffing, caulking, reinforcement of other materials, and manufacture of cellulose derivatives. In some industries, the term "fiber" is usually inclusive of thick-walled conducting cells such as vessels and tracheids and fibrillar aggregates of many individual fiber cells. Here the term "fiber" is used in its most inclusive sense, for example including: (a) thick-walled conducting and non-conducting cells of the xylem; (b) fibers of extraxylary origin, including those from phloem, bark, ground tissue, and epidermis; and (c) fibers from stems, leaves, roots, seeds, and flowers or inflorescences (such as those of *Sorghum vulgare* used in the manufacture of brushes and brooms). In addition to wood from trees, cotton, and forage crops, the invention is applicable to all fibers, including, but not exclusively, those in agricultural residues such as corn, sugar cane, and rice stems that can be used in pulping, flax, hemp, ramie, jute, kenaf, kapok, coir, bamboo, spanish moss, abaca, and *Agave* spp. (e.g. sisal).

In one embodiment of the present invention, the secondary walled cells are cotton fiber. Typically, the cotton fiber is lint fiber. Lint fibers initiate elongation a few days earlier than linters (also called fuzz fibers). Fuzz fibers remain very short and are not valuable as textile fibers, providing a source of chemical cellulose instead. Fuzz fibers are removed from cotton seeds before crushing for oil, and they have a value of only 9.7 cents per pound, whereas the long lint fiber typically sells for 40–60 cents per pound. In another embodiment, the secondary walled cells are xylem and phloem cells of stems, hypocotyls, or roots.

The isolated nucleic acid molecule of the present invention can have a nucleotide sequence of SEQ ID NO: 1, identified herein as F285, as follows:

```
ATG GAG GCC AAA TGG CTG CTA TGT TTT ACA ATG GCA
GCA CTA ATG GCA GTG TCA AAT GGC CAG GAA TCA GTG
AAG CCA TTG GTG AAG ATA GTT AAA GGC AAC AAA CTT
TGT GAT AAA GGG TGG GAA TGT AAA GGG TGG TCA CAG
TTT TGT TGT AAC CAA ACC ATT TCT GAT TAT TTC CGA
ACT TAT CAA TTT GAG AAC CTT TTC GCT AAA CGT AAT
```

-continued

```
ACA CCG GTG GCA CAT GCG GTT GGG TTC TGG GAT TAC

CAT TCT TTC ATT ACG GCG GCG GCT CAG TAT CAG CCT

CAT GGT TTT GGT ACC ACC GGC GGT AAG CTG CAG AGC

ATG AAG GAA GTG GCA GCT TTT CTT GGA CAT GTC GGC

AGC AAA ACT TCA TGT GGT TAT GGA GTG GCA ACT GGG

GGA CCA TTG GCT TGG GGT CTA TGC TAC AAC AAG GAA

ATG AGT CCT AGC AAA TTG TAT TGT GAT GAT TAC TAC

AAA TAC ACC TAC CCT TGC ACT CCT GGA GTT TCT TAC

CAT GGC CGT GGT GCC TTG CCT ATC TAT TGG AAC TAC

AAC TAT GGA GAA ACA GGC GAC GCA TTG AAG GTG GAC

TTA TTG AAC CAC CCT GAA TAC ATA GAA AAC AAT GCA

ACC TTA GCT TTC CAG GCA GCA CTC TGG AGA TGG ATG

ACA CCG GTG AAG AAA CAC CAA CCG TCG GCC CAC GAC

GTG TTT GTC GGC AGC TGG AAA CCG ACC AAG AAC GAC

ACG TTG GCC AAG CGG GTC CCG GGG TTT GGA GCC ACC

ATG AAT GTG CTC TAT GGA GAT CAA GTT TGT GGG CGA

GGT GAT GTT GAC ACC ATG AAC AAC ATC ATC TCT CAT

TAC CTT TCT TAC CTT GAC CTA ATG GGA GTT GGG AGA

GAA GAG GCA GGA CCC CAT GAA GTC CTC ACA TGT GAA

GAA CAA AAG CCT TTG ACT GTA TCT CCT TCT TCT GCA

TCA TCA TCA TCA TCA TCT TGA
```

Alternatively, the isolated nucleic acid molecule of the present invention can have a nucleotide sequence of SEQ ID NO: 3, identified herein as F286, as follows:

```
ATGGAAGCCAAATGGCTGGTTCTTTTTTCAGTGGCGGCAATGCTGGTGGC

ACTGGCCAACTGCCAGGAATCGTTGAAGCCATTGGTGAAGATGGTAAAGG

GCAAGAAGCTGTGTGACAAAGGGTGGGAATGTAAAGGGTGGTCAAAGTAT

TGTTGCAACCATACCATTTCTGATTACTTCCAAACTTACCAGTTTGAGGA

CCTTTTTGCGAAGCGTAACACGCCGGTAGCACATGCGGTTGGGTTCTGGG

ATTACCATTCCTTCATTACTGCTGCTGCTCAGTATCAGCCTCATGGATTT

GGTACCACCGGGGAAAAGCTCCAGAATATGAAGGAAGTCGCTGCTTTTCT

TGGACATGTCGGCAGCAAAACTTCATGTGGCTATGGAGTCGCTACCGGGG

GACCATTGGCTTGGGGTCTTTGCTACAACAAAGAAATGAGCCCTAGCAAA

ATATATTGCGATGATTACTATAAATACACCTATCCTTGCACACCAGGAGT

CTCATATCATGGCCGTGGTGCCTTGCCTATCTACTGGAACTACAACTATG

GGGAAACTGGAGAGGCTTTGAAGGTGGACTTGTTGAACCACCCAGAATAC

TTAGAAGACAACGCAACCTTGGCTTTCCAGACAGCAATGTGGAGGTGGAT

GACGCCGATGAAGAAACACCAACCCTCAGCCCATGACGTTTTCGTTGGCA

ACTGGAAACCAACCAAGAACGACACCTTGGCCAAGAGGGTTCCAGGTTTT

GGAACCACCATGAATCTTCTTTATGGTGACCAAGTTTGTGGTCAAGGTGA

TAGTGATTCCATGAACAATATGATCTCTCATTACCTTTATTACCTTGACC

TTTTGGGAGTTGGCCGAGAAGAAGCTGGTCCTCATGATATGCTCACCTGT

GAAGAACAAGAACCCTTCACTGTTTCTCCCTCATCTGCAACATCATCATG

A
```

The isolated nucleic acid molecule of the present invention can also include a nucleotide sequence which hybridizes to a DNA molecule having a sequence according to SEQ ID NO: 1 or SEQ ID NO: 3 under stringent conditions characterized by a hybridization buffer comprising 1×SSC at a temperature of 61° C.

The isolated nucleic acid molecule of SEQ ID NO: 1 encodes a protein or polypeptide having a deduced amino acid sequence of SEQ ID NO: 2 as follows:

MEAKWLLCFTMAALMAVSNGQESVKPLVKIVKGKKLCDKGWECKGWSQFC

CNQTISDYFRTYQFENLFAKRNTPVAHAVGFWDYHSFITAAAQYQPHGFG

TTGGKLQSMKEVAAFLGHVGSKTSCGYGVATGGPLAWGLCYNKEMSPSKL

YCDDYYKYTYPCTPGVSYHGRGALPIYWNYNYGETGDALKVDLLNHPEYI

ENNATLAFQAALWRWMTPVKKHQPSAHDVFVGSWKPTKNDTLAKRVPGFG

ATMNVLYGDQVCGRGDVDTMNNITSHYLSYLDLMGVGREEAGPHEVLTCE

EQKPFTVSPSSASSSSS

The isolated nucleic acid molecule of SEQ ID NO: 3 encodes a protein or polypeptide having a deduced amino acid sequence of SEQ ID NO: 4 as follows:

MEAKWLVLFSVAAMLVALANCQESLKPLVKMVKGKKLCDKGWECKGWSKY

CCNHTISDYFQTYQFEDLFAKRNTPVAHAVGFWDYHSFITAAAQYQPHGF

GTTGEKLQNMKEVAAFLGHVGSKTSCGYGVATGGPLAWGLCYNKEMSPSK

IYCDDYYKYTYPCTPGVSYHGRGALPTYWNYNYGETGEALKVDLLNHPEY

LEDNATLAFQTAMWRWMTPMKKHQPSAHDVFVGNWKPTKNDTLAKRVPGF

GTTMNVLYGDQVCGQGDSDSMNNMISHYLYYLDLLGVGREEAGPHDMLTC

EEQEPFTVSPSSATSS

Another suitable isolated nucleic acid molecule of the present invention encodes a protein or polypeptide including an amino acid sequence of SEQ ID NO: 5 as follows:
GRGALPIYWNYNYGETGDAL The isolated nucleic acid molecule of the present invention can also encode a protein or polypeptide including an amino acid sequence having at least 60% identity to SEQ ID NO: 5.

Another suitable isolated nucleic acid molecule of the present invention encodes a protein or polypeptide including an amino acid sequence of SEQ ID NO: 6 as follows:
MKEVAAFLGHVGSKTSCGYGVATGG-PLAWGLCYNKEMSP The isolated nucleic acid molecule of the present invention can also encode a protein or polypeptide including an amino acid sequence having at least 75% identity to SEQ ID NO: 6.

The amino acid sequences of SEQ ID NO: 2 and SEQ ID NO: 4 show homology to plant chitinases that are important in the defense or in the development of the cotton fiber. The present invention also relates to a polypeptide which is encoded by the isolated nucleic acid molecule of the present invention and has an amino acid sequence corresponding to SEQ ID NO: 2 or SEQ ID NO: 4. Alternatively, the polypeptide of the present invention can include an amino acid sequence of SEQ ID NO: 5 or SEQ ID NO: 6 or an amino acid sequence having at least 60% identity to SEQ ID NO: 5 or an amino acid sequence having at least 75% identity to SEQ ID NO: 6.

The isolated nucleic acid molecule of the present invention is preferentially expressed in cotton fibers beginning at 14 to 17 DPA, preferably extending through to the termination of secondary wall deposition. Most preferably, the isolated nucleic acid molecule of the present invention is preferentially expressed in cotton fibers beginning at 14 to 17 DPA up to 40 DPA. The isolated nucleic acid molecule of the present invention is the first cotton gene with homology to chitinase that is known to be expressed preferentially in fibers during secondary wall deposition. The gene's precise temporal regulation with secondary wall deposition suggests that the gene could be manipulated to change fiber development or defensive properties.

In a preferred form of the present invention, the isolated nucleic acid molecule of the invention is in a DNA construct including a DNA promoter operably linked 5' to a second DNA encoding a protein or polypeptide to induce transcription of the second DNA. The second DNA includes the isolated nucleic acid molecule of the invention. A 3' regulatory region is operably linked to the second DNA.

In another embodiment, the present invention is an expression system that includes a suitable vector containing the DNA construct of the invention. The expression system contains the necessary elements for the transcription and translation of the inserted protein-coding sequences. In preparing the DNA construct for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *A. tumefaciens* (Fraley et al., "Expression of Bacterial Genes in Plant Cells," *Proc. Nat'l Acad. Sci. USA*, 80: 4803–4807 (1983), which is hereby incorporated by reference in its entirety).

Further improvement of this technique led to the development of the binary vector system (Bevan, M., "Binary *Agrobacterium* Vectors for Plant Transformation," *Nucleic Acids Res.*, 12:8711–8721 (1984), which is hereby incorporated by reference in its entirety). In this system, all the T-DNA sequences (including the borders) are removed from the pTi, and a second vector containing T-DNA is introduced into *A. tumefaciens*. This second vector has the advantage of being replicable in *E. coli* as well as *A. tumefaciens* and contains a multiple cloning site that facilitates the cloning of a transgene. An example of a commonly used vector is pBin19 (Frisch, et al., "Complete Sequence of the Binary Vector Bin19," *Plant Molec. Biol.*, 27:405–409 (1995), which is hereby incorporated by reference in its entirety). Any appropriate vectors now known or later described for plant transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures, including prokaryotic organisms and eukaryotic cells grown in tissue culture.

Once the DNA construct of the present invention has been cloned into an expression system, as described above, they are ready to be incorporated into a host cell. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably, the host cells are either a bacterial cell (e.g., *Agrobacterium*) or a plant cell. Examples of plant cells include cells from trees, forage crops, cotton, corn, sugar cane, and rice stems that can be used in pulping, flax, hemp, ramie, jute, kenaf, kapok, coir, bamboo, spanish moss, abaca, and *Agave* spp. (e.g. sisal). Most preferably, the plant cell is from cotton.

In other embodiments of the present invention, plants or seeds are produced by transformation with the DNA construct of the present invention.

The present invention also relates to a method of imparting resistance to insects and fungi involving transforming a plant with a DNA construct that contains the chitinase-encoding nucleic acid molecule of the present invention. The DNA construct of the present invention can be utilized to impart resistance to insects and fungi for a wide variety of fiber-producing plants such as trees, forage crops, cotton, corn, sugar cane, and rice stems that can be used in pulping, flax, hemp, ramie, jute, kenaf, kapok, coir, bamboo, spanish moss, abaca, and *Agave* spp. (e.g. sisal). The DNA construct is particularly well suited to imparting resistance to cotton.

One approach to transforming plant cells with the nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824–5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene (Fraley, et al., "Liposome-Mediated Delivery of Tobacco Mosaic-Virus RNA Into Tobacco Protoplasts—A Sensitive Assay for Monitoring Liposome-Protoplast Interactions," *Proc. Nat'l. Acad. Sci. USA*, 79:1859–1863 (1982), which is hereby incorporated by reference in its entirety).

Stable transformants are preferable for the methods of the present invention. An appropriate method of stably introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. In one embodiment of the present invention, transformants are generated using the method of Frary et al., *Plant Cell Reports*, 16:235 (1996), which is hereby incorporated by reference in its entirety, to transform seedling explants.

Plant tissues suitable for transformation include, but are not limited to, floral buds, leaf tissue, root tissue, hypocotyl tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, also known as gusA or GUS, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO Journal*, 6:3901–3907 (1987), which is hereby incorporated by reference in its entirety). GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

Other suitable selection markers include, without limitation, markers encoding for antibiotic resistance, such as the nptII gene which confers kanamycin resistance (Fraley et al., "Expression of Bacterial Genes in Plant Cells," *Proc. Natl. Acad. Sci. USA*, 80:4803–4807 (1983), which is hereby incorporated by reference in its entirety) and the dhfr gene, which confers resistance to methotrexate (Bourouis et al., "Vectors Containing a Prokaryotic Dihydrofolate Reductase Gene Transform Drosophila Cells to Methotrexate-Resistance," *EMBO J.*, 2:1099–1104 (1983), which is hereby incorporated by reference in its entirety).

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures, Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

It is known that practically all plants can be regenerated from cultured cells or tissues, including but not limited to, all major species of cotton, rice, wheat, barley, rye, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

After the nucleic acid molecule of the present invention is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

The present invention also relates to a method of regulating the cellulose content of a plant fiber involving transforming a plant with a DNA construct that contains the chitinase-encoding nucleic acid molecule of the present invention. The same approaches to transforming plant cells with the nucleic acid molecule of the present invention mentioned above could be used. The DNA construct of the present invention can be utilized to modulate fiber development by regulating cellulose synthesis for a wide variety of fiber-producing plants such as trees, forage crops, cotton, corn, sugar cane, and rice stems that can be used in pulping, flax, hemp, ramie, jute, kenaf, kapok, coir, bamboo, spanish moss, abaca, and *Agave* spp. (e.g. sisal). The DNA construct is particularly well suited to modulating fiber development of cotton.

Several kinds of evidence suggest that chitinases are located in healthy plant organs, and one developmental role of a chitinase in embryogenesis has been well-characterized. A carrot mutant defective in somatic embryogenesis can be rescued by addition of an acidic, glycosylated, extracellular, chitinase (EP3) to the culture medium (de Jong et al., "A Carrot Somatic Embryo Mutant is Rescued by Chitinase," *Plant Cell*, 4:425–433 (1992), which is hereby incorporated by reference in its entirety). The rescue could be duplicated by addition of lipochitin oligosaccharides (Schmidt et al., "Signal Molecules Involved in Plant Embryogenesis," *Plant Molecular Biology*, 26:1305–1313 (1994), which is hereby incorporated by reference in its entirety) and by some but not all other chitinases (Kragh et al., "Characterization of Chitinases Able to Rescue Somatic Embryos of the Temperature-Sensitive Carrot Variant TS11," *Plant Molecular Biology*, 31:631–645 (1996), which is hereby incorporated by reference in its entirety). The EP3 gene was expressed in a small subset of cells of young fruits and mature seeds, suggesting that the chitinase acts to release chitin oligomers as developmental signals (possibly to reintiate cell division) for developing zygotic embryos (van Hengel, "Expression Patterns of the Carrot EP3 Endochitinase Genes in Suspension Cultures and in Developing Seeds," *Plant Physiology*, 117:43–53 (1998), which is hereby incorporated by reference in its entirety). Chitinase gene expression has also been associated with somatic embryogenesis in other species (Dong et al., "Endochitinase and β-1,3-Glucanase Genes are Developmentally Regulated During Somatic Embryogenesis in *Picea glauca*," *Planta*, 201:189–194 (1997), which is hereby incorporated by reference in its entirety). Arabinogalactan proteins (AGPs) are another class of molecules required for somatic embryogenesis, and some carrot AGPs contain glucosamine and N-acetyl-D-glucosaminyl and are sensitive to cleavage by chitinases. Pretreatment of AGPs with chitinase made them more active in promoting embryogenesis of carrot protoplasts, implying that embryo rescue by chitinase may be mediated by their hydrolytic action on AGPs (van Hengel et al., "N-Acetylglucosamine and Glucosamine-Containing Arabinogalactan Proteins Control Somatic Embryogenesis," *Plant Physiology*, 125:1880–1890 (2001), which is hereby incorporated by reference in its entirety). In this case, AGPs would be one endogenous substrate for chitinases. It has been found that an AGP-type protein accumulates during cotton fiber secondary wall deposition (John et al., "Characterization of mRNA for a Proline-Rich Protein of Cotton Fiber," *Plant Physiology*, 108:669–676 (1995), which is hereby incorporated by reference in its entirety).

Chitinases have been associated with several other healthy plant tissues, including germinating seeds (Petruzzelli et al. "Distinct Ethylene- and Tissue-Specific Regulation of β-1,3-Glucanases and Chitinases During Pea Seed Germination," *Planta*, 209:195–201 (1999), which is hereby incorporated by reference in its entirety). Chitinase gene expression is associated with formation of flowers de novo from tobacco cell explants (Neale et al., "Chitinase, B-1,3-Glucanase, Osmotin, and Extensin are Expressed in Tobacco Explants During Flower Formation," *Plant Cell*, 2:673–684 (1990), which is hereby incorporated by reference in its entirety). Chitinase enzyme activity has been found in healthy *Petunia* flowers, being particularly high in the stigma after the anthers dehisce (Leung, "Involvement of Plant Chitinases in Sexual Reproduction of Higher Plants," *Phytochemistry*, 31:1899–1900 (1992), which is hereby incorporated by reference in its entirety). Similarly, a protein immunologically related to basic chitinase was identified in both the anthers and the upper portion of bean pistils (containing the stigma) (del Campillo et al., "Occurrence of 9.5 Cellulase and Other Hydrolases in Flower Reproductive Organs Undergoing Major Cell Wall Disruption," *Plant Physiology*, 99:1015–1020 (1992), which is hereby incorporated by reference in its entirety). In flowers, chitinase might have a developmental role or a defensive role in anticipation of possible fungal invasion of fragile tissues that are essential for reproductive success. Some proteins extracted from primary and secondary cell walls of various plant species in suspension culture and sequenced at their N-terminus have homology to chitinase sequences in the databases from French bean (P80800, P80808, P80792, P82432) and tobacco (P80783, P8233) (Robertson et al., "Differential Extraction and Protein Sequencing Reveals Major Differences in Patterns of Primary Cell Wall Proteins from Plants," *The Journal of Biological Chemistry*, 272:15841–15848 (1997); Blee et al., "Proteomic Analysis Reveals a Novel Set of Cell Wall Proteins in a Transformed Tobacco Cell Culture That Synthesizes Secondary Walls as Determined by Biochemical and Morphological Parameters," *Planta*, 212:404–415 (2001), which are hereby incorporated by reference in their entirety). However, since only short peptide sequences were available after N-terminal sequencing (maximum of eighteen amino acids), definite conclusions about the presence of authentic chitinases in these cell walls cannot be made.

Other than the N-acetyl-glucosamine-containing AGPs associated with embryo rescue (van Hengel et al., "N-Acetylglucosamine and Glucosamine-Containing Arabinogalactan Proteins Control Somatic Embryogenesis," *Plant Physiology*, 125:1880–1890 (2001), which is hereby incorporated by reference in its entirety), endogenous substrates of plant chitinases have not been characterized at the structural or functional levels. However, there is evidence that endogenous chitinase substrates of diverse molecular types exist in healthy plants. For example, a chitin-binding lectin, wheat germ agglutinin (WGA), or chitinase tagged with electron-dense colloidal gold labeled the vascular secondary cell walls very densely in healthy elm, tomato, eggplant, and potato plants. Adjacent primary walls or middle lamella regions were not labeled, which supports the specificity of the reaction (Benhamou et al., "Attempted Localization of Substrate for Chitinases in Plant Cells Reveals Abundant N-Acetyl-D-Glucosamine Residues in Secondary Walls," *Biologie Cellulaire*, 67:341–350 (1989), which is hereby incorporated by reference in its entirety). This labeling could not be abolished by pre-treatment with protease to digest protein or a microbial chitinase, but it was abolished by pretreatment with lipase to digest lipids. The absence of label after lipase treatment would appear to place these secondary wall molecules in a different class than the N-acetyl-glucosamine-containing AGPs that have been associated with embryo rescue. Rather, the data suggest that chitin oligomers exist within or in association with a lipid-containing molecule in secondary cell walls.

Molecules containing both chitin oligomers and lipid (a single fatty acyl group varying from C16:0 to C20:4) are known in the form of lipochitin oligosaccharides (LCOs), which are synthesized and secreted by nodulating bacteria (*Rhizobium*) to induce the formation of the symbiotic root nodule by their plant host (Bakkers et al., "Function of Chitin Oligosaccharides in Plant and Animal Development," in Jolles, eds., *Chitin and Chitinases,* Birkäuser Verlag: Basel, pp.71–84 (1999), which is hereby incorporated by reference in its entirety). This indicates that plants have capacity to recognize such molecules supplied from an exogenous organism as developmental signals, in this case to initiate nodule formation. Furthermore, similar molecules may exist endogenously within plants. Thin layer chromatography (TLC) of lipophilic compounds in extracts from flowers of the plant *Lathyrus odoratus* showed that they migrated similarly to LCOs and that some of them were susceptible to chitinase digestion (Spaink et al., "Rhizobial Lipo-Oligosaccharide Signals and Their Role in Plant Morphogenesis: Are Analogous Lipophilic Chitin Derivatives Produced by the Plant?," *Australian Journal of Plant Physiology*, 20:381–392 (1993), which is hereby incorporated by reference in its entirety).

Endogenous plant molecules similar to LCOs could contain growth-regulating chitin oligomers that are releasable by endogenous plant chitinases. The data on embryo rescue by chitinase already described provide one example. Also, tomato suspension cells respond to LCOs or chitin oligomers (such as might be released from more complex endogenous molecules by limited chitinase action) by transiently raising the pH of their culture medium (Staehelin et al., "Perception of *Rhizobium* Nodulation Factors by Tomato Cells and Inactivation by Root Chitinases," *Proc. Nat'l. Acad. Sci. U.S.A.*, 91:2196–2200 (1994), which is hereby incorporated by reference in its entirety). Other plant responses associated with chitin oligomers include synthesis of anti-fungal phytoalexins, induction of chitinases, induction of $K^+$ and $Cl^-$ release, and $H_2O_2$ synthesis (Gooday, "Aggressive and Defensive Roles for Chitinases," in Jolles, eds., *Chitin and Chitinases*, Birkäuser Verlag:Basel, pp. 157–170 (1999), which is hereby incorporated by reference in its entirety). Tobacco plants transformed to over-express LCO-synthesizing genes (NodA and NodB, either separately or in combination) from *Rhizobium* had reduced growth and altered leaf shape (Schmidt et al., "Alteration of Plant Growth and Development by *Rhizobium noda* and *nodb* Genes Involved in the Synthesis of Oligosaccharide Signal Molecules," *The Plant Journal*, 4:651–658 (1993), which is hereby incorporated by reference in its entirety), suggesting that NodA and NodB can interfere with plant biosynthetic processes required for morphogenesis (Bakkers et al., "Function of Chitin Oligosaccharides in Plant and Animal Development," in Jolles, eds., *Chitin and Chitinases*, Birkhäuser Verlag: Basel, pp.71–84 (1999), which is hereby incorporated by reference in its entirety). Such interference could occur at many levels. However, since both overall growth rate and normal plant organ morphogenesis depend heavily on cellulose synthesis, it is possible that NodA and NodB interfere directly with cellulose synthesis. Perhaps NodA and NodB bind to and process inappropriately an endogenous N-acetyl-glucosamine-containing plant substrate, creating a non-functional analog of an endogenous molecule required for cellulose synthesis.

Conversely, tobacco plants transformed to over-express a maize acidic class I chitinase showed a positive correlation between chitinase activity and seedling dry weight (Patil et al., "Possible Correlation Between Increased Vigour and Chitinase Activity Expression in Tobacco," *Journal of Experimental Botany*, 48:1943–1950 (1997), which is hereby incorporated by reference in its entirety), which has a large cellulose component. Although no mechanistic explanation was provided, it is possible that the foreign chitinase activity causes over-production of chitin oligomers that stimulate cellulose synthesis. Chitin oligomers could modulate cellulose synthesis either as developmental signals or as direct participants in the cellulose biosynthetic process. For example, oligomers of the N-acetylglucosamine-containing hyaluronan heteropolymer, $(\beta\text{-}1,4\text{-}GlcA\ \beta\text{-}1,3\text{-}GlcNAc)_n$, interact with a particular receptor to activate Rho and Rac1 GTPases, which lead to reorganization of the actin cytoskeleton (Lee et al., "Hyaluronan: A Multifunctional, Megadalton, Stealth Molecule," *Current Opinion in Cell Biology*, 12:581–586 (2000), which is hereby incorporated by reference in its entirety). Reorganization of the actin cytoskeleton occurs at the primary to secondary wall transition in cotton fibers to mediate the changed orientation of cellulose microfibrils (Seagull, "Cytoskeletal Involvement in Cotton Fiber Growth and Development," *Micron*, 24:643–660 (1993), which is hereby incorporated by reference in its entirety). A Rac gene is expressed transiently in cotton fibers at the time of this reorganization (Delmer et al., "Genes Encoding Small GTP-Binding Proteins Analogous to Mammalian Rac are Preferentially Expressed in Developing Cotton Fibers," *Mol. Gen. Genet.*, 248:43–51 (1995), which is hereby incorporated by reference in its entirety) and a related $H_2O_2$ burst may also mediate this transition (Potikha et al., "The Involvement of Hydrogen Peroxide in the Differentiation of Secondary Walls in Cotton Fibers," *Plant Physiology*, 119: 849–858 (1999), which is hereby incorporated by reference in its entirety). However, the prolonged expression of the isolated nucleic acid molecule disclosed in the present invention throughout secondary wall deposition argues for a role beyond transient control of signal transduction cascades and cytoskeletal organization involving Rac and $H_2O_2$ at the primary to secondary wall transition.

Other possibilities for the involvement of the isolated nucleic acid molecule disclosed in the present invention in cotton fiber cellulose synthesis can be proposed by analogy with other systems. LCOs or similar molecules such as dolichol-(N-acetyl-glucosamine)$_n$ could donate chitin-containing oligosaccharides to a protein as primers in a biosynthetic process (Spaink et al., "Rhizobial Lipo-Oligosaccharide Signals and Their Role in Plant Morphogenesis: Are Analogous Lipophilic Chitin Derivatives Produced by the Plant?," *Australian Journal of Plant Physiology*, 20:381–392 (1993), which is hereby incorporated by reference in its entirety), as exemplified by chitin biosynthesis in insects (Palli et al., "Molecular and Biochemical Aspects of Chitin Synthesis Inhibition," in Jolles, eds., *Chitin and Chitinases*, Birkäuser Verlag:Basel, pp. 85–98 (1999), which is hereby incorporated by reference in its entirety). It has been noted that little attention has been paid to the fact that two fungal chitinases and egg lysozyme act as catalysts in transglycosylation reactions (Collinge et al., "Plant Chitinases," *Plant J.*, 3:31–40 (1993), which is hereby incorporated by reference in its entirety). *Arabidopsis cyt*1 mutants lack sufficient mannose-1-phosphate guanyltransferase activity, and consequently they are deficient in production of GDP-mannose as required for N-glycosylation of proteins. They also exhibit 5-fold reduction in cellulose content and cannot proceed through normal embryo development (Lukowitz et al., "*Arabidopsis cyt*1 Mutants are Deficient in a Mannose-1-Phosphate Guanyltransferase and Point to a Requirement of N-Linked Glycosylation for Cellulose Biosynthesis," *Proc. Nat'l. Acad. Sci. U.S.A.*, 98:2262–2267 (2001), which is hereby incorporated by reference in its entirety). Since the N-glycosylation inhibitor, tunicamycin, also causes cellulose-deficiency, these authors suggest that an N-glycosylated peptide might act as a primer for cellulose synthesis, which is a resurrection of an old and much-debated hypothesis that cellulose synthesis does require a primer (Maclachlan, "Does β-Glucan Synthesis Need A Primer," in Brown, Jr., ed., *Cellulose and Other Natural Polymer Systems: Biogenesis, Structure, and Degradation*, Plenum Press:NY, pp. 327–339 (1982), which is hereby incorporated by reference in its entirety).

Another aspect of the present invention relates to an isolated DNA promoter suitable for inducing expression of a protein encoded by a second DNA operably associated with the DNA promoter. The DNA promoter is isolated from cotton and drives expression preferentially in secondary walled cells during secondary wall deposition. Typically, the secondary walled cells are cotton fiber —lint fiber, in particular. In another embodiment, the secondary walled cells are xylem and phloem cells of stems, hypocotyls, or roots. The isolated DNA promoter of the present invention can be used to drive the expression of heterologous proteins only or preferentially in secondary walled cells such as fibers during secondary wall deposition. This is especially important if the proteins might have adverse pleiotropic effects if expressed strongly at other stages or in other cell types. This promoter should be similarly useful to others, since many critical fiber properties are determined at the secondary wall stage of development and the massive secondary wall represents a potential "storage" point for novel fiber components including enzymes or structural molecules.

Gene regulation and expression is a complex interaction of intracellular and extracellular factors. *Arabidopsis thaliana*, with a genome size of 145 Mb, contains about 25,000 genes (Ausubel, "*Arabidopsis* Genome: A Milestone in Plant Biology," *Plant Physiology*, 124:1451–1454 (2000), which is hereby incorporated by reference in its entirety). These genes must be expressed in perfect coordination in order to have organized growth and proper responses to the environment. This is achieved by differential gene expression, in which the plant is able to turn different genes on and off depending on the stage of development, the type of tissue, and specific inducers from the environment.

Plant cells have several mechanisms to control gene expression, and they can be exerted at transcriptional, post-transcriptional, translational, and post-translational levels. However, much of the differential expression can be explained at the transcriptional level when the RNA polymerase II interacts with the DNA and multiple protein factors to initiate the synthesis of mRNA (Roeder, "The Role of Initiation Factors in Transcription by RNA Polymerase II," *Trends in Biochemical Science*, 21:327–335 (1996), which is hereby incorporated by reference in its entirety). The region of DNA involved in this pre-transcriptional interaction is called the "promoter." Promoters are usually located next to the 5' end of the coding region of a gene.

By sequencing, comparing, and modifying plant promoters, it has been possible to identify functional components in their DNA sequence. All known promoters are made of two general components: the core region and the regulatory region (Kornberg, "RNA Polymerase II Transcription Control," *Trends in Biochemical Science*, 21:325–326 (1996), which is hereby incorporated by reference in its entirety).

The core region is located immediately upstream of the 5' end of the coding region and is essential for the transcription process; however, in quantitative terms it is only responsible for a small percentage of the total gene expression. The core region is about 100 bp long and comprises a TATA box and the transcription start site. The TATA box is a sequence of approximately 13 bp, rich in thymidine and adenine residues. The TATA box is present in most, but not all, promoters of genes encoding proteins (Roeder, "The Role of Initiation Factors in Transcription by RNA Polymerase II," *Trends in Biochemical Science*, 21:327–335 (1996), which is hereby incorporated by reference in its entirety). This is the site of direct interaction with the RNA polymerase II (RNA Pol II) and with universal transcription factors (TAFs), which are a necessary part of the transcription complex (Verrijzer et al., "TAFs Mediated Transcriptional Activation and Promoter Selectivity," *Trends in Biochemical Science*, 21:338–342 (1996), which is hereby incorporated by reference in its entirety). General factors are proteins present in all cells and are very conserved from yeast to man (Guarente et al., "Conservation and Evolution of Transcriptional Mechanisms in Eukaryotes," *Trends in Genetics*, 8:27–32 (1992), which is hereby incorporated by reference in its entirety).

The regulatory region is located further upstream from the core region and can be as long as 2 kb or even more. This region is responsible for the control of gene expression either suppressing or enhancing the activity of the RNA polymerase II. The regulatory region is composed of several "boxes" or elements that vary in size from 4 to 300 bp. These elements are the binding sites for specific proteins that are involved in the modulation of differential expression of genes and confer cell-specific or gene-specific expression. Proteins at this level interact with TFIID, increasing its stability in promoter binding, enhancing transcription. The presence of multiple elements and their corresponding factors produces a synergistic effect in transcription The most dynamic part of the promoter system is the interaction of the protein factors with the DNA and with the other proteins in the complex. For these interactions, proteins must contain structural domains that recognize specific surface characteristics of the minor or major grooves and the sugar-phosphate backbone of the DNA (Travers, "DNA-Protein Interactions," *St. Edmundsbury Press*, Bury St. Edmunds, Great Britain (1993), which is hereby incorporated by reference in its entirety). The most common domains associated with this function are the helix-turn-helix (HTH) motif, the Zn-binding domain or Zinc fingers, and the Leucine zipper coiled coil (b-ZIP) (Brunelle et al., "Transcription Regulatory Proteins in Higher Plants," *Current Opinions in Genetics and Development*, 3:254–258 (1993), which is hereby incorporated by reference in its entirety). Not all transcription regulators bind to DNA. Protein to protein interactions are responsible for the formation of heterodimers or homodimers, which in turn function as positive regulators, or as negative regulators, avoiding formation of active dimers. Synthesis or activation of these factors is induced by particular stimuli and, in some cases, involve phosphorylation cascades (Brunelle et al., "Transcription Regulatory Proteins in Higher Plants," *Current Opinions in Genetics and Development*, 3:254–258 (1993), which is hereby incorporated by reference in its entirety).

In the current model for transcription initiation, TBP binds to the TATA box through the minor groove of the DNA helix. TFIIA stabilizes the binding that can be debilitated by altered ionic conditions or mutations in the DNA binding element. TFIIB binds to TBP and orientates its amino terminal domain toward the downstream initiation site. This amino terminal sequence is not conserved among different species which suggests different regulatory pathways (Roeder, "The Role of Initiation Factors in Transcription by RNA polymerase II," *Trends in Biochemical Science*, 21:327–335 (1996), which is hereby incorporated by reference in its entirety). Also, plants like Arabidopsis can contain two different TBPs (Gasch et al., "*Arabidopsis Thaliana* Contains Two Genes for TFIID," *Nature*, 346: 390–394 (1990), which is hereby incorporated by reference in its entirety).

At the same time as TBP binds to the TATA box, TFIIF binds to RNA polymerase II to create a complex that then binds to the amino terminal domain of TFIIB, covering a promoter area of about 40 bp. Finally, TFIIE and TFIIH bind to the complex just upstream of the start site to induce promoter melting (opening of the double strand) and continue with transcription and elongation (Roeder, "The Role of Initiation Factors in Transcription by RNA Polymerase II," *Trends in Biochemical Science*, 21:327–335 (1996), which is hereby incorporated by reference).

One suitable DNA promoter molecule in accordance with the present invention has a nucleotide sequence of SEQ ID NO: 7 as follows:

CTGAGACCAGCGTTCAACATCGATGAAAATTTGTTTTAACAATGAGAACT

GCAAATCCTCCATAGTCTTCTAACATTTCAACATTCGAAATCTCGAAAAG

AAATTGGCTTGATATGATTTATTTAGGGTGTTAATTTTATGTATTATAAT

AATGCACAAATTGATATTTTATGCATCACATTTAATATTTTTAAAGTATA

TAATATCAAATCATTTTATGAAAATAAAAATACCAAATAATACATAAATT

GATAGTTCAAGTATTTCATTAAAAATTTTCAAAATATAAATATCATATTG

AAACATTTTATAAAAGAATAGATACCAAATATGACATCATCCCCTGTTGA

GAGTAACCAAACACTGTTTTCATCCAGCCCATGAGAAGTATTTGGCCCAA

AAGCAAAAGTTTCAGTACAATGAATTATGAATCCCAAAAAAACCCCAAGT

GGTCCAGGTCCAAGCCAGTCTAGGGCTGAGGAAAGAAATGGAAAAATTGA

AAAGTAATTCCAGGGTCTCATTCAATTTTATTAAATTTAGTTTGATTTTG

GTTTCGGTTCATAAATTTAAAAATAATTTTAAAATGTTATATAAAACTCT

TTTTTAAAAATAAATTAATCAATAATCTAAAACGATAAAAATGGCGATTT

GAATTAAGCTCATATTTTGAAAAAAAAATAAAAATTATCTCATCCAGAAC

TGATTAAAACCGAACCGATGAATCCTAGAAGCCAAGCCAAGTGTGCAGAG

TAAGAATAGAACATCAACATTTTGCTTTAAGCTTTTCGTTGCTTGCACTC

TAAGAAGCATAAAACGCAAGCAAAACTTGACACTAGTGTGAGTGTGAGTG

CCCATCATTCATCAACCCTGAAAATCGCCCTTCCCCTAATCAGTTCTAAC

CTCACTTTCTAACACTTTCACTGCAGCACTCAAAAACATTCGCCGAATCT

TTACTATAAACTCCCAGTGTTGGTTTCTCCACTCCAAACCCAAACCACGA

CCACCACATTTTGCTTCGTATCTTTGATA

This nucleotide sequence is 1.0 kb long (1,029 bp). Underlined are a TATAAA box for binding of RNA polymerase as well as a CAAT box enhancer element. Immediately following the nucleotide sequence is a candidate start sequence, ATGGA. Twelve bases following the candidate start sequence is another candidate start sequence, ATGGC.

Another suitable DNA promoter molecule in accordance with the present invention has a nucleotide sequence of SEQ ID NO: 8 as follows:

AACCTCTCGAGCTGCCATATTGGGTTTTTCACTACCCACCTCTTCATTAA

ATGTATCTTCAACCTCTCAACTCCTTTCACCACCAGACGAATCTTCTTTA

GCAAAATCAAAATGACCTTATGAAAATTTAGCACGTCCACCTCCAGATTC

AAAGGCTGTGAATCCCCAACTTCGGAAATTGTTCATCTCCACATTCAAGA

ATAATGAGTTCCTCAATTTGTTTTAACTGATTAGCCGATATTAAGCGAGT

TAGACTCCATGGAAATAAAATCACCCTAATAAATAGCAACGCTTTTGAAC

GTCTCTAGGTTCCAAGCGTGCTAAGGAGCGCCAGTAACTTCAATCCAAGT

TGTGCGAAAACGTATGAAATGGAACTGAGACCAGCGTTCAACATCGATGA

AAATTTGTTTTAACAATGAGAACTGCAAATCCTCCATAGTCTTCTAACAT

TTCAACATTCGAAATCTCGAAAAGAAATTGGCTTGATATGATTTATTTAG

GGTGTTAATTTTATGTATTATAATAATGCACAAATTGATATTTTATGCAT

CACATTTAATATTTTTAAAGTATATAATATCAAATCATTTTATGAAAATA

AAAATACCAAATAATACATAAATTGATAGTTCAAGTATTTCATTAAAAAT

TTTCAAAATATAAATATCATATTGAAACATTTTATAAAAGAATAGATACC

AAATATGACATCATCCCCTGTTGAGAGTAACCAAACACTGTTTTCATCCA

GCCCATGAGAAGTATTTGGCCCAAAAAGCAAAAGTTTCAGTACAATGAATT

ATGAATCCCAAAAAAACCCCAAGTGGTCCAGGTCCAAGCCAGTCTAGGGC

TGAGGAAAGAAATGGAAAAATTGAAAAGTAATTCCAGGGTCTGATTCAAT

TTTATTAAATTTAGTTTGATTTTGGTTTCGGTTCATAAATTTAAAAATAA

TTTTAAAATGTTATATAAAACTGTTTTTTAAAPATAAATTAATCAATAAT

CTAAAACGATAAAAATGGCGATTTGAATTAAGCTCATATTTTGAAAAAAA

AATAAAAATTATCTCATCCAGAACTGATTAAAACCGAACCGATGAATCCT

AGAAGCCAAGCCAAGTGTGCAGAGTAAGAATAGAACATCAACATTTTGCT

TTAAGCTTTTCGTTGCTTGCACTCTAAGAAGCATAAAACGCAAGCAAAAC

TTGACACTAGTGTGAGTGTGAGTGCCCATCATTCATCAACCCTGAAAATC

GCCCTTCCCCTAATCAGTTCTAACCTCACTTTCTAACACTTTCACTGCAG

CACTCAAAAACATTCGCCGAATCTTTACTATAAACTCCCAGTGTTGGTTT

CTCCACTCCAAACCCAAACCACGACCACCACATTTTGCTTCGTATCTTTG

ATA

This nucleotide sequence is 1.4 kb long (1,403 bp). Underlined are a TATAAA box for binding of RNA polymerase as well as a CAAT box enhancer element. Immediately following the nucleotide sequence is a candidate start sequence, ATGGA. Twelve bases following the candidate start sequence is another candidate start sequence, ATGGC.

Another suitable DNA promoter molecule in accordance with the present invention has a nucleotide sequence of SEQ ID NO: 9 as follows:

CTTCAATCTCTGCCAATGATCTCACCTTCTTCTTCACACCATCAACAGTA

ATTATCGTCGAATAGGGATTATGCACTACAGTGTTTTGCATTGCTACTCC

-continued

```
CATGGAGTCCTCCACCCTAACTCTACTTGTAGGACTCCTAACTAACGAAT
TGCAAAGGGTTTCGCGACCCGAATTGTTCCCTTTCTGACAACCCAAGTCC
ACTTAGGTTCAATCATATTTAAATTCGTATCAACAATCTCCTCAGCCGAC
CAATTCACAGCTTTCAAATCTGCTCCGCAACCCACCATTTGATCGTGACC
AAAGTGTGAACTTGCCTTCAACAAATCAGGCCCAGAGCCTCGTTCTAATC
ATTTCTCGAGGCAATAGCAATAGTTGGGTCTAAGTTCTCTGCTAATTCCT
TTGATTTCCTAGAACCTCTCGAGCTGCCATATTGGGTTTTTCACTACCCA
CCTCTTCATTAAATGTATCTTCAACCTCTCAACTCCTTTCACCACCAGAC
GAATCTTCTTTAGCAAAATCAAAATGACCTTATGAAAATTTAGCACGTCC
ACCTCCAGATTCAAAGGCTGTGAATCCCCAACTTCGGAAATTGTTCATCT
CCACATTCAAGAATAATGAGTTCCTCAATTTGTTTTAACTGATTAGCCGA
TATTAAGCGAGTTAGACTCCATGGAAATAAAATCACCCTAATAAATAGCA
ACGCTTTTGAACGTCTCTAGGTTCCAAGCGTGCTAAGGAGCGCCAGTAAC
TTCAATCCAAGTTGTGCGAAAACGTATGAAATGGAACTGAGACCAGCGTT
CAACATCGATGAAAATTTGTTTTAACAATGAGAACTGCAAATCCTCCATA
GTCTTCTAACATTTCAACATTCGAAATCTCGAAAAGAAATTGGCTTGATA
TGATTTATTTAGGGTGTTAATTTTATGTATTATAATAATGCACAAATTGA
TATTTTATGCATCACATTTAATATTTTTAAAGTATATAATATCAAATCAT
TTTATGAAAATAAAAATACCAAATAATACATAAATTGATAGTTCAAGTAT
TTCATTAAAAATTTTCAAAATATAAATATCATATTGAAACATTTTATAAA
AGAATAGATACCAAATATGACATCATCCCCTGTTGAGAGTAACCAAACAC
TGTTTTCATCCAGCCCATGAGAAGTATTTGGCCCAAAAGCAAAAGTTTCA
GTACAATGAATTATGAATCCCAAAAAAACCCCAAGTGGTCCAGGTCCAAG
CCAGTCTAGGGCTGAGGAAAGAAATGGAAAAATTGAAAAGTAATTCCAGG
GTCTGATTCAATTTTATTAAATTTAGTTTGATTTTGGTTTCGGTTCATAA
ATTTAAAAATAATTTTAAAATGTTATATAAAACTGTTTTTTAAAAATAAA
TTAATCAATAATCTAAAACGATAAAAATGGCGATTTGAATTAAGCTCATA
TTTTGAAAAAAAAATAAAAATTATCTCATCCAGAACTGATTAAAACCGAA
CCGATGAATCCTAGAAGCCAAGCCAAGTGTGCAGAGTAAGAATAGAACAT
CAACATTTTGCTTTAAGCTTTTCGTTGCTTGCACTCTAAGAAGCATAAAA
CGCAAGCAAAACTTGACACTAGTGTGAGTGTGAGTGCCCATCATTCATCA
ACCCTGAAAATCGCCCTTCCCCTAATCAGTTCTAACCTCACTTTCTAACA
CTTTCACTGCAGCACTCAAAAACATTCGCCGAATCTTTACTATAAACTCC
CAGTGTTGGTTTCTCCACTCCAAACCCAAACCACGACCACCACATTTTGC
TTCGTATCTTTGATA
```

This nucleotide sequence is 1.8 kb long (1,815 bp). Underlined are a TATAAA box for binding of RNA polymerase as well as a CAAT box enhancer element. Immediately following the nucleotide sequence is a candidate start sequence, ATGGA. Twelve bases following the candidate start sequence is another candidate start sequence, ATGGC.

Yet another suitable DNA promoter molecule in accordance with the present invention has a nucleotide sequence of SEQ ID NO: 10 as follows:

```
ATGAAACATCTTCGTACTCATATCTGAAACTCCAGCTTCTTGATCCTCAA
TGATAATTAAATCCTCACTATCACTCGCATTCACCTCGAGCAGCTTCGCA
AATTGAAATGTTTCCTTAGCTTCCTTCACTATACTTGCGATTCCCAATGA
CAGAGTCAGTAAGGGAACCATTAACAATACGATCATCCGTTCTTTGCTTC
TTCACCAGACACCACACCTTTAGATATGATTGGTTTTCTACCTCTACGTT
TTTGCTTCTTTTTTTTTTTAACCAAAGTCATCACTTTTTCTTCAATCTC
TGCCAATGATCTCACCTTCTTCTTCACACCATCAACAGTAATTATCGTCG
AATAGGGATTATGCACTACAGTGTTTTGCATTGCTACTCCCATGGAGTCC
TCCACCCTAACTCTACTTGTAGGACTCCTAACTAACGAATTGCAAAGGGT
TTCGCGACCCGAATTGTTCCCTTTCTGACAACCCAAGTCCACTTACGTTC
AATCATATTTAAATTCGTATCAACAATCTCCTCAGCCGACCAATTCACAG
CTTTCAAATCTGCTCCGCAACCCACCATTTGATCGTGACCAAAGTGTGAA
CTTGCCTTCAACAAATCAGGCCCAGAGCCTCGTTCTAATCATTTCTCGAG
GCAATAGCAATAGTTGGGTCTAAGTTCTCTGCTAATTCCTTTGATTTCCT
AGAACCTCTCGAGCTGCCATATTGGGTTTTTCACTACCCACCTCTTCATT
AAATGTATCTTCAACCTCTCAACTCCTTTCACCACCAGACGAATCTTCTT
TAGCAAAATCAAAATGACCTTATGAAAATTTAGCACGTCCACCTCCAGAT
TCAAAGGCTGTGAATCCCCAACTTCGGAAATTGTTCATCTCCACATTCAA
GAATAATGAGTTCCTCAATTTGTTTTAACTGATTAGCCGATATTAAGCGA
GTTAGACTCCATGGAAATAAAATCACCCTAATAAATAGCAACGCTTTTGA
ACGTCTCTAGGTTCCAAGCGTGCTAAGGAGCGCCAGTAACTTCAATCCAA
GTTGTGCGAAAACGTATGAAATGGAACTGAGACCAGCGTTCAACATCGAT
GAAAATTTGTTTTAACAATGAGAACTGCAAATCCTCCATAGTCTTCTAAC
ATTTCAACATTCGAAATCTCGAAAAGAAATTGGCTTGATATGATTTATTT
AGGGTGTTAATTTTATGTATTATAATAATGCACAAATTGATATTTTATGC
ATCACATTTAATATTTTTAAAGTATATAATATCAAATCATTTTATGAAAA
TAAAAATACCAAATAATACATAAATTGATAGTTCAAGTATTTCATTAAAA
ATTTTCAAAATATAAATATCATATTGAAACATTTTATAAAGAATAGATA
CCAAATATGACATCATCCCCTGTTGAGAGTAACCAAACACTGTTTTCATC
CAGCCCATGAGAAGTATTTGGCCCAAAAGCAAAAGTTTCAGTACAATGAA
TTATGAATCCCAAAAAAACCCCAAGTGGTCCAGGTCCAAGCCAGTCTAGG
GCTGAGGAAAGAAATGGAAAAATTGAAAAGTAATTCCAGGGTCTGATTCA
ATTTTATTAAATTTAGTTTGATTTTGGTTTCGGTTCATAAATTTAAAAAT
AATTTTAAAATGTTATATAAAACTGTTTTTTAAAAATAAATTAATCAATA
ATCTAAAACGATAAAAATGGCGATTTGAATTAAGCTCATATTTTGAAAAA
AAAATAAAAATTATCTCATCCAGAACTGATTAAAACCGAACCGATGAATC
CTAGAAGCCAAGCCAAGTGTGCAGAGTAAGAATAGAACATCAACATTTTG
CTTTAAGCTTTTCGTTGCTTGCACTCTAAGAAGCATAAAACGCAAGCAAA
```

-continued
ACTTGACACTAGTGTGAGTGTGAGTGCCCATCATTCATCAACCCTGAAAA

TCGCCCTTCCCCTAATCAGTTCTAACCTCACTTTCTAACACTTTCACTGC

AGCACTCAAAAACATTCGCCGAATCTTTAC<u>TATAAA</u>CTCCCAGTGTGTGG

TTTCTCCACTCCAAACCCAAACCACGACCACCACATTTTGCTTCGTATCT

TTGATA

This nucleotide sequence is 2.1 kb long (2,105 bp). Underlined are a TATAAA box for binding of RNA polymerase as well as a CAAT box enhancer element. Immediately following the nucleotide sequence is a candidate start sequence, ATGGA. Twelve bases following the candidate start sequence is another candidate start sequence, ATGGC.

In addition to the four above DNA promoter molecules, other promoter lengths that are either: (a) longer than but including SEQ ID NO: 10; or (b) any number of bases shorter than SEQ ID NO: 10 can be used for the present invention. It is also possible to create useful artificial nucleotide polymers containing key regulatory elements included within SEQ ID NO: 10 that are necessary and sufficient to drive gene expression as shown for the promoter having a nucleotide sequence of SEQ ID NO: 10 or any shorter fragment or to modify the demonstrated pattern of gene expression in other useful ways. For example, selected regulatory elements might be identified within SEQ ID NO: 10 and artificially fused to create a modified promoter that would then restrict gene expression to any one of the specific cell types in which the promoter is currently useful, for example only to the secondary wall stage of cotton lint fiber development. Similarly, particular regulatory motifs or domains could be identified for deletion to give more cell-type specificity to the promoter fragments described. It is well established that different combinations of regulatory motifs or domains within promoters direct expression of genes in different cell populations within a tissue (Capone et al., "Expression in Different Populations of Cells of the Root Meristem is Controlled by Different Domains of the rol B Promoter," Plant Mol. Biol., 25:681–691 (1994), which is hereby incorporated by reference in its entirety). "Motifs" or "domains" mean, respectively, shorter (e.g. typically 4–11) or longer (e.g. typically 12–300) sequences of nitrogenous bases in the promoter DNA that are binding sites or sites of other responses involving the complementary protein transcription factors or other regulatory factors that are part of the cellular and developmental control of transcription. Artificial manipulation of native promoters by fusion or deletion of motifs or domains to affect strength, specificity, and/or response to certain transcription factors is well known to those skilled in the art (Ohneda et al., "A Minigene Containing Four Discrete Cis Elements Recapitulates GATA-1 Gene Expression in vivo," Genes Cells, 7:1243–1254 (2002); Lee et al., "Transcriptional Regulation of Xbr-1a/X-vent 2 Homeobox Gene: Analysis of its Promoter Region," Biochem. Biophys. Res. Commun., 298: 815–823 (2002); Buzeli et al., "Tissue-Specific Regulation of BiP Genes: A Cis-Acting Regulatory Domain is Required for BiP Promoter Activity in Plant Meristems," Plant Mol. Biol., 50:757–71 (2002), which are hereby incorporated by reference in their entirety). As a particular example in the F286 promoter, it is possible that motif ACTTTA (#140 in Table 9), which is required for vascular expression of the rol B in tobacco (Baumann et al., "The DNA Binding Site of the Dof Protein NtBBF1 is Essential for Tissue-Specific and Auxin-Regulated Expression of the Rol B Oncogene in Plants," Plant Cell, 11:323–333 (1999), which is hereby incorporated by reference in its entirety), could be deleted or mutated to help restrict F286 promoter activity to lint fiber at the secondary wall stage of development. It is also possible that additional utility can be conferred to the F286 promoter or its artificial derivatives by inclusion in the gene expression construct of domains from the intron of the F286 gene or from the 3' untranslated end of the gene.

The isolated DNA promoter of the present invention can drive expression of operatively coupled DNA molecules in cotton fibers starting at the beginning of secondary wall deposition, usually 14 to 17 DPA, preferably extending through to the termination of secondary wall deposition. Most preferably, the isolated DNA promoter of the present invention drives expression of operatively coupled DNA molecule in cotton fibers beginning at 14 to 17 DPA up to 40 DPA. To identify promoters capable of preferential regulation in any selected cell type or stage of development, it is well known by one skilled in the art that one should look first for mRNAs that are preferentially transcribed in the desired manner. This greatly enhances the chances that the isolated promoter of the corresponding gene will drive foreign gene expression in the same manner once the promoter and the foreign gene are operably linked in a gene expression construct that is incorporated into the DNA of the host via transformation. A conserved pattern of promoter activity often occurs in heterologous species as well as the source species of the isolated promoter, but ultimately promoter performance must be determined by empirical testing.

Several techniques for identification of differentially expressed genes between two tissues, cell types, environmental conditions, and so forth are now standard in the art, assuming that living material representing the two states can be isolated and separated under reasonable conditions for RNA extraction and purification. Cotton fibers are ideally suited for this goal, both because they are long single cells that can be readily separated from the seed and because two important stages of fiber development, primary and secondary wall deposition, occur with only partial overlap in developmental time. These facts and methodological details appropriate for cotton are well shown by previous work to isolate genes with preferential expression and gene promoters capable of preferential promotion in cotton fibers (U.S. Pat. No. 5,474,925 to John et al; U.S. Pat. No. 5,521,078 to John, which are hereby incorporated by reference in their entirety). Such work also has a double purpose in that genes that are preferentially or differentially expressed in fiber compared to other cells and tissues or in distinct developmental stages of fiber will often be ones with critical roles in determining fiber development and the fiber attributes that translate to fiber quality for industrial use. Total RNA from the two states to be compared will contain different populations of mRNAs representing only the genes that are expressed in each state. The two populations of mRNAs (or their corresponding cDNAs after reverse transcription) can then be compared by any number of standard techniques including: (a) differential display of cDNAs; (b) differential screening of cDNA libraries; (c) comparing expressed sequence tags (ESTs) between two separately made cDNA libraries; (d) sequencing of ESTs from one subtracted cDNA library, where mRNA preferentially expressed in one tissue is enriched before making the cDNA library; (e) cDNA AFLP; (f) serial analysis of gene expression (SAGE); or (g) microarray analysis. The choice between these techniques in any particular case is now largely made according to convenience, custom and/or availability of necessary resources, and the necessary technical details are widely published (Hunt et al. (eds) "Functional Genomics," 253 pp Oxford University Press: Oxford (2000), which is hereby incorporated by reference in its entirety).

In most of these techniques, false positives are possible, so preferential expression of each gene of interest must be verified by standard techniques such as Northern blotting or RT-PCR, using isolated RNA from each state as the target for probes or primers based on the sequence of interest. Or, more efficiently, microarray analysis allows many candidate differentially expressed genes to be screened simultaneously with probes derived from RNA of the two states of interest. If the gene expression pattern is proved to be preferential in the expected pattern, it is reasonable to proceed with isolation of the promoter for direct testing of its utility in driving foreign gene expression in a genetically engineered cell or tissue (in the case of transient transformation) or organism (in the case of stable transformation). These techniques are standard in the art, including in cotton for which many detailed methods can be readily found (U.S. Pat. No. 5,474,925 to John et al; U.S. Pat. No. 5,521,078 to John, which are hereby incorporated by reference in their entirety).

Promoters of genes can be isolated from genomic DNA by several standard techniques including: (a) hybridization screening of a genomic library with a probe from a cDNA of interest and (b) PCR. These procedures are well known to those skilled in the art, and a suitable method can be easily chosen according to convenience or custom. There is no fixed rule about how much of the 5' sequence upstream of a coding sequence is necessary to drive the pattern of gene expression observed in vivo, and, indeed, there may be introns and/or 3' regulatory elements that also contribute to the in vivo expression pattern. However, it is common to first isolate and test a 1 to 3 kb sequence immediately 5' of the coding sequence for promoter activity. In addition, several lengths shorter than the maximum one are often tested to determine more minimal regions that will work in the desired manner. Such promoter deletion experiments are also a first approach to identifying key regulatory elements within a promoter, although such information is not always revealed until motifs bound by key transcription factors are directly identified by additional experimentation. There are also other approaches not mentioned that will yield similar results and information.

In a preferred form of the present invention, the isolated DNA promoter of the invention is in a DNA construct including the isolated DNA promoter, a second DNA encoding a protein or polypeptide. The DNA promoter is operably linked 5' to the second DNA to induce transcription of the second DNA. A 3' regulatory region is operably linked to the second DNA.

One form of protein-encoding DNA suitable for use in the DNA construct of the present invention is the isolated nucleic acid molecule of the invention, preferably, the nucleic acid molecule including a nucleotide sequence which hybridizes to a DNA molecule having a sequence according to SEQ ID NO: 1 or SEQ ID NO: 3 under stringent conditions characterized by a hybridization buffer comprising 1×SSC at a temperature of 61° C, having a nucleotide sequence of SEQ ID NO: 1 or SEQ ID NO: 3, encoding a protein or polypeptide including an amino acid sequence of SEQ ID NO: 5 or SEQ ID NO: 6 or an amino acid sequence having at least 60% identity to SEQ ID NO: 5 or an amino acid sequence having at least 75% identity to SEQ ID NO: 6, or encoding a protein or polypeptide having an amino acid sequence of SEQ ID NO: 2 or SEQ ID NO: 4.

Protein-encoding DNA suitable for use in the present invention includes DNA which has been amplified, chemically altered, or otherwise modified. Modification of such protein-encoding DNAs may occur, for example, by treating the DNA with a restriction enzyme to generate a DNA fragment which is capable of being operably linked to the promoter. Modification can also occur by techniques such as site-directed mutagenesis.

The protein-encoding DNA also includes DNA that is completely synthetic, semi-synthetic, or biologically derived, such as DNA derived by reverse transcription from RNA. Such DNA includes, but is not limited to, non-plant genes such as those from bacteria, yeasts, animals, or viruses; modified genes, portions of genes, chimeric genes, as well as DNA that encodes for amino acids that are chemical precursors or biologics of commercial value, such as polymers or biopolymers (Pool et al., "In Search of the Plastic Potato," *Science*, 245:1187–1189 (1989), which is hereby incorporated by reference in its entirety). Suitable DNA is any DNA for which expression is beneficial to the transgenic plant or for which it is otherwise beneficial to have the DNA expressed under control of a DNA promoter that drives expression preferentially during the secondary wall stage of fiber development.

A general goal of the fiber industry is to genetically engineer plants with improved fiber quality attributes and manipulable quality attributes, so that fibers might be specifically produced for different product end uses. This goal relates both to the traditional quality attributes of fiber, which may be changed by manipulating developmental or biochemical pathways already existing in the fiber, and to more novel qualities that may only be conferred through genetic engineering. For example, cotton fiber has traditional quality attributes of length, fiber diameter, maturity, strength, dyeability, and light green and brown color and potential novel attributes such as blue color or storage of novel enzymes or polymers, each with its on added value. Several of the traditional quality attributes of cotton fiber are largely or primarily dependent on the thick secondary wall and its cellulose content, specifically maturity, strength, and dyeability. Modem spinning technology and production of high quality textiles prefers fine (small diameter), long, strong, mature fibers (which implies higher strength and dyeability). Even fiber length and diameter are to some extent dependent on the time of initiation of the secondary wall, at which time elongation slows down and fiber diameter becomes more constrained. Because the secondary wall forms most (about 95% of the bulk of the mature fiber) and is the longest phase of fiber development, genetic engineering at this stage will be required to confer novel colors to cotton fibers or to store large quantities of desirable foreign molecules in the lumen or secondary wall.

Therefore, examples of other protein-encoding DNA molecules that could be expressed in the present invention include, but are not limited to, homologous and heterologous cellulose synthases (CesA genes), both in normal and mutated form (Arioli et al., "Molecular Analysis of Cellulose Biosynthesis in *Arabidopsis*," *Science*, 279:717–720 (1998); Holland et al., "A Comparative Analysis of the Plant Cellulose Synthase (CesA) Gene Family," *Plant Physiol.*, 123:1313–1324 (2000), which are hereby incorporated by reference in their entirety); genes that may modulate carbon partitioning to cellulose (Delmer, "Cellulose Biosynthesis in Developing Cotton Fibers" in: A. S. Basra (ed.), *Cotton Fibers: Developmental Biology, Quality Improvement, and*

*Textile Processing*, The Haworth Press, New York, pp. 85–112 (1999), which is hereby incorporated by reference in its entirety) such as sucrose synthase (Amor et al., "A Membrane-Associated Form of Sucrose Synthase and Its Potential Role Synthesis of Cellulose and Callose in Plants," *Proc. Natl. Acad. Sci. USA*, 92:9353–9357 (1995), which is hereby incorporated by reference in its entirety), sucrose phosphate synthase (Haigler et al., "Transgenic Cotton Over-Expressing Sucrose Phosphate Synthase Produces Higher Quality Fibers with Increased Cellulose Content and Has Enhanced Seed Cotton Yield" Abstract 477. In: Proceedings of Plant Biology, 2000, Jul. 15–19, San Diego, Calif. American Society of Plant Physiologists, Rockville, Md., (2000), which is hereby incorporated by reference in its entirety), UDPG-pyrophosphorylase (Waffler and Meier, "Enzyme Activities in Developing Cotton Fibers," *Plant Physiol. Biochem*. 32:697–702 (1994), which is hereby incorporated by reference in its entirety), inorganic pyrophosphatase (Geigenberger et al., "Overexpression of Pyrophosphatase Leads to Increased Sucrose Degradation and Starch Synthesis, Increased Activities of Enzymes for Sucrose-Starch Interconversions, and Increased Levels of Nucleotides in Growing Potato Tubers," *Planta*, 205:428–437(1998), which is hereby incorporated by reference in its entirety), hexokinases (Smeekens, "Sugar Regulation of Gene Expression," *Curr. Op. Plant Biol*; 1:230–234 (1998), which is hereby incorporated by reference in its entirety), and invertases (Sturm and Tang, "The Sucrose-Cleaving Enzymes of Plants are Crucial for Development, Growth, and Carbon Partitioning," *Trends Plant Sci*., 4:401–407 (1999), which is hereby incorporated by reference in its entirety); genes that might affect the molecular and biophysical properties of cellulose including degree of polymerization, degree of crystallinity, crystallite size, and microfibril orientation (i.e. genes for encoding proteins, including co-crystallizing protein polymers or cellulose binding domains, and polysaccharide-synthesizing and other enzymes) (Delmer, "Cellulose Biosynthesis: Exciting Times for a Difficult Field of Study," *Ann. Rev. Plant Physiol. Mol. Biol*. 50:245–276 (1999); Delmer, "Cellulose Biosynthesis in Developing Cotton Fibers. In: A. S. Basra (ed.), *Cotton Fibers: Developmental Biology, Quality Improvement, and Textile Processing*, The Haworth Press, New York, pp. 85–112 (1999); Hsieh, "Structural Development of Cotton Fibers. In: A. S. Basra (ed.), *Cotton Fibers: Developmental Biology, Quality Improvement, and Textile Processing*, The Haworth Press, New York, pp. 137–166 (1999), which are hereby incorporated by reference in their entirety); transcription factors such as MYB genes that could prolong elongation growth and/or change the timing or extent of secondary wall deposition (Wilkins and Jemstedt, "Molecular Genetics of Developing Cotton Fibers. In: A. S. Basra (ed.), *Cotton Fibers: Developmental Biology, Quality Improvement, and Textile Processing*, The Haworth Press, New York, pp. 231–270 (1999), which is hereby incorporated by reference in its entirety); genes to effect the synthesis of plant hormones and change fiber properties (John, "Genetic Engineering Strategies for Cotton Fiber Modification. In: A. S. Basra (ed.), *Cotton Fibers: Developmental Biology, Quality Improvement, and Textile Processing*, The Haworth Press, New York, pp. 271–289 (1999), which is hereby incorporated by reference in its entirety); genes for cytoskeletal elements or cytoskeletal-associated proteins that might affect fiber properties (Seagull, "Cytoskeletal Involvement in Cotton Fiber Growth and Development," *Micron*, 24:643–660 (1993), which is hereby incorporated by reference in its entirety); genes for lipid synthesizing or modifying enzymes that might change membrane properties and thereby improve fiber quality, including under stressful environmental conditions (Haigler, "The Crystallinity of Cotton Cellulose in Relation to Cotton Improvement," *Proc. Cotton Fiber Cellulose: Structure, Function, and Utilization Conference*, National Cotton Council of America: Memphis, Tenn., p. 211–225 (1992), which is hereby incorporated by reference in its entirety); enzymes such as xyloglucan endotransferase, peroxidase, expansin, or vacuolar ATPase that might, through increased or decreased activity, prolong or increase extension growth during secondary wall deposition (Wilkins and Jemstedt, "Molecular Genetics of Developing Cotton Fibers. In: A. S. Basra (ed.), *Cotton Fibers: Developmental Biology, Quality Improvement, and Textile Processing*, The Haworth Press, New York, pp. 231–270 (1999), which is hereby incorporated by reference in its entirety); genes for protein or plastic polymers that might be retained in the fiber lumen or integrated into the cell wall to increase fiber strength or change its textile properties (John, "Genetic Engineering Strategies for Cotton Fiber Modification," In: A. S. Basra (ed.), *Cotton Fibers: Developmental Biology, Quality Improvement, and Textile Processing*, The Haworth Press, New York, pp. 271–289 (1999); Guda et al., "Hyperexpression of an Environmentally Friendly Synthetic Polymer Gene," *Biotechnology Letters*, 17:745–750 (1995), which are hereby incorporated by reference in their entirety); genes for plant cell wall matrix biosynthetic enzymes or their regulatory proteins so that other carbohydrates could be integrated into the cell wall and change fiber properties (Haigler, "The Relationship Between Polymerization and Crystallization in Cellulose Biogenesis," in C. H. Haigler and P. Weimer, eds., *Biosynthesis and Biodegradation of Cellulose*, New York: Marcel Dekker, pp. 99–124 (1991); Andrawis et al., "Cotton Fiber Annexins: A Potential Role in the Regulation of Callose Synthase," *Plant J*., 3: 763–772 (1993), which are hereby incorporated by reference in their entirety); genes for molecules such as tannins, suberins, or dyes that might confer valuable color to fibers (Ryser, "Cotton Fiber Initiation and Histodifferentiation," In: A. S. Basra (ed.), *Cotton Fibers: Developmental Biology, Quality Improvement, and Textile Processing*, The Haworth Press, New York, pp. 1–46 (1999), which is hereby incorporated by reference in its entirety); genes for molecules such as cutin, suberin, or wax that might change the absorptivity and strength of cotton fibers (May, "Genetic Variation in Fiber Quality," In: A. S. Basra (ed.), *Cotton Fibers: Developmental Biology, Quality Improvement, and Textile Processing*, The Haworth Press, New York, pp. 183–230 (1999); Ryser, "Cotton Fiber Initiation and Histodifferentiation," In: A. S. Basra (ed.), *Cotton Fibers: Developmental Biology, Quality Improvement, and Textile Processing*, The Haworth Press, New York, pp. 1–46 (1999), which are hereby incorporated by reference in their entirety); and genes for signal transduction molecules such as Rac that may regulate shifts between fiber developmental stages (Delmer et al., "Genes Encoding Small GTP-Binding Proteins Analogous to Mammalian rac are Preferentially Expressed in Developing Cotton Fibers," *Mol. Gen. Genet.*, 248: 43–51 (1995), which is hereby incorporated by reference in its entirety).

Examples already exist for manipulation of several classes of these genes in transgenic plants with effects on cellulose content and/or fiber quality. Any of these strategies or analogous or similar ones might be advantageously applied to cotton fiber, particularly its secondary wall phase of development in a preferential manner. For example, cellulose content has been manipulated positively and negatively and cellulose crystallinity has been changed in the model plant *Arabidopsis* by manipulation of expression level and/or mutation of a cellulose synthase (U.S. Pat. No. 6,495,740 to Arioli et al., which is hereby incorporated by reference in its entirety). This work also provides an example of manipulation of carbohydrate partitioning as a secondary effect of changed cellulose content and/or characteristics, since in some cases starch accumulates preferentially. Sucrose synthase has also been manipulated to improve cellulose content in the stalks of maize, which have high fiber content (U.S. Patent Application Publication No. 20030005482 to Dhuuga et al., which is hereby incorporated by reference in its entirety). In addition, sucrose phosphate synthase under the control of the CaMV 35S promoter has been manipulated to improve fiber quality in transgenic cotton (U.S. Pat. No. 6,472,588 to Haigler et al., which is hereby incorporated by reference in its entirety), and further advantage might be gained by restricting the genetic change to the secondary wall phase of fiber development. Cotton fiber quality has also been changed by manipulating the synthesis of the growth hormone, cytokinin (U.S. Pat. No. 6,329,570 to Martineau, which is hereby incorporated by reference in its entirety). In addition, enzymes and cellulose binding proteins have been accumulated in the fiber lumen and cell wall (U.S. Pat. No. 5,474,925 to John et al., which is hereby incorporated by reference in its entirety). Further, a thermoplastic polymer has been accumulated in the cotton fiber lumen with advantageous effects on cotton textile properties (John, "Genetic Engineering Strategies for Cotton Fiber Modification,"In: A. S. Basra (ed.), Cotton Fibers: Developmental Biology, Quality Improvement, and Textile Processing, The Haworth Press, New York, pp. 271–289 (1999), which is hereby incorporated by reference in its entirety). In addition, endo-β-1,4-glucanase (a cellulase) and cellulose binding domains targeted to the cell wall have been shown to increase fiber mass, cellulose content, and plant growth rate, yield, and digestibility in other plants (U.S. Pat. No. 6,323,023 to Shoseyov et al.; U.S. Pat. No. 6,184,440 to Obed et al., which are hereby incorporated by reference in their entirety). Peroxidase capable of cross-linking cell wall proteins has also been shown to increase cotton fiber strength (U.S. Pat. No. 5,869,720 to John, which is hereby incorporated by reference in its entirety). Color has been manipulated in transgenic plants (U.S. Pat. No. 6,222,097 to McBride et al., which is hereby incorporated by reference in its entirety). Thus, although some might have advantageous effects at the primary wall stage of development, many such changes would likely make advantageous use of the present invention by targeting the genetically engineered change to the secondary wall phase of fiber development which affects the industrial uses of fibers to a great extent. The above list is illustrative rather than limiting, being included here only to illustrate the feasibility of using the present invention in many useful strategies that would benefit by targeting genetic changes to the secondary wall phase of fiber development.

The DNA construct of the present invention also includes an operable 3' regulatory region, selected from among those which are capable of providing correct transcription termination and polyadenylation of mRNA for expression in plant cells, operably linked to the a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Natl Acad. Sci. USA*, 80:4803–4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature*, 313(6005):810–812 (1985), which is hereby incorporated by reference in its entirety). Virtually any 3' regulatory region known to be operable in plants would suffice for proper expression of the coding sequence of the DNA construct of the present invention.

The protein-encoding DNA molecule, the promoter of the present invention, and a 3' regulatory region can be ligated together using well known molecular cloning techniques as described in Sambrook et al., Molecular *Cloning: A Laboratory Manual*, Second Edition, Cold Spring Harbor Press, NY (1989), which is hereby incorporated by reference in its entirety.

In another embodiment, the present invention is an expression system that includes a suitable vector containing the above DNA construct of the invention. The present invention also includes host cells which include the DNA construct of the invention described above, transgenic plants and seeds produced by transformation with the DNA construct.

The present invention also relates to a method of expressing a gene preferentially in secondary walled cells during secondary wall deposition in a plant involving transforming a plant with the DNA construct including the isolated DNA promoter of the present invention. Typically, the secondary walled cells are fiber. The DNA construct of the present invention can be utilized to express a gene during the secondary wall deposition in a wide variety of fiber-producing plants such as trees, forage crops, cotton, corn, sugar cane, and rice stems that can be used in pulping, flax, hemp, ramie, jute, kenaf, kapok, coir, bamboo, spanish moss, abaca, and *Agave* spp. (e.g. sisal). The DNA construct is particularly well suited to expressing a gene during the secondary wall deposition in cotton. Basically, this method is carried out by transforming a plant cell with a DNA construct of the present invention, as described above, under conditions effective to yield transcription of the DNA molecule in response to the promoter. Methods of transformation may result in transient or stable expression of the DNA under control of the promoter. Preferably, the DNA construct of the present invention is stably inserted into the genome of the recombinant plant cell as a result of the transformation, although transient expression can serve an important purpose, particularly when the plant under investigation is slow-growing.

The gene fusion system that generates chimeric molecules is a very powerful tool to study promoter activity. However, although many transformation and regeneration protocols have been developed for plants, it still takes at least 3 months (in the case of tobacco) or as long as 6–12 months (in the case of cotton) to obtain stable transformant plants that can be evaluated. Even then, more time is required to evaluate expression in tissues like flowers or fruits. As an alternative methodology, transient expression in tissue or protoplasts offers a fast and often reliable way to generate information before proceeding with stable transformation. In addition, this method circumvents possible negative "position effects" due to the insertion of the introduced DNA into non-expressing regions of the chromosome.

EXAMPLES

The following examples are provided to illustrate embodiments of the present invention but are by no means intended to limit its scope.

Example 1

Identification of F285, a cDNA Clone Preferentially Expressed in Fibers During Secondary Wall Deposition Differential display as described in Liang et al., "Differential Display of Eukaryotic DNA by Means of the Polymerase Chain Reaction," *Science*, 257: 967–970 (1992), which is hereby incorporated by reference in its entirety, was used to identify a gene that was differentially expressed in secondary wall stage cotton fibers. The technique has the following steps: (a) two or more different total RNA populations are reverse transcribed in the presence of an anchored oligo dT (e.g. $dT_{12}$-XY, where X and Y denote A, C, G, or T, disallowing TT) to yield cDNA fragments of an mRNA subpopulation; (b) cDNA fragments are amplified by PCR in the presence of the same anchored oligo dT, an arbitrary sequence 10 mer oligonucleotide, and $^{35}$S- or $^{33}$P-dATP+ dNTPs; and (c) amplified cDNA fragments are separated on non-denaturing sequencing gels by size and detected on film by autoradiography. cDNAs that are differentially present are identified by comparison between gel lanes, excised from gels, reamplified by PCR, cloned, and analyzed by sequencing and Northern blotting analyses.

For the results described here, $d(T)_{12}$-GA was used as the anchored primer and GTCCTGGGTT (SEQ ID NO: 11) as the random 10-mer (called W17), which was purchased in a 10 mer kit from Operon Technologies (Almeda, Calif.). Total RNA was isolated from tissues of *Gossypium hirsutum* cv. Coker 312, as described in Wilkins et al., "Isolation of RNA from Plant Tissue. In: Krieg (eds) A Laboratory Guide to RNA: Isolation, Analysis, and Synthesis," p 21–40, Wiley Liss, N.Y. (1996), which is hereby incorporated by reference in its entirety, specifically 12 and 18 DPA cotton fibers, as well as ovules stripped of fiber and separated fiber at several other ages. Differential display was performed as described in Song et al., "Improved Procedures for Differential Display of Transcripts from Cotton Tissues," *Plant Mol. Biol. Rep.*, 13: 174–181 (1995), which is hereby incorporated by reference in its entirety, except that 2.5 µl M-MuLV reverse transcriptase was used and $^{35}$S was used as the radiolabel. Differential display gels were also run long enough so that only cDNAs $\geq$300 bp were retained, which avoided most cDNAs from untranslated regions.

Figure 1:
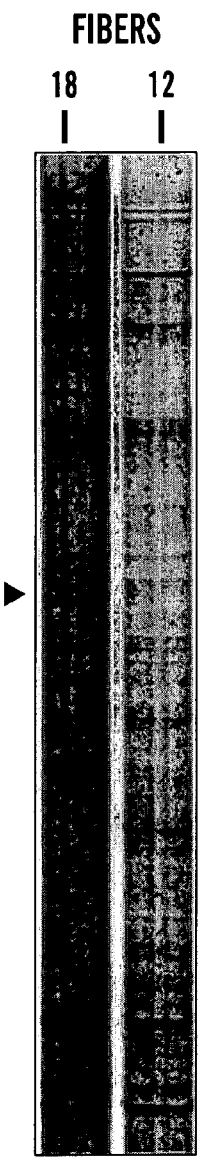
FIG. 1 is an autoradiographic image on film of a gel of labeled cDNA fragments arising through the technique of differential display from RNA isolated from 18 and 12 DPA cotton fibers, respectively, of *Gossypium hirsutum* cv. Coker 312. The arrow points to the band unique to 18 DPA cotton fibers that corresponds to the gene subsequently named F285 and shown to have homology to chitinases.

The 18 DPA-specific cDNA (FIG. 1) was cloned, using the TA cloning kit (InVitrogen Inc., Carlsbad, Calif.), sequenced, and used for Northern hybridization, as described later in Example 2. Partial sequencing showed that the cDNA had homology to known chitinases. Subsequent work to identify the full length cDNA (which was named F285; see Example 3), showed that the 10 mer (W17) matched GTCCCGGGGTT$_{746}$ (nucleotides 736–746 of SEQ ID NO: 1), but the primer had a nucleotide mismatch and a single nucleotide deletion, both of which occur at its 5' end. These results are consistent with other reports that 10 mer primers are more tolerant to mispairing at the 5' end (Bauer et al., "Identification of Differentially Expressed mRNA Species by an Improved Differential Display Procedure (DDRT-PCR)," *Nucleic Acids Res.*, 21: 4272–4280 (1993); Liang et al., "Differential Display and Cloning of Messenger RNAs from Human Breast Cancer Versus Mammary Epithelial Cells," *Cancer Res.*, 52: 6966–6968 (1992), which are hereby incorporated by reference in their entirety)

Example 2

Expression of F285 in Fibers During Secondary Wall Deposition

Northern blot analysis was performed on total RNA extracted from various tissues of greenhouse-grown *Gossypium hirsutum* cv. Coker 312 (natural light and ca. 32° C. day/22° C. night temperature). Total RNA (15 µg/lane) was loaded on a 1.2% agarose gel, electrophoresed, transferred to nitrocellulose membrane, heat fixed (1.5 h; 80° C.), and hybridized with $^{32}$P-labeled F285 probe (65° C., overnight). The membrane was washed (0.1×SSC, 0.1% SDS, 65° C., 15 min), and the film was exposed to autoradiography film (17 h; −80° C.). The same blot was stripped and reprobed with $^{32}$P-labeled 18S ribosomal RNA probe as control.

Figure 2:
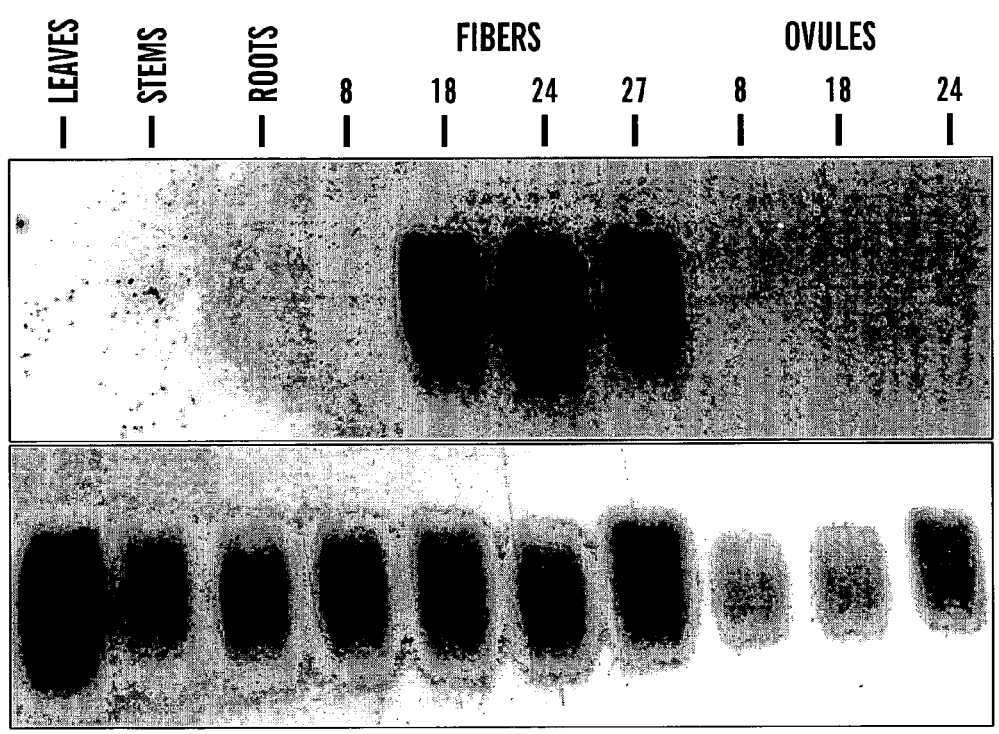
FIG. 2 shows a Northern blot exposed to film overnight showing total RNA isolated from various cotton tissues. The top frame shows incubation with a probe to F285, and the bottom frame shows incubation with a probe to 18S RNA to show the comparative level of RNA loading in each lane, which was intended to be 15 μg/lane.

The Northern blots indicated that the gene F285 is expressed in greenhouse-grown fibers only at the secondary wall stage at 18, 24, and 27 DPA (FIG. 2). There was no evidence of expression in fibers during primary wall deposition at 8 DPA, or in leaves, stems, roots, or ovules stripped of fiber at 8, 18, and 24 DPA. (The data from stripped ovules at 8 and 18 DPA were not as good because of the lower level of RNA loading. However, any strong expression similar to that shown for 18, 24, and 27 DPA fiber would have been apparent even with the lower loading.)

Figure 3:
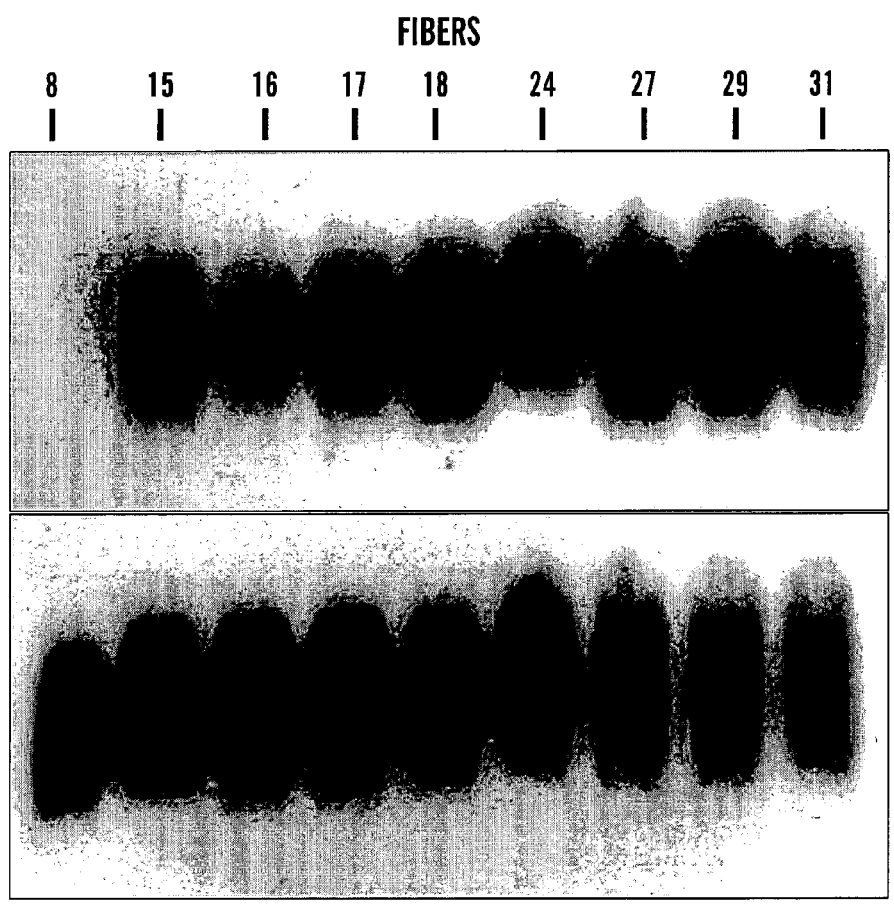
FIG. 3 shows a Northern blot, illustrating a more detailed time-course of fiber development. The top frame shows incubation with a probe to F285, and the bottom frame shows incubation with a probe to 18S RNA to show the comparative level of RNA loading in each lane.

More detailed temporal analysis indicated that expression in greenhouse-grown fiber had not begun by 12 DPA, but was strong by 15 DPA and remained strong through 31 DPA (FIG. 3). Therefore, the transcription of F285 initiated at 13–15 DPA, which is near the onset of secondary wall deposition in cotton fiber when cotton plants are grown under greenhouse conditions (approximately 32° C. day/22° C. night).

Example 3

Sequencing of F285 and Comparison of its Translated Amino Acid Sequence to Other Proteins Based on the sequence of the F285 cDNA, a 31-mer oligonucleotide primer just before the polyT tail was synthesized (5' CAATGGCTATATGTGACTCATTCAATCA-CAC; SEQ ID NO: 12) and used together with the SK primer (CGCTCTAGAACTAGTGGATC: SEQ ID NO: 13) in PCR screening of a UniZAP-XR cDNA library from mRNAs of 21 DPA Acala-SJ2 cotton fibers (Stratagene, La Jolla, Calif.; kindly provided by Dr. D. P. Delmer). The PCR reaction constituted 5 µl of boiled library lysate as template, 1 µM of each primer, 200 µM of each dNTP, 200 µM $MgCl_2$, and 0.5 U Taq polymerase. The PCR reaction conditions were: 34 cycles of 95° C. (30 min), 55° C. (1 min), and 72° C. (2 min), followed by extension at 72° C. (5 min). The PCR products were gel-purified, cloned into the TA cloning vector (InVitrogen, Carlsbad, Calif.), and completely sequenced on both strands. Analysis of the generated 1273 bp-length cDNA revealed a single open reading frame with 957 bp, which was named F285 (SEQ ID NO: 1).

The deduced amino acid sequence of 318 residues (SEQ ID NO: 2) had a predicted pI of 7.98 and a predicted molecular weight of 35,246 Da. The translated protein had a diverse mix of amino acids, a predicted N-terminal signal sequence, and sites for post-translational modification by: N-glycosylation, phosphorylation by four different types of protein kinases; amidation; and N-myristoylation. The F285 protein had a mix of hydrophilic and hydrophobic regions, extensive regions of alpha helix, extended strand, and random coil, and no predicted transmembrane alpha helices.

BLASTX searches that translated the F285 nucleotide sequence in all possible reading frames and checked for reference in its entirety), the comparative distance between these four sequences is the first indication that F285 and its *Arabidopsis* homolog represent a new type of chitinase-related protein.

TABLE 1

Results from CLUSTAL W multiple sequence alignment and BLASTX data

| | CLUSTAL W amino acid comparisons | | | | BLASTX data | |
|---|---|---|---|---|---|---|
| | | Strongly | Weakly | | | |
| F285 (318 aa) compared to: | Identical | Similar | Similar | Different | Score | E |
| Best Match, *Arabidopsis*/BAA94976.1 (333 aa) | 76.28% | 9.91% | 3.60% | 10.21% | 542 | e–153 |
| Closest other genus, *Arabis microphyllal* AAF69789.1 (299 aa; partial sequence) | 35.22% | 19.18% | 11.01% | 34.59% | 212 | 6e–54 |
| Closest cotton, *Gossypium hirsutum*/Q39799 (338 aa) | 31.66% | 20.12% | 11.54% | 36.69% | 196 | 4e–49 | homology with other amino acid sequences showed homology with numerous chitinases. A BLASTX search confirmed that there were only two close homologs of F285 that were discovered through sequencing of the *Arabidopsis thaliana* genome, one on chromosome 3 (BAA94976.1; 76.28% amino acid identity to F285) and one on chromosome 1 (AAF29391.1, also named AAL37737; 67.49% amino acid identity to F285). Hereafter, these are referred to as the *Arabidopsis* homologs of F285. The next closest match was to a chitinase from *Arabis microphylla* (AAF69789. 1; 35.22% amino acid identity to F285) (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety). The BLAST search also confirmed that F285 was similar to but distinct from full-length or nearly full-length cotton chitinases (Q39799, Q39785, AAD11255, and S72528, where the first three sequences listed are very closely related) in the databases (see TABLE 1). A BLASTP search with the F285 translated amino acid sequence did not reveal any additional highly similar sequences, except that another *Arabis* sequence closely related to AAF69789.1 (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety) was placed as the third highest match.

The amino acid sequences of BAA94976.1, AAF69789.1, and Q39799 were subjected individually to CLUSTAL W multiple sequence alignment with the F285 amino acid sequence to compare the identity, similarity, or difference of amino acids at each position (TABLE 1). F285 is much more similar to its *Arabidopsis* homolog (BLAST score 542; 76.28% identical amino acids) than to the chitinase from *Arabis* (BLAST score 212; 35.22% identical amino acids) or cotton (BLAST score 196; 31.66% identical amino acids). Since the genus *Arabis* contains the nearest relatives of *Arabidopsis thaliana* (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by F285 has homology with chitinases in regions corresponding to the active site (within 0.6 nm of bound substrate; Brameld et al., "The Role of Enzyme Distortion in the Single Displacement Mechanism of Family 19 Chitinases," *Proc. Nat'l. Acad. Sci. U.S.A.*, 95:4276–4281 (1998), which is hereby incorporated by reference in its entirety), including at a site (near NYNY) that is important for chitin binding in many chitinases (Verburg et al., "Identification of an Essential Tyrosine Residue in the Catalytic Site of a Chitinase Isolated From *Zea mays* That is Selectively Modified During Inactivation With 1-ethyl-3-(3-dimethylaminopropyl)-carbodiimide," *J. Biol. Chem.*, 267:3886–3893 (1992); Hamel et al., "Structural and Evolutionary Relationships Among Chitinases of Flowering Plants," *J. Mol. Evol.*, 44:614–624 (1997); Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which are hereby incorporated by reference in their entirety; TABLE 2). Chitin is a structural polysaccharide, a homopolymer of β-1,4-linked N-acetyl glucosamine, that is found in the exoskeletons of insects and the cell wall of fungi (Hamel et al., "Structural and Evolutionary Relationships Among Chitinases of Flowering Plants," *J. Mol. Evol.*, 44:614–624 (1997), which is hereby incorporated by reference in its entirety). However, here 'chitin binding' refers to binding of the enzyme with the short stretches (probably 3–6 sugars) of N-acetyl-glucosamine residues that interact with the enzyme during chitin hydrolysis (Robertus et al., "The Structure and Action of Chitinases," in Jolles, eds., *Chitin and Chitinases*, Birkäuser Verlag:Basel, pp. 125–136 (1999), which is hereby incorporated by reference in its entirety). Therefore, an enzyme with similar active site topology could bind with N-acetyl-glucosamine oligomers found in other molecules or in isolation. Also, it could interact with other molecules containing N-acetyl-glucosamine within heteropolymers or glycoproteins. As an example, some chitinases have lysozyme activity (Sahai et al., "Chitinases of Fungi and Plants: Their Involvement in Morphogenesis and Host-Parasite Interaction," *FEMS Microbiol. Rev.*, 11:317–338 (1993), which is hereby incorporated by reference in its entirety), meaning the ability to degrade bacterial peptidoglycan, which contains a heteropolymer of N-acetylglucosamine and N-acetylmuramic acid.

expected to be secreted outside the plasma membrane. Its myristoylation site also confers potential for acylation by the covalent addition of myristate (a C14-saturated fatty acid),

TABLE 2

Comparison between F285 and other related sequences

```
        159                                                      217
F285 TYPCTPGVSYHGRGALPIYW NYNY GETGDALKVDLLNHPEYIENNATLAFQAALWRWMT
Com1 ................+.......+..+........+....+...........+.....  (SEQ ID NO: 14)
Com2 .+..+..KR.+...++Q+S......LC.R.+G.....+.+L+A.+.++..+..+.F...  (SEQ ID NO: 15)
Com3 +...+..K+.+...++Q+S......+C.R.++.....+.+L+++++.++.++.+.F...  (SEQ ID NO: 16)
                 * * *
```

Com1: Comparison between F285 (amino acid number 159–217 of SEQ ID NO: 2) and its closest *Arabidopsis thaliana* homolog (BAA94976; SEQ ID NO: 14), which it matches best among similar proteins revealed by BLASTX search.
Com2: Comparison between F285 and an *Arabis microphylla* chitinase (AAF69789; SEQ ID NO: 15). This is the closest match found in a species other than *Arabidopsis* and the third best match revealed by BLASTX search.
Com3: Comparison between F285 and the *Gossypium hirsutum* (cotton) chitinase (Q39799; SEQ ID NO: 16), which it matches best among all cotton chitinases revealed by BLASTX search. This is the thirty seventh best match revealed.
Symbols:
dot(.): sites of identical amino acids between sequences
plus (+): sites of substitution of weakly or strongly similar amino acids
letters in Com1–Com3: single letter codes for dissimilar amino acids substituted at that position, which defines a 'different' substitution—see TABLE 3.
underlines in Com3: regions in the active site of authentic chitinases
asterisks (*) in Com3: residues proven by mutagenesis to be critical for function in authentic chitinases (Verburg et al., "Identification of an Essential Tyrosine Residue in the Catalytic Site of a Chitinase Isolated From *Zea mays* That is Selectively Modified During Inactivation With 1-ethyl-3-(3-dimethylaminopropyl)-carbodiimide," J. Biol. Chem., 267:3886–3893 (1992); Bishop et al., "Rapid Evolution in Plant Chitinases: Molecular Targets of Selection in Plant-Pathogen Coevolution, Proc. Nat'l. Acad. Sci. U.S.A., 97:5322–5327 (2000), which are hereby incorporated by reference in their entirety)

The *Arabis* protein listed in TABLES 1 and 2 is homologous to *Arabidopsis* class I chitinase, which has proven chitinolytic activity and defensive activity against fungi (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety). However, no function has been proven for F285 or its *Arabidopsis* homologs. After appearing in the database as part of the completely-sequenced *Arabidopsis* genome, the *Arabidopsis* homologs of F285 were categorized with chitinases in Family 19 of glycosyl hydrolases (CAZy, Carbohydrate-Active Enzymes; http://afmb.cnrs-mrs.fr/CAZY/index.html, which is hereby incorporated by reference in its entirety). Enzymes in Family 19 are expected to hydrolyze chitooligosaccharides with inversion of anomeric configuration (Henrissat, "Classification of Chitinase Modules," in Jolles, eds., *Chitin and Chitinases*, Basel:Birkhäuser Verlag, pp. 137–156 (1999), which is hereby incorporated by reference in its entirety). However, in the context of overall similarity to chitinases, specific differences in functional domains can be identified between F285 and its two *Arabidopsis* homologs vs. authentic chitinases. For example, F285 and its *Arabidopsis* homologs lack features that are typical of some, but not all, chitinases: (a) a cysteine-rich N-terminal chitin binding domain that would facilitate interaction with chitin; (b) a P (proline)/T (threonine)-rich hinge region before the catalytic region; and (c) a C-terminal vacuolar targeting domain (Meins et al., "The Primary Structure of Plant Pathogenesis-Related Glucanohydrolases and Their Genes," in Boller, eds., *Genes Involved in Plant Defense*, Springer Verlag/New York., p. 245–282 (1992), which is hereby incorporated by reference in its entirety). In the absence of the vacuolar targetting domain, F285 is which could facilitate reversible interaction with the plasma membrane (Thompson et al., "Lipid-Linked Proteins of Plants," *Prog. Lipid Res.*, 39:19–39 (2000), which is hereby incorporated by reference in its entirety).

In addition, F285 and its *Arabidopsis* homologs have non-conservative amino acid substitutions (i.e. with a different or dissimilar chemical type of amino acid) in regions proved by mutagenesis to be critical for the function of typical chitinases (Iseli-Gamboni et al., "Mutation of Either of Two Essential Glutamates Converts the Catalytic Domain of Tobacco Class I Chitinase Into a Chitin-Binding Lectin," *Plant Sci.*, 134:45–51 (1998), which is hereby incorporated by reference in its entirety and references therein) and in other regions predicted by crystal structure to be important for catalysis, active site geometry, or substrate binding (Hart et al., "The Refined Crystal Structure of an Endochitinase From *Hordeum vulgare* L. Seeds at 1.8 A Resolution," *J. Mol. Biol.*, 248:402–413 (1995); Hamel et al., "Structural and Evolutionary Relationships Among Chitinases of Flowering Plants," *J. Mol. Evol.*, 44:614–624 (1997); Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which are hereby incorporated by reference in their entirety). For example, of eleven amino acids in an *Arabis* chitinase that are putative substrate binding sites (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety), two are unchanged, three are substituted with similar amino acids, and six are substituted with dissimilar amino acids in F285. This suggests that F285, while related to chitinases, might have unique protein structure allowing a unique cellular role. Some of these non-conservative changes and, conversely, amino acids that were retained as expected for chitinases in the sequences of F285 and its *Arabidopsis* homologs, are summarized in TABLE 3 (compiled from Hamel et al., "Structural and Evolutionary Relationships Among Chitinases of Flowering Plants," *J. Mol. Evol.*, 44:614–624 (1997); Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which are hereby incorporated by reference in their entirety). Amino acids with asterisks (*) have been proven by mutagenesis to be important for the function of authentic chitinases (Iseli-Gamboni et al., "Mutation of Either of Two Essential Glutamates Converts the Catalytic Domain of Tobacco Class I Chitinase Into a Chitin-Binding Lectin," *Plant Sci.*, 134:45–51 (1998), which is hereby incorporated by reference in its entirety and references therein). The sequence of an *Arabis* chitinase has been used for the reference amino acid number system because of its prior annotation in the literature (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety). When amino acid substitutions are shown, the same ones were found at that position in F285 and its *Arabidopsis* homologs, except for an exception for AAF29391.1 as noted in the footnotes. 'Type of substitution' is as defined in the CLUSTAL W multiple sequence alignment program.

TABLE 3

Comparison of functional amino acids in chitinases to the F285 protein sequence

| *Arabis* Location | F285 Location | Expected Amino acid | Amino acid Found | Type of Substitution |
|---|---|---|---|---|
| 141 | 122 | *Glutamic acid (E) | Lysine (K) | Strongly similar |
| 142 | 123 | Threonine (T) | Same | |
| 163 | 144 | *Glutamic Acid (E) | Same | |
| 177 | 160 | Tryptophan (W)[1] | Tyrosine (Y) | Strongly similar |
| 192 | 175 | *Glutamine (Q) | Proline (P) | Different |
| 194 | 177 | *Serine(S) | Tyrosine (Y) | Different |
| 197 | 180 | *Tyrosine (Y)[2] | Same (in NYNY) | |
| 198 | 181 | Asparagine (N) | Same (in NYNY) | |
| 273 | 257 | *Asparagine (N) | Tyrosine (Y) | Different |

*Amino acids proven by mutagenesis to be required for chitinase activity (Iseli-Gamboni et al., "Mutation of Either of Two Essential Glutamates Converts the Catalytic Domain of Tobacco Class I Chitinase Into a Chitin-Binding Lectin," Plant Sci 134:45–51 (1998), which is hereby incorporated by reference in its entirety).
[1]Retained as W in AAF29391.1 and found as Y in 3 of 4 cotton chitinases (Q39799, Q39785, and AAD11255). Other comparisons of F285 with all 4 cotton chitinases in the databases are consistent with the table.
[2]Changed to F in AAF29391.1, the other *Arabidopsis* homolog of F285.

The difference between F285, its closest *Arabidopsis* homolog, and other chitinases is emphasized by comparing their similar sequences near NYNY (a substrate binding site) to a putative consensus sequence described for several classes of chitinases (Hamel et al., "Structural and Evolutionary Relationships Among Chitinases of Flowering Plants," *J. Mol. Evol.*, 44:614–624 (1997), which is hereby incorporated by reference in its entirety) and with the *Arabis* chitinase (AAF69789.1) as a representative of the consensus-type sequence (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety). In this case, gaps inserted in all the sequences, including the putative consensus sequence, may create the best mutual alignment. As seen in TABLE 4, the sequence of F285 and its *Arabidopsis* homolog could be viewed in comparison to the consensus and the *Arabis* sequence as: (a) adding Y with the result that the hydrophobic domain containing NYNY is lengthened; (b) deleting QLS with the result that a conserved P (in 38 of 39 listed chitinase sequences, Hamel et al., "Structural and Evolutionary Relationships Among Chitinases of Flowering Plants," *J. Mol. Evol.*, 44:614–624 (1997), which is hereby incorporated by reference in its entirety) is nearer the NYNY domain; and (c) adding AL with the result that the conserved GRG (in 38 of 39 listed chitinase sequences, Hamel et al., "Structural and Evolutionary Relationships Among Chitinases of Flowering Plants," *J. Mol. Evol.*, 44:614–624 (1997), which is hereby incorporated by reference in its entirety) remains 5 residues from the NYNY domain. Although this reasoning is hypothetical, it emphasizes the difference between the sequences of F285 and its *Arabidopsis* homolog compared to previously described chitinase sequences. Both the Q and the S are proven to be essential for catalysis in some chitinases (Hamel et al., "Structural and Evolutionary Relationships Among Chitinases of Flowering Plants," *J. Mol. Evol.*, 44:614–624 (1997); Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which are hereby incorporated by reference in their entirety), and either their substitution with different amino acids (TABLES 2 and 3) or hypothetical deletion (TABLE 4) may cause the function of F285 and its *Arabidopsis* homolog to diverge from that typically expected of chitinases. Alternatively, F285 and its *Arabidopsis* homologs could be a previously unrecognized type of chitinase with a unique cellular role.

TABLE 4

Optimized alignment between a chitinase consensus sequence, *Arabis* chitinase, F285, and the closest *Arabidopsis* homolog to F285

| | * *   * | |
|---|---|---|
| Consensus | GRG--PIQLS-wNYNYGpACrAI | (SEQ ID NO: 17) |
| AAF69789 | ...--.M...-.......LC.... | |

TABLE 4-continued

Optimized alignment between a chitinase consensus sequence,
Arabis chitinase, F285,
and the closest Arabidopsis homolog to F285

```
F285      170   ...AL..---Y......ET.D.L   189
BAA94976        ...AL.V---Y......QT.E.L
                   +            x+ x +
```

Symbols:
-: gap in the sequence inserted here for purposes of best mutual alignment
dot(.): sites of identical amino acids between sequences
plus (+): sites of substitution of weakly or strongly similar amino acids compared to the consensus sequence.
x: sites of different amino acids compared to the consensus sequence (SEQ ID NO: 17).
letters in AAF69789 (amino acid number 170–189 of SEQ ID NO: 15), F285 (amino acid number 170–189 of SEQ ID NO: 2), BAA94976 (amino acid number 170–189 of SEQ ID NO: 14): single letter codes for the amino acid substituted at that position
underline in BAA94976: region in the active site of authentic chitinases
asterisks (*) above Consensus: residues proven to be critical for function in authentic chitinases (Verburg et al., "Identification of an Essential Tyrosine Residue in the Catalytic Site of a Chitinase Isolated From Zea mays That is Selectively Modified During Inactivation With 1-ethyl-3-(3-dimethylaminopropyl)-carbodiimide," J. Biol. Chem., 267:3886–3893 (1992); Bishop et al., "Rapid Evolution in Plant Chitinases: Molecular Targets of Selection in Plant-Pathogen Coevolution, Proc. Nat'l. Acad. Sci. U.S.A., 97:5322–5327 (2000), which are hereby incorporated by reference in their entirety)

A similar divergence between F285 and its *Arabidopsis* homolog with other Family 19 chitinases is observed in a region previously defining part of a 'Signature' containing regions of putatively unchanging amino acids (underlined) in this family of glycosyl hydrolases (Robertus et al., "The Structure and Action of Chitinases," in Jolles, eds., *Chitin and Chitinases*, pp. 125–136 (1999), which is hereby incorporated by reference in its entirety; TABLE 5). The Signature contains two glutamic acid residues (E; at positions 122 and 144 of F285) that have been proven by mutagenesis to be catalytic residues (Iseli-Gamboni et al., "Mutation of Either of Two Essential Glutamates Converts the Catalytic Domain of Tobacco Class I Chitinase Into a Chitin-Binding Lectin," *Plant Sci.*, 134:45–51 (1998), which is hereby incorporated by reference in its entirety). In F285 and its *Arabidopsis* homolog, the putatively conserved catalytic E at position 122 is substituted with K, which is a very similar amino acid although it is positively charged at pH 6 whereas E is negatively charged and it has an amino terminus of its R group whereas E has a carboxy terminus. Substitution by targeted mutagenesis of this E with A (a different type of amino acid) abolishes catalytic activity in some chitinases, changing the protein into a chitin-binding lectin (Iseli-Gamboni et al., "Mutation of Either of Two Essential Glutamates Converts the Catalytic Domain of Tobacco Class I Chitinase Into a Chitin-Binding Lectin," *Plant Sci.*, 134: 45–51 (1998), which is hereby incorporated by reference in its entirety). However, the effect of change to K in F285 is unknown, although substitution with similar amino acids can cause changes in binding interactions of chitinases (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety). There are also many other examples of substitution of similar amino acids within the putatively unchanging signature residues. In addition, within the putatively unchanging signature residues, there are three sites (denoted by x) of substitution of different amino acids in F285 and its *Arabidopsis* homolog. These are more likely to have major functional consequences than the substitutions of similar amino acids. Note that the sequence of F285 and its *Arabidopsis* homolog are identical in this region, suggesting that the changes they both show compared to the Signature are important for their particular function. In contrast, the sequence of the *Arabis* chitinase (AAF69789) with a defensive role (Bishop et al., "Rapid Evolution in Plant Chitinases: Molecular Targets of Selection in Plant-Pathogen Coevolution, *Proc. Nat'l. Acad. Sci. U.S.A.*, 97:5322–5327 (2000), which is hereby incorporated by reference in its entirety) matches the regions of unchanging amino acids in the Signature exactly and has only similar substitutions at other locations.

TABLE 5

Comparison between part of a Family 19 Signature sequence,
Arabis chitinase, F285, and the closest Arabidopsis homolog to F285

```
                               *                   *
Signature       KREVAAFLAQTSHETTGGWATAPDGAFAWGYCFKQERGA    (SEQ ID NO: 18)
AAF69789        .K.I...FG...........S....P.S........QNP    (SEQ ID NO: 19)
F285      109   MK......GHVGSK.SC.YGV.TG.PL...L.YNK.MSP   133
```

TABLE 5-continued

Comparison between part of a Family 19 Signature sequence,
Arabis chitinase, F285, and the closest Arabidopsis homolog to F285

```
BAA94976        MK......GHVGSK.SC.YGV.TG.PL...L.YNK.MSP     (SEQ ID NO: 20)
                + +    +++++X+ +X +++ ++ +++   X +++ X++
```

Symbols:
underlines in Signature (SEQ ID NO: 18): regions of amino acids previously
defined as invariable
asterisks (*) above Signature: residues proven by mutagenesis to be cata-
lytic sites in authentic chitinases (Iseli-Gamboni et al., "Mutation of
Either of Two Essential Glutamates Converts the Catalytic Domain of Tobacco
Class I Chitinase Into a Chitin-Binding Lectin," Plant Sci., 134:45–51
(1998), which is hereby incorporated by reference in its entirety)
dot (.): sites of identical amino acids between sequences
plus (+): sites of substitution of weakly or strongly similar amino acids
compared to the signature sequence.
x: sites of substitution of different amino acids compared to the signature
sequence.
letters in AAF69789 (SEQ ID NO: 19), F285 (amino acid number 109-133 of SEQ
ID NO: 2), and BAA94976 (SEQ ID NO: 20): single letter codes for the amino
acid substituted at that position In summary, the data show that F285 and its closest *Arabidopsis* homolog are much more similar to each other than to the many chitinases in the sequence databases. The data allow the possibility that F285 and its *Arabidopsis* homologs have a function somewhat different than previously described for chitinases. The change in protein structure near the substrate binding sites and in the catalytic region are likely to be important for the special function and/or optimal function of F285 and its *Arabidopsis* homologs. For example, these proteins might interact with N-acetyl-glucosamine oligomers or heteropolymers found in as yet unidentified substrate molecules. Possible substrate molecules could include signaling molecules or glycoproteins containing homo- or hetero-oligomers of N-acetylglucosamine, not only structural chitin in insects or fungi (Sahai et al., "Chitinases of Fungi and Plants: Their Involvement in Morphogenesis and Host-Parasite Interaction," *FEMS Microbiology Rev.*, 11:317–338 (1993), which is hereby incorporated by reference in its entirety).

The fact that F285 was discovered by analyzing changes in gene expression in the context of a particular developmental event (the initiation and continuation of secondary wall deposition in cotton fibers) and the *Arabidopsis* homologs of F285 were discovered only by complete sequencing of the *Arabidopsis* genome suggest that these chitinase-related proteins are more rarely expressed in the plant. This possibility is consistent with data from Northern blots of various cotton tissues (FIG. 2). The high, cross-species, amino acid identity of F285 and its closest *Arabidopsis* homolog (76% identical; TABLE 1) intuitively suggest that these proteins have a critical role, possibly a developmental role, in the life of the plant. In contrast, chitinases such as are encoded by Arabis AAF69789.1 and *Gossypium* Q39799, which are more dissimilar to F285, have been most clearly associated with defensive roles. The existence of the *Arabidopsis* homologs of F285 opens efficient avenues to test the protein function via screening stocks of *Arabidopsis* insertional mutants be standard molecular biological techniques. In addition, gene expression could be down-regulated in *Arabidopsis* or cotton by anti-sense or RNAi technology that are standard molecular biology techniques.

Example 4

Assay of Chitinase Activity

Figure 4:
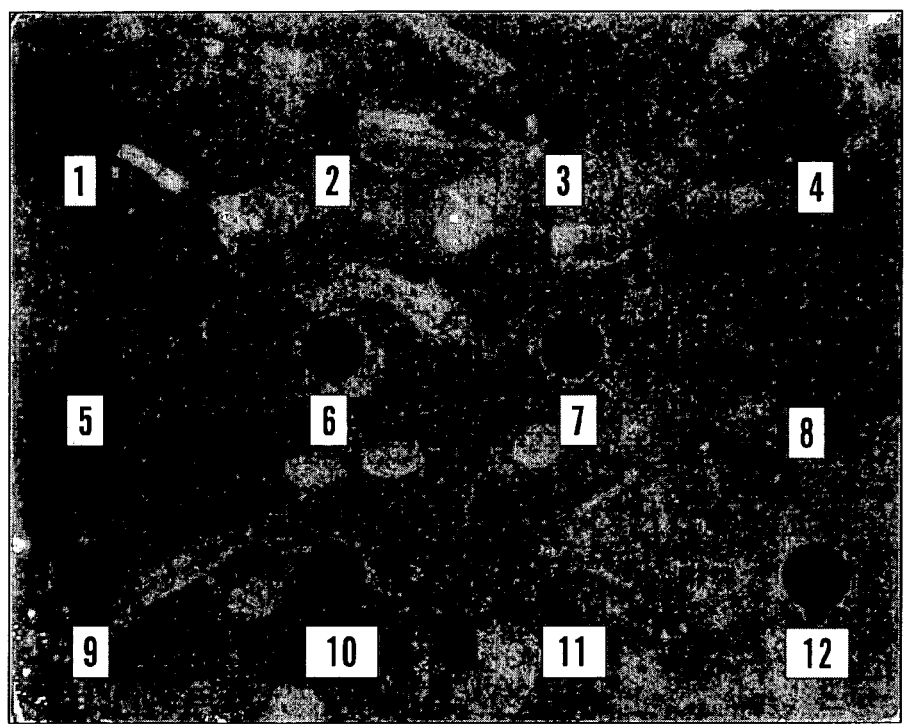
FIG. 4 illustrates the detection of chitinase activity in protein extracts of various tissues as follows:
  Area 1: 8 DPA greenhouse-grown fibers, untreated before protein extraction
  Area 2: 17 DPA greenhouse-grown fibers, untreated before protein extraction
  Area 3: 24 greenhouse-grown fibers, untreated before protein extraction
  Area 4: 31 greenhouse-grown fibers, untreated before protein extraction
  Area 5: 18 day old leaves, untreated before protein extraction.
  Area 6: 18 day old leaves, water-treated at 16 days after planting
  Area 7: 18 day old leaves, salicylic acid (SA)-treated at 16 days after planting
  Area 8: Negative control (Water)
  Area 9: 8 DPA cultured fibers, water-treated
  Area 10: 8 DPA cultured fibers, SA-treated on 6 DPA
  Area 11: Negative control (BSA solution)
  Area 12: Positive control (Commercial bacterial chitinase)

To begin to explore the biological role of the cognate protein of F285, chitinase activity was assayed in greenhouse-grown and cultured cotton fibers and seedling leaf blades in the presence and absence of salicylic acid (SA) and ethephon (ETH), an ethylene-producing compound. SA and ETH were used to spray leaves or cotton ovules plus fiber cultured as previously described in Haigler et al., "Cultured Cotton Ovules as Models for Cotton Fiber Development Under Low Temperatures," *Plant Physiology*, 95: 88–96 (1991), which is hereby incorporated by reference in its entirety, because these compounds induce chitinases in many other systems (Cutt et al., "Pathogenesis-Related Proteins," in Boller eds., *Genes Involved in Plant Defense*, New York, N.Y.:Springer-Verlag/Wien, pp. 209–243 (1992), which is hereby incorporated by reference in its entirety). Seedlings were sprayed (to the level of run-off) with SA (2 mM, pH 6.8), ETH (1 mg/ml; 2-chloroethylphosphoric acid), or water (as a control) 16 days after planting, covered loosely with plastic bags, and the leaves and stems were harvested 2 days later. At harvest, the SA and water-treated seedlings looked healthy with only a few areas of necrosis on leaves and cotyledons. However, the ETH-treated seedlings had about ⅓ of leaves abscised. Ovules cultured on 1 DPA were removed from culture flasks on 6 DPA, sprayed similarly, and replaced in flasks, followed by fiber harvesting on 8 DPA. Droplets of tissue extracts (10 µg total protein; extracted per methods of Mauch et al., "Antifungal Hydrolases in Pea Tissue. I. Purification and Characterization of Two Chitinases and Two β-1,3-Glucanases Differentially Regulated During Development and in Response to Fungal Infection," *Plant Physiology*, 87: 325–333 (1988), which is hereby incorporated by reference in its entirety, or control solutions were applied to areas (indicated by 1–12 in FIG. 4) on a polyacrylamide gel containing suspended glycol chitin, and incubation to allow enzyme activity was carried out for 1 h at 37° C. A fluorescent brightener, Tinopal LPW, with high affinity for polymeric chitin was applied, and the gel was excited with UV light. Subsequently, chitinase activity in tissue extracts was detected by measuring the ability to clear (degrade) water-soluble glycol chitin suspended in the polyacrylamide gel (Trudel et al., "Detection of Chitinase Activity After Polyacrylamide Gel Electrophoresis," *Anal. Biochem.*, 178:362–366 (1989), which is hereby incorporated by reference in its entirety). Dark areas indicate that the polymeric chitin in that location was degraded so that the fluorescent dye no longer bound to it. Therefore, dark areas demonstrate chitinase activity in the applied solution.

The positive control (area 12) showed strong chitinase activity. The negative controls (areas 8 and 11) showed no chitinase activity. All the cotton tissues tested showed chitinase activity, and no SA-induction of enzyme activity was observed by this qualitative test.

Example 5

Induction of F285 Expression in Fibers by SA

Figure 5:
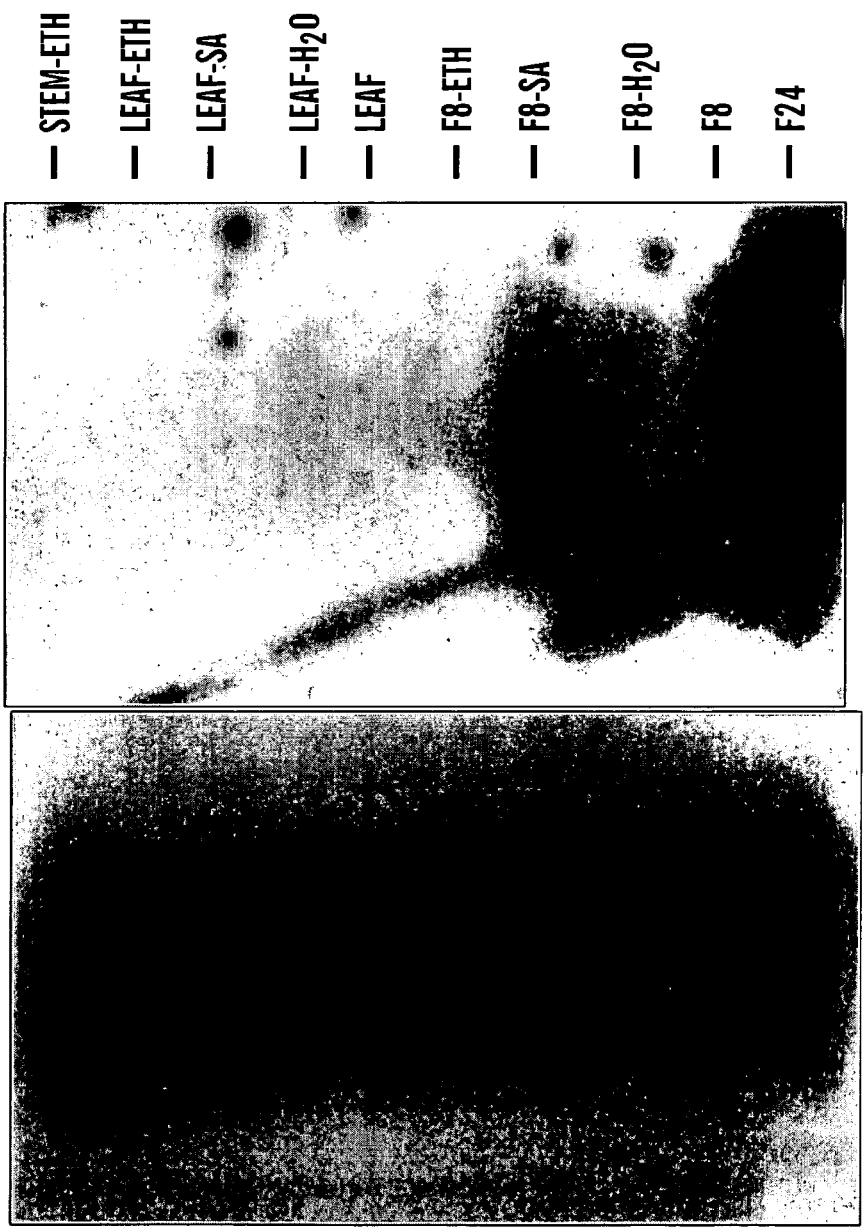
FIG. 5 shows a Northern blot, testing for induction by SA or ethephon (ETH) of expression of F285. The top frame shows incubation with a probe to F285, and the bottom frame shows incubation with a probe to 18S RNA to show the comparative level of RNA loading in each lane. The tissue and pre-treatment, if any, are indicated above each lane. Treatments, if any, were applied to seedlings 16 days after planting, and organs were harvested two days later. Treatments, if any, were applied to ovules at 6 DPA with harvest occurring at 8 DPA.

Northern blots were performed to indicate whether or not the F285 promoter was responsive to the same inductive signals of many other plant chitinases (FIG. 5). Treatment with water was used as a negative control. Fiber was tested at 8 and 24 DPA as indicated by the lane labels, and stem and leaf tissue was harvested at 18 days after treatment, if any, at 16 days. No induction of F285 expression was found in the leaves treated with SA or ETH or in seedling stems treated with ETH. However, weak expression was detected in SA-treated, but not in ETH- or H$_2$O-treated, 8 DPA fibers from cultured ovules (the blot was exposed to film for 4 days). These data suggest that the F285 promoter is only weakly responsive to inducers of other defense genes, and this may argue for a developmental role of F285.

Example 6

Identification of a Possible F285 Gene Family

Figure 6:
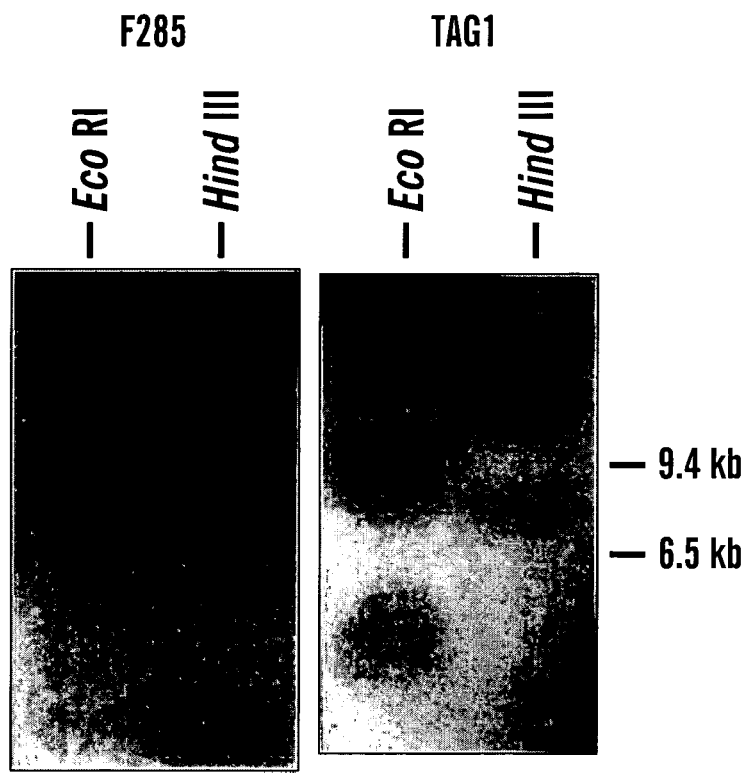
FIG. 6 shows a Southern blot of cotton genomic DNA digested with EcoRI and Hind III restriction enzymes and probed with the F285 full-length cDNA and, subsequently, with a fragment of another member of its gene family, TAG1.
Figure 7:
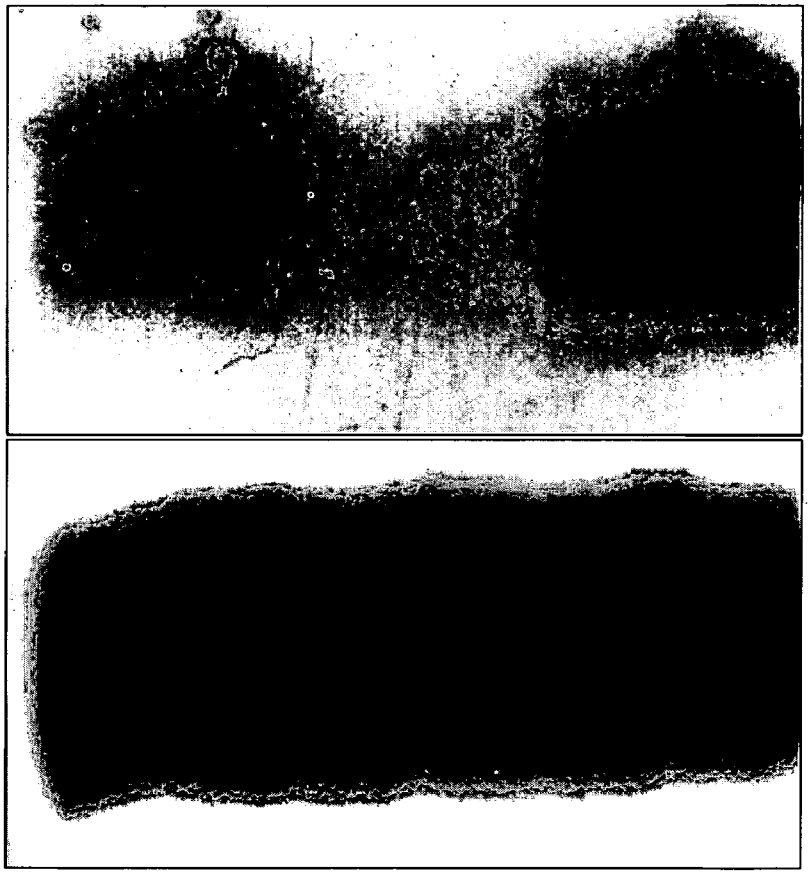
FIG. 7 shows a Northern blot testing the expression of TAG1. The top frame shows incubation with a probe to TAG1, and the bottom frame shows incubation with a probe to 18S RNA to show the comparative level of RNA loading in each lane. Tissues tested, including roots, stems, and leaves, and stripped ovules at 18 DPA, fibers at 8 DPA, and fibers at 24 DPA, are indicated above each lane.

FIG. 6 shows a Southern blot of cotton genomic DNA (prepared from leaves of 18 day old seedlings) digested with EcoR1 and Hind III restriction enzymes and probed with the F285 full-length cDNA; the banding pattern suggests 4–5 family members. In order to begin to understand the genomic and functional diversity of a possible F285 gene family, a primer from a distinctive region (6 TAG repeats) near the 3' untranslated end of the F285 sequence was used in PCR screening of the fiber cDNA library, followed by cloning of the amplified PCR products. Three colonies were chosen for insert-end sequencing, one of which was found to be different from the other two. This clone, designated TAG1, was used for Southern (FIG. 6) and Northern hybridization (FIG. 7). The genomic DNA blot used for F285 hybridization was stripped and reprobed with TAG1, which hybridized to a similar set of fragments with different hybridization intensities. Therefore, F285 and TAG1 are related at the DNA level.

TAG1 was expressed in greenhouse-grown fibers at 8 DPA (primary wall stage) and up-regulated in fibers at 24 DPA (secondary wall stage). Weak expression was also detected in ovules stripped of fibers (although some contaminating fiber parts cannot be excluded) and in roots and stems. Expression was not detected in leaves. Therefore, TAG1 had a broader expression pattern than F285.

Example 7

Identification of a Promoter and a Homolog of F285, Called F286

To attempt to isolate the F285 promoter region from cotton, a custom *Gossypium hirsutum* cv. Acala SJ-2 genomic cotton library in lambda Fix II (Stratagene, La Jolla, Calif.; kindly provided by Dr. T. Wilkins) was screened under standard hybridization conditions (Sambrook et al., *Molecular Cloning: A Laboratory Manual*, Second Edition, Cold Springs Laboratory, Cold Springs Harbor, N.Y. (1989), which is hereby incorporated by reference). The entire F285 cDNA clone was labeled with $^{32}$p, using Prime-a-Gene Labeling System Kit (Promega, Madison, Wis.) and hybridized to ca. 5×10$^5$ phage plaques lifted on Nylon membranes (Hybond-N, Amersham, Uppsala, Sweden) in the initial screen. Of the 6 hybridizing plaques obtained, the phage DNA was isolated from the cultures of five plaques and subjected to Xba I restriction enzyme digestion. The restriction pattern revealed that there were at least four bands in the DNA from each plaque. Southern hybridization with the same F285 probe showed that only one band, ca. 4.4 kb in size, hybridized with the probe of F285 fragment. The ca. 4.4 kb fragment was cut out of the agarose gel and purified by Jetsorb gel extraction kit (PGC Scientific, Gaitthersburg, Md.) for subcloning.

To subclone the above 4.4 kb fragment, the vector pBS (Stratagene, La Jolla, Calif.) was digested with Xba I, dephosphorylated using calf intestinal phosphatase (Promega, Madison, Wis.), and ligated with 4.4 kb fragment using T4 ligase and standard methods (Sambrook et al., *Molecular Cloning: A Laboratory Manual*, Second Edition, Cold Springs Laboratory, Cold Springs Harbor, N.Y. (1989), which is hereby incorporated by reference). Then, the ligation reaction was transformed into the *E. coli* DH 5α cells (Promega, Madison, Wis.), and the transfonnants were selected on X-gal/IPTG LB agar plates. The plasmid DNA, designated as 47A, was isolated with the QiaGen xIAprep Spin Miniprep Kit (Qiagen, Almeda, Calif.) for further manipulation and sequencing.

To identify the putative promoter region within clone 47A, the T3 promoter sequence (from vector pBS) was used as a starting forward primer and a synthesized oligonucleotide primer representing nucleotides number 159–178 of the F285 cDNA sequence (SEQ ID NO: 1) was used as a starting reverse primer for PCR-based automated sequencing in a core facility. Based on the newly generated sequence, additional primers were designed and chromosome walking continued in successive steps until a 2.34 kb region of genomic DNA was completely sequenced on both strands. This sequencing method is well known to practitioners of the art (Sambrook et al, "Molecular Cloning, A Laboratory Manual," 3rd edn, *Cold Spring Harbor Laboratory Press*: Cold Spring Harbor, N.Y., pp 12.10–12.100 (2001)). The 2.34 kb sequence included 90 bp of the 5' coding region, all of the 5' region upstream of the coding sequence that was included in clone 47A, and 145 bp of the pBS vector. The 5' region upstream of the coding sequence was expected to contain the promoter.

The F285 cDNA sequence was aligned against the sequence from clone 47A using the BLAST 2 Sequence Program. In the 90 bp of overlapped coding region, only 70 bp were identical (77% identity), indicating that the identified promoter fragment may belong to a homologous gene to F285. Therefore, the remainder of the insert of clone 47A was completely sequenced on both strands by the chromosome walking method described above using a synthesized oligonucleotide primer (5' GAGTGTGAGTGCCCATCATT 3'; nucleotides 1916–1935 of SEQ ID NO: 10) as the starting forward primer and the T7 promoter sequence (from vector pBS) as a starting reverse primer. Sequence annotation of the clone 47A using a gene prediction program (Burge et al., "Finding the Genes in Genomic DNA," *Curr. Opin. Struct. Biol.*, 8:346–354 (1998), which is hereby incorporated by reference in its entirety) revealed that it contains two exons (376 bp and 575 bp) with an intervening intron (131 bp). The putative cDNA sequence, designated as F286 (SEQ ID NO: 3), showed: (a) 85.0 % homology at the nucleotide level to the F285 cDNA; and (b) 87.46% identity and 97.18% similarity at the amino acid level to the F285 cDNA. (With the most variable 30 amino acid N-terminal signal sequence excluded, there was 89.93% identity and 97.92% similarity between the two coding sequences.) The high relatedness between the two coding sequences showed that F285 and F286 are homologous genes, and the non-identical amino acids were scattered throughout the proteins. Therefore, the Northern blots produced with an F285 cDNA probe would be expected to reflect expression of both F285 and F286. Both genes are expected to have strongly enhanced expression in secondary wall stage cotton fiber, although their 5' untranslated regions (UTR) are not identical (based on the partial sequence of the 5' UTR in the F285 cDNA).

The 2.1 kb fragment upstream of the F286 coding sequence was henceforth referred to as the F286 promoter, and this region may contain all the regulatory elements required to direct correct temporal and spatial expression of F286. Due to the lack of information concerning the exact length of the effective F286 promoter, genomic fragments of four lengths were PCR-amplified—2.1 kb (SEQ ID NO: 10), 1.8 kb (SEQ ID NO: 9), 1.4 kb (SEQ ID NO: 8), and 1.0 kb (SEQ ID NO: 7)—upstream of the putative translation start codon in the F286 gene sequence. Turbo pfu proofreading DNA polymerase (Stratagene, La Jolla, Calif.) was used to increase accuracy of the amplification. The four forward primers were:

Overproduction of Ethylene," *Plant Cell*, 14:165–179 (2002), which is hereby incorporated by reference in its entirety). A mutation in AF422178 caused elevated ethylene production, ectopic deposition of lignin, aberrant cell shapes, and some incomplete primary cell walls in the pith of *Arabidopsis* inflorescence stems. Except to show that ethylene over-production caused some of the aberrant phenotypes, primary and secondary effects of the mutation were not distinguishable and no specific association of AAL37737 with cell wall or cellulose synthesis was suggested. Its expression in all organs of *Arabidopsis*, lack of induction by chemicals that typically induce expression of defensive chitinases, and correlation with many developmental aberrations when mutated showed that AF422178 is essential for normal plant growth and development in *Arabidopsis* (Zhong et al., "Mutation of a Chitinase-Like Gene Causes Ectopic Deposition of Lignin, Aberrant Cell Shapes, and Overproduction of Ethylene," *Plant Cell*, 14:165–179 (2002), which is hereby incorporated by reference in its entirety).

F285, F286, BAA94976, and AAL37737 may all be members of a unique class of chitinases with developmental importance, more specifically developmental importance in cell wall and/or cellulose synthesis as previously discussed. F285, F286, and BAA94976 would then be some members of the class that are required during secondary wall deposition, whereas AAL37737 may be one member of the class that is required during primary wall deposition. Although active in different cells and/or developmental stages, these "cell wall/cellulose" chitinases are expected to have similar function, which is supported by their high amino acid

```
for 2.1 kb, 5' GCTGAGTCGAC GATATCGAATTCCTGCAGCC 3';        (SEQ ID NO: 21)

for 1.8 kb, 5' GCTGAGTCGAC CTTCAATCTCTGCCAATGATC 3';       (SEQ ID NO: 22)

for 1.4 kb, 5' GCTGAGTCGAC AACCTCTCGAGCTGCCATAT 3'; and    (SEQ ID NO: 23)

for 1.0 kb, 5' GCTGAGTCGAC CTGAGACCAGCGTTCAACAT 3'.        (SEQ ID NO: 24)
```

The Sal I restriction recognition site sequence (underlined) and the 5 upstream nucleotides were introduced artificially into each primer, which resulted in the Sal I site becoming part of the amplified promoter fragments. The reverse primer for each different length of F285 fragment was the same:
5' GCTAGTCTAGATATCAAAGATACGAAGCAAAATG 3' (SEQ ID NO: 25).

This primer corresponds to the promoter sequence just before the start codon with the Xba I restriction site (italic) and the 5 upstream nucleotides artificially added. The amplified promoter fragments of four lengths were functionally tested by stable transformation of cotton.

Example 8

Identification of Consensus Sequences in a New Class of Chitinases

As previously described, F285 and F286 have *Arabidopsis* homologs, BAA94976 (76.28% amino acid identity to F285) and AAL37737 (also called AAF29391.1; 67.49% amino acid identity to F285; in nucleotide sequence, doubly accessioned as AF422178 and AF422179). BAA94976 and AAL37737 are 70% identical in amino acid sequence (Zhong et al., "Mutation of a Chitinase-Like Gene Causes Ectopic Deposition of Lignin, Aberrant Cell Shapes, and conservation (only 19.2% difference in the amino acid sequence of the 4 proteins, including ones from two species.) About half of this difference occurs in the first 40 amino acids, implying that the functional region is even more highly conserved across developmental stages and species.

Based on the hypothesis of conserved function, the sequences of all four proteins can be compared against amino acid sequences representing the more typical defensive chitinases to identify unique consensus sequences within this new "cell wall/cellulose-related" class of chitinases. As previously discussed, *Arabis* AAF69789 is one example of a defensive chitinase and, conveniently, five more defensive chitinases are aligned with *Arabidopsis* BAA94976 and AAL37737 in Zhong et al., "Mutation of a Chitinase-Like Gene Causes Ectopic Deposition of Lignin, Aberrant Cell Shapes, and Overproduction of Ethylene," *Plant Cell*, 14:165–179 (2002), which is hereby incorporated by reference in its entirety. Zhong et al. used this alignment only to show similarity of BAA94976 and AAL37737 to other chitinases, specifically by pointing out conservation among all the aligned proteins of 5 amino acid residues thought to be conserved among all chitinases and showing some generalized amino acid conservation throughout the proteins. TABLE 4 (chitinase consensus sequence) and TABLE 5 (Family 19 signature sequence)

already illustrate that longer functional regions can be compared between the "secondary wall" chitinases F285 and BAA94976 vs. "defensive" chitinase *Arabis* AAF68789 to show that F285 and its homologs do represent a new class of chitinase. (The compared regions are defined as functional because each one contains 2 or more amino acids proven by mutagenesis to be critical for function in authentic chitinases as shown in TABLES 4 and 5.)

By including "cell wall/cellulose" F286 and AAL37737 and the 5 miscellaneous "defensive" chitinases, as mentioned in Zhong et al., "Mutation of a Chitinase-Like Gene Causes Ectopic Deposition of Lignin, Aberrant Cell Shapes, and Overproduction of Ethylene," *Plant Cell*, 14:165–179 (2002), which is hereby incorporated by reference in its entirety, in the sequence comparisons, one can further identify conserved sequences within the new class of "cell wall/cellulose" chitinases and show that these differ over substantial amino acid lengths from the same functional domains in the "defensive" chitinases.

Considering the region corresponding to the Family 19 signature sequence in TABLE 5, the "cell wall/cellulose" chitinases have 90% identity (and 97.4% similarity) over the 39 amino acid region. A consensus sequence based on identical amino acids is shown below the sequence alignments in TABLE 6.

sequence becomes 50% identical/75% similar across five genes. The substantial drop in relatedness between all five sequences when only one "defensive" chitinase is added confirms that the "cell wall/cellulose" chitinases represent a distinct class. The same conclusion is confirmed by inspection of the mutual alignment of BAA94976 and AAL37737 with the five other defensive chitinases in Zhong et al., "Mutation of a Chitinase-Lik Gene Causes Ectopic Deposition of Lignin, Aberrant Cell Shapes, and Overproduction of Ethylene," *Plant Cell*, 14:165–179 (2002), which is hereby incorporated by reference in its entirety. In the Family 19 signature sequence, the five "defensive" chitinases have 59–64% identity with the "cell wall/cellulose" chitinases. In the chitinase consensus sequence, the five "defensive" chitinases have 45–50% identity with the "cell wall/cellulose" chitinases. Both percentages are greatly reduced relative to the comparison between the four "cell wall/cellulose" chitinases alone.

Because of the distinctiveness in these functional regions of the "cell wall/cellulose" chitinases, one can propose that this distinct class of chitinases is characterized by consensus sequences in these regions similar to the ones shown above. Specifically, the analysis here predicts that other members of the "cell wall/cellulose" class of chitinases will have greater than or equal to 75% identity with the "cell wall/cellulose" consensus sequence in the region of the Family 19 Signature

TABLE 6

Region of the Family 19 Signature Sequence (39 amino acids)

```
F285      MKEVAAFLGHVGSKTSCGYGVATCGPLAWGLCYNKEMSP  (residue 109-133 of SEQ ID NO: 2)
F286      MKEVAAFLGHVGSKTSCGYCVATGGPLAWGLCYNKEMSP  (residue 109-133 of SEQ ID NO: 4)
BAA94976  MKEVAAFLGHVGSKTSCGYGVATGGPLAWGLCYNKEMSP  (residue 109-133 of SEQ ID NO: 20)
AAL37737  QKENAAFLGHVASKTSCGYGVATGGPLAWGLCYNREMSP  (SEQ ID NO: 26)
          x..+.......+.....................+....
Consensus -KE-AAFLGHV-SKTSCGYGVATGGPLAWGLCYN-EMSP  (SEQ ID NO: 27)
```

Symbols:
x: sites of appearance of different amino acids among all four sequences
plus (+): sites of substitution of weakly or strongly similiar amino acids among all four sequences Considering the region corresponding to the chitinase consensus sequence in TABLE 4, the "cell wall/cellulose" chitinases have 75% identity (and 95% similarity) over the 20 amino acid region. A consensus sequence based on identical amino acids is shown below the sequence alignments in TABLE 7.

Sequence and greater than or equal to 60% identity with the "cell wall/cellulose" Chitinase Consensus Sequence. The figures of 75% and 60% identity fall between those for comparison of the four known "cell wall/cellulose" chitinases alone and in combination with the "defensive" chitinases. These percentages allow for some expected diver-

TABLE 7

Region of the Chitinase Consensus Sequence (20 amino acids)

```
F285      GRGALPIYWNYNYGETGDAL  (residue 170-189 of SEQ ID NO: 2)
F286      GRGALPIYWNYNYGETGEAL  (residue 170-189 of SEQ ID NO: 4)
BAA94976  GRGALPVYWNYNYGQTGEAL  (residue 170-189 of SEQ ID NO: 20)
AAL37737  GRGALPIYWNFNYGAAGEAL  (SEQ ID NO: 28)
          ......+...+...x+.+..
Consensus GRGALP-YWN-NYG--G-AL  (SEQ ID NO: 29)
```

Symbols:
x: sites of appearance of different amino acids among all four sequences
plus (+): sites of substitution of weakly or strongly similar amino acids amoung all four sequences If the *Arabis* "defensive" chitinase, AAF69789, is added to these alignments, the Family 19 signature sequence becomes 38.5% identical/82% similar and the chitinase consensus gence between genes of different species by substitution of similar amino acids, but imply retention of distinctiveness of the new class of "cell wall/cellulose" chitinases.

Example 9

Production of Stably Transformed Cotton Plants

Figure 8:
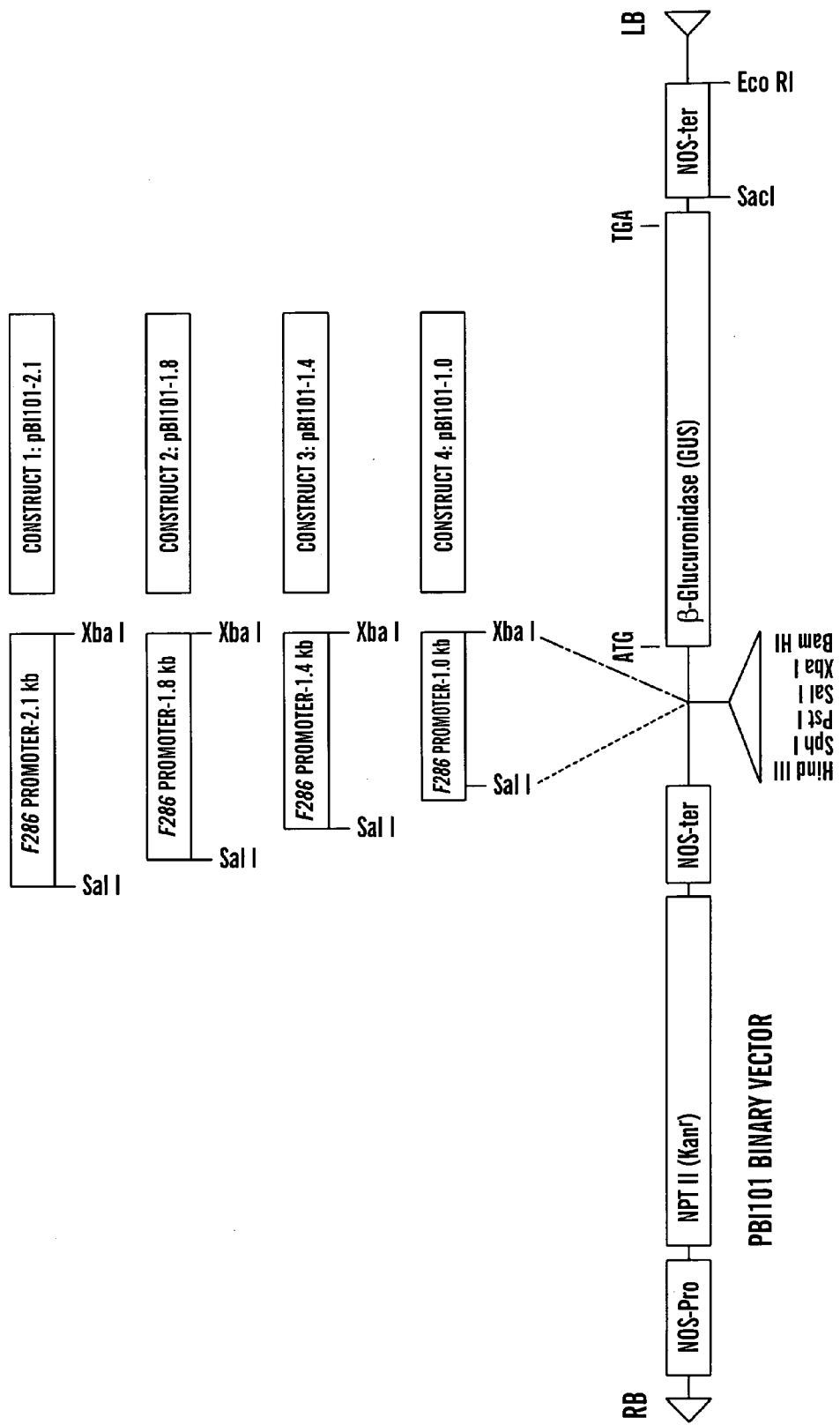
FIG. 8 is a schematic representation of the plasmid constructs containing different length promoters which were used for the transformation experiments.

The amplified F286-2.1 kb, F286-1.8 kb, F286-1.4 kb, and F286-1.0 kb promoter fragments were subsequently digested with Sal I+Xba I and subcloned into the corresponding sites of the binary Ti plasmid pBI101 (commercially available from Clontech, Palo Alto, Calif.; FIG. 8). The pBI101 binary vector is one of many that would be suitable for transformation of cotton. Plasmid pBI101 as purchased contained an NPTII transferase gene under control of the NOS promoter and with a NOS terminator, which provides a selectable marker for plant transformation. pBI101 also contained the GUS reporter gene encoding β-glucuronidase (GUS) including start and stop codons and the NOS terminator. The gusA gene is typically introduced into transgenic plants to act as a "reporter gene" for testing gene promoter function. Relevant principles and methods are commonly known and fully described (Gallagher (ed), "Gus Protocols: Using the GUS Gene As a Reporter of Gene Expression," 221 pp, Academic Press, New York (1992), which is hereby incorporated by reference in its entirety). The 4 promoter fragments just described were cloned in 5' of the GUS gene to produce 4 separate gene expression constructs: pBI101-2.1, pBI101-1.8, pBI101–1.4, and pBI101–1.0. In each of the 4 new constructs, GUS would be expressed only under the temporal and spatial pattern dictated by the F286-2.1 kb, F286-1.8 kb, F286-1.4 kb, and F286-1.0 kb promoter fragments.

Each of the 4 new constructs was introduced separately into *Agrobacterium* strain EHA 105 (Hood et al., "New *Agrobacterium* Helper Plasmids for Gene Transfer to Plants," *Transgenic Research*, 2: 208–218 (1993), which is hereby incorporated by reference in its entirety) by triparental mating (Svab et al., "Generation of Transgenic Tobacco Plants by Cocultivation of Leaf Disks with *Agrobacterium* Binary Vector," In: Maliga et al. (eds) Methods in Plant Molecular Biology: A Laboratory Course Manual, pp. 55–77, Cold Spring Harbor Laboratory Press (1995), which is hereby incorporated by reference in its entirety). *Agrobacteria* harboring the experimental plasmids were grown up before transformation in Luria Broth containing Kanamycin (50 μg/ml) to an OD=0.5–0.6, then diluted 1:20 into Murashige and Skoog's mineral salts and vitamins (M-5519; Sigma Chemical Company, St. Louis, Mo.) with glucose (0.3 g/ml) but lacking plant hormones. The diluted bacteria were used to infect ca. 0.5 cm segments of cotton (*Gossypium hirsutum* cv. Coker 312) hypocotyls.

Transformation of cotton (*Gossypium hirsutum* cv. Coker 312–17 or –5a, elite) hypocotyl sections and regeneration of plants via somatic embryogenesis were accomplished generally as described in Bayley et al., "Engineering 2,4-D Resistance in Cotton," *Theoretical and Applied Genetics*, 83: 645–649 (1992); Trolinder et al., "Somatic Embryogenesis and Plant Regeneration in Cotton (*Gossypium hirsutum* L.)," *Plant Cell Reports*, 6: 231–234 (1987); Umbeck et al., "Genetically Transformed Cotton (*Gossypium hirsutum* L.) Plants," *Bio/Technology*, 5: 263–266 (1987); U.S. Pat. No. 5,159,135 to Umbeck; Dang, "Expression of a Cotton Fiber 'Specific' Gene Promoter in Tobacco and Cotton," 96 pp, Ph.D. dissertation, Texas Tech University, Lubbock, Tex. (1996), which are hereby incorporated by reference in their entirety. The elite, highly embryogenic, selections of cv Coker 312 were made and seeds contributed by Dr. N. Trolinder (USDA-ARS, Lubbock, Tex.). The transformation and regeneration method included the major steps of co-cultivation of hypocotyl sections with *Agrobacterium*, growth of axenic transformed callus on selection medium, proliferation of embryogenic callus in suspension culture, and embryo maturation and germination over a period of about 8 months for each independent line. Longer times in tissue culture were avoided to minimize deleterious somaclonal variation, including infertility.

Methodological details were as follows. Seedlings were germinated from acid-delinted, sterilized, imbibed, seeds (70% EtOH 2 min, thoroughly water rinsed, soaked in sterile water, 7–8 h or overnight) on solidified (2 g/l Gelrite; Kelco Co, San Diego, Calif.) Stewart's medium (pH 6.8; Stewart et al., "In Ovulo Embryo Culture and Seedling Development of Cotton (*Gossypium hirsutum* L.)," *Planta*, 137:113–117 (1977), which is hereby incorporated by reference in its entirety) in 25×150 mm tubes, 30° C., 7–12 days, 16 h fluorescent light/8 h dark. Hypocotyl segments (ca. 0.5 cm) were inoculated (30 sec–5 min) with *Agrobacterium* prepared as described earlier. After removal of excess bacteria by wicking, hypocotyls were incubated 3–4 days (21–25° C.) on solidified (2 g/l Gelrite) MS medium (Sigma Chemical Company, M-5519; pH 5.8) with 30 g/l glucose, 2 mg/l NAA, and 0.1 mg/l kinetin to allow infection to occur. Hypocotyl segments were transferred to the same medium plus 50 μg/ml kanamycin (to select for growth of transformed tissue only) and 500 μg/ml Claforan (also called cefotaxime, to kill the Agrobacterium) and incubated (30° C.; light), transferring the hypocotyl segments every 2–4 weeks onto new medium (avoiding browning in medium). At the end of at least 6 weeks (typically 9–12 weeks; callus with at least 0.5 cm diameter may be separated from hypocotyl pieces at transfer), friable callus with moderate growth rate (preferably light grey/green in color and 0.5–1 cm in diameter) was transferred to suspension culture in a 50 ml flask with 15 ml MS medium plus 30 g/l glucose, 1.9 g/l $KNO_3$, and 25 μg/ml kanamycin for embryo proliferation (2–4 weeks growth until the cells attained about ½ volume of the medium, shaking, 30° C., light). Cells/embryos (in cultures that were solid white, brown, or green in clear medium) were collected by settling, big callus pieces were mechanically broken, and brown callus pieces were removed. Tissue was washed 3 times in suspension medium, resuspended at 10× tissue volume in suspension medium, and 2 ml aliquots were repetitively plated on solidified (2 g/l Gelright) suspension medium in 100×20 mm Petri plates, except that kanamycin was used at 50 μg/ml. Plates were cultured (30° C.; light; 2–4 weeks) until elongating embryos (≧3 mm) developed, which were transferred to Stewart's medium including 5 g/l sucrose, 1.5 g/l Gelrite, and 5 g/l agar for embryo maturation (30° C., light, 10–14 days). When true leaves developed, plantlets were transferred to the same medium in 1 pint canning jars with plastic tissue culture lids (Frank Moses, Rhyno Manufacturing, Riverside, Calif.) for growth (30° C., 16 h fluorescent light/8 h dark). When seedlings were 5–8 cm in height with 5 true leaves, a stem cutting was made above the second node and rerooted (7–14 days) in the same medium. This clone was transferred to soil when it had 3–5 white roots ca. 4 cm long and gradually hardened off by progressive venting of a loosely covering plastic bag before transfer to the greenhouse.

The 2.1 kb test was started on a larger scale (2750 hypocotyl pieces inoculated) than the others (1040, 1710, and 1040 hypocotyl pieces inoculated for the 1.8, 1.4, and 1.0 kb tests, respectively), which explains different numbers of lines finally available for each test. A transgenic "line" refers to plants originating from one original piece of callus because these are guaranteed to represent one or more (in different embryos) transformation events.

From T0 and T1 plants of the 2.1, 1.8, and 1.4 kb tests growing in the greenhouse and forming bolls, histological analyses of GUS expression patterns in developing fibers, juvenile and mature vegetative tissues, and reproductive plant tissues were performed. Tissue-specific expression patterns were the same between T0 and T1 plants. For the 1.0 kb test, juvenile and mature vegetative tissues were screened at T0. Systematic testing at T1 was performed on juvenile seedlings of 21, 6, and 8 lines of the 2.1, 1.8, and 1.4 kb tests, respectively, all of which showed resistance to Kanamycin. Resistance to Kanamycin via the NPTII gene under control of the 35S CaMV promoter, the antibiotic selection marker in the foreign gene expression cassette, indicated foreign gene insertion and expression. Kanamycin resistant cotton seedlings form lateral roots within Kanamycin medium, whereas non-transformed or null transformed seedlings produce a taproot only without lateral roots.

By adapting methods described in Umbeck et al, "Inheritance and Expression of Genes for Kanamycin and Chloramphenicol Resistance in Transgenic Cotton Plants," *Crop Science*, 29: 196–201 (1989), which is hereby incorporated by reference in its entirety, the ability of germinating seeds to form lateral roots within solidified medium containing Kanmycin was determined (Stewart's mineral salts and vitamins, pH 6.8, 2 g/l Gelright®, 50 µg/l Kanamycin). From each T0 plant, 24 acid-delinted, sterilized T1 seeds were germinated on the Kanamycin medium (10–12 ml/test tube) in a growth chamber (low light; 30° C.), scored after 5–7 days, and plants with lateral roots forming within the medium were transferred to soil after gently removing Kanamycin medium from the roots. Two-four resistant plants per embryo (as available) were transferred to soil. Seeds of three lines transformed with the GUS gene under the control of the 35S CaMV promoter (kindly provided by R. D. Allen; Song et al., "Expression of Two Tissue-Specific Promoters in Transgenic Cotton Plants," *The Journal of Cotton Science*, 4: 217–223 (2000), which is hereby incorporated by reference in its entirety) were treated similarly, and resistant seedlings of these plus untransformed parental C312–17 were planted in the greenhouse.

Of the seeds germinating normally (roots down and shoots up), counts were made for segregation of Kanamycin resistance: Kanamycin sensitivity, which allowed preliminary assessment of number of gene insertion sites in some cases. Segregation ratio data are preliminary, because 72 germinated seeds are needed to assess a 15:1 ratio arising from two independent insertion sites at $p \leq 0.01$. For traits under normal Mendelian inheritance, T1 seeds resistant to Kanamycin (with nulls eliminated and not considered) will be a segregating population with the following characteristics: (a) if one gene insertion site, ⅓++ and ⅔+0 seeds; and (b) if two gene insertion sites on non-homologous chromosomes, ⅛++++, ¼+++0, ⅜++00, and ¼+000 seeds. These four groups (++++, +++0, ++00, and +000) are not genetically or necessarily functionally equivalent within themselves because of the dual sites of gene insertion and possible positional effects of gene insertion on gene expression. The number of gene insertion sites does not account for possible tandem repeats of the foreign gene at one chromosomal site. Other more complex segregation ratios are possible if multiple gene insertion sites occur on the same or homologous chromosomes.

Example 10

Histological Methods and Results

As described in Gallagher (ed) "Gus Protocols: Using the GUS Gene As a Reporter of Gene Expression, 221 pp, Academic Press, New York (1992), which is hereby incorporated by reference in its entirety, GUS cleaves a histochemical substrate (e.g. X-GlcA: 5-Bromo-4-chloro-3-indolyl-β-D-glucuronic acid, cyclohexyl ammonium salt) at the β1 glucuronic bond between glucuronic acid and the 5-Bromo-4-chloro-3-indolyl moiety. Water insoluble, blue, dichloro-dibromo-indigo precipitates at the site of enzymatic cleavage, providing a qualitative marker for gusA expression in certain cells and tissues. Whole plant parts, if small, or sections are processed for GUS reactivity by standard protocols. Sections can be made by hand with a razor blade or with a microtome after embedding, e.g. paraffin embedding by a microwave-assisted protocol to preserve delicate tissues such as the cambium (Ruzin, *Plant Microtechnique and Microscopy*, 322 pp, Oxford Univ. Press, Oxford (1999), which is hereby incorporated by reference in its entirety). The blue color (or red color if darkfield optics are used) is evaluated in the dissecting and/or compound light microscope. Brightfield, differential interference contrast (DIC), and darkfield optics are useful to reveal GUS localization and plant structure, and parallel examination with polarization optics can reveal thickness of plant cell walls and organized cellulose microfibrils within plant cell walls to assist in evaluation of cell types where GUS is found.

Analysis of multiple lines of juvenile T1 plants showed that the longer promoters (2.1 and 1.8 kb) caused silencing of GUS expression, whereas this effect was not observed with the 1.4 kb promoter (TABLE 8).

TABLE 8

Histological Analysis of Presence or Absence of GUS in T1 Lines of the 2.1, 1.8, and 1.4 kb Tests

| Test | # Lines Tested | # Lines Positive | # Lines Negative | % GUS silencing |
| --- | --- | --- | --- | --- |
| 2.1 kb | 21 | 9 | 12 | 57% |
| 1.8 kb | 6 | 2 | 4 | 66% |
| 1.4 kb | 8 | 8 | 0 | 0 |

Therefore, the 1.4 kb promoter is preferred for absence of foreign gene silencing so that the number of useful lines arising from the transformation process will be maximized. For the 2.1 and 1.8 kb tests, silencing of GUS expression was observed in all tissues of the plant where positive expression was expected. Tissues chosen for analysis were expected to be growing tissues, and negative results in a line were confirmed in a second trial. Since the silencing of GUS expression was observed in plants that were kanamycin resistant, the 35S CaMV promoter and the F286 promoter must be affected differently by the factor that is causing GUS gene silencing. Possibly a negative regulatory element further upstream in the F286 promoter functions to repress gene expression when promoter/gene insertion occurs in a particular genomic micro-environment. The PLACE database of putative regulatory motifs found in plant cis-acting regulatory DNA elements (Higo et al., "Plant cis-Acting Regulatory DNA Elements (PLACE) Database," *Nucleic Acids Research*, 27: 297–300 (1999), which is hereby incorporated by reference in its entirety) was used to look for motifs that might be found only in the regions of the 2.1 and 1.8 kb promoter fragments that are upstream of the 1.4 kb fragment. TABLE 9 shows that at least 8 motifs meet this criterion, and these establish a possible basis for differential regulation of gene expression, including more frequent silencing, by the longer fragments. In addition, other motifs not identified via PLACE might be responsible for the observed gene silencing. The diverse regulatory motifs within the 2.1 kb or shorter fragments further illustrate that key regulatory elements, both those shown in TABLE 9 and others not yet known, might be artificially fused into a useful promoter with the deletion of other motifs not necessary or useful for the intended purpose as previously discussed.

By combining histological results from mature T0 plants and juvenile T1 plants, the following observations about the developmental pattern of GUS expression can be made. These results were the same for the 2.1 kb, 1.8 kb, and 1.4 kb tests. The results can be summarized by saying that all three promoter lengths drive gene expression preferentially in diverse secondary walled cells within the cotton plant, all of which contain cellulose as a major component. Similar results were obtained in T0 plants of the 1.0 kb test. There are numerous commercial applications for modification of cellulose content in plant stems, and the F286 promoter would be useful in such biotechnological strategies. The utility of the promoter is further emphasized by its exclusion of gene expression in: (a) secondary-walled vascular and guard cells of leaves, cotyledons, bracts, petals, and seeds; (b) the short linters that develop alongside the long cotton lint fibers; and (c) typical parenchyma cells such as the photosynthetic mesophyll and the bulky ground tissue of stems and roots.

TABLE 9

Putative regulatory motifs present in the F286 promoter

| # | Regulatory element | Location in F286 promoter | Promoter type | Consensus sequence | Putative regulatory role |
|---|---|---|---|---|---|
| 1 | GATABOX | 22 (−) | F286-2.1 | GATA | Light regulated and tissue-specific expression |
| 2 | CAATBOX1 | 49 (+) | F286-2.1 | CAAT | tissue-specific expression |
| 3 | GATABOX | 53 (+) | F286-2.1 | GATA | Light regulated and tissue-specific expression |
| 4 | GT1CONSENSUS | 53 (+) | F286-2.1 | GRWAAW | Binding site in many light regulated genes |
| 5 | IBOXCORE | 53 (+) | F286-2.1 | GATAA | Light regulated activities |
| 6 | GTGANTG10 | 66 (−) | F286-2.1 | GTGA | Pollen specificity |
| 7 | GATABOX | 70 (−) | F286-2.1 | GATA | Light regulated and tissue-specific expression |
| 8 | GTGANTG10 | 72 (−) | F286-2.1 | GTGA | Pollen specificity |
| 9 | GTGANTG10 | 82 (−) | F286-2.1 | GTGA | Pollen specificity |
| 10 | INRNTPSADB | 101 (−) | F286-2.1 | YTCANTYY | Light responsive transcription |
| 11 | CAATBOX1 | 103 (−) | F286-2.1 | CAAT | tissue-specific expression |
| 12 | GTGANTG10 | 127 (−) | F286-2.1 | GTGA | Pollen specificity |
| 13 | CCAATBOX1 | 145 (+) | F286-2.1 | CCAAT | Common sequence found in the 5'-non coding region of eukaryotic genes |
| 14 | CAATBOX1 | 146 (+) | F286-2.1 | CAAT | tissue-specific expression |
| 15 | CAATBOX1 | 176 (+) | F286-2.1 | CAAT | tissue-specific expression |
| 16 | CIACADIANLELHC | 176 (+) | F286-2.1 | CAANNNNATC (SEQ ID NO: 30) | Required for circadian expression of tomato Lhc gene |
| 17 | DOFCOREZM | 193 (−) | F286-2.1 | AAAG | tissue-specific expression |
| 18 | GTGANTG10 | 203 (−) | F286-2.1 | GTGA | Pollen specificity |
| 19 | DOFCOREZM | 219 (−) | F286-2.1 | AAAG | tissue-specific expression |
| 20 | TAAAGSTKST1 | 219 (−) | F286-2.1 | TAAAG | Guard cell-specific expression |
| 21 | GATABOX | 224 (+) | F286-2.1 | GATA | Light regulated and tissue-specific expression |
| 22 | CIACADIANLELHC | 224 (−) | F286-2.1 | CAANNNNATC (SEQ ID NO: 30) | Required for circadian expression of tomato Lhc gene |
| 23 | CAATBOX1 | 230 (−) | F286-2.1 | CAAT | tissue-specific expression |
| 24 | CCAATBOX1 | 230 (−) | F286-2.1 | CCAAT | Common sequence found in the 5'-non coding region of eukaryotic genes |
| 25 | REALPHALGLHCB21 | 231 (−) | F286-2.1 | AACCAA | Phytochrome regulation |
| 26 | POLLEN1LELAT52 | 236 (−) | F286-2.1 | AGAAA | Pollen specificity |
| 27 | SEF4MOTIFGM7S | 249 (+) | F286-2.1 | RTTTTR | Seed specificity |
| 28 | DOFCOREZM | 259 (−) | F286-2.1 | AAAG | tissue-specific expression |
| 29 | MARTBOX | 260 (+) | F286-2.1 | TTWTWTTWTT (SEQ ID NO: 31) | "T-Box" motif found in matrix attachment region |
| 30 | MARTBOX | 261 (+) | F286-2.1 | TTWTWTTWTT (SEQ ID NO: 31) | "T-Box" motif found in matrix attachment region |
| 31 | MARTBOX | 262 (+) | F286-2.1 | TTWTWTTWTT (SEQ ID NO: 31) | "T-Box" motif found in matrix attachment region |
| 32 | GT1CORE | 270 (−) | F286-2.1 | GGTTAA | Light regulated |
| 33 | REALPHALGLHCB21 | 272 (+) | F286-2.1 | AACCAA | Phytochrome regulation |

TABLE 9-continued

Putative regulatory motifs present in the F286 promoter

| # | Regulatory element | Location in F286 promoter | Promoter type | Consensus sequence | Putative regulatory role |
|---|---|---|---|---|---|
| 34 | CIACADIANLELHC | 275 (+) | F286-2.1 | CAANNNNATC (SEQ ID NO: 30) | Required for circadian expression of tomato Lhc gene |
| 35 | TBOXATGAPB | 275 (−) | F286-2.1 | ACTTTG | Light regulated |
| 36 | DOFCOREZM | 276 (+) | F286-2.1 | AAAG | tissue-specific expression |
| 37 | GTGANTG10 | 283 (−) | F286-2.1 | GTGA | Pollen specificity |
| 38 | DOFCOREZM | 286 (−) | F286-2.1 | AAAG | tissue-specific expression |
| 39 | GT1CONSENSUS | 287 (−) | F286-2.1 | GRWAAW | Binding site in many light regulated genes |
| 40 | POLLEN1LELAT52 | 289 (−) | F286-2.1 | AGAAA | Pollen specificity |
| 41 | INRNTPSADB | 293 (+) | F286-1.8 | YTCANTYY | Light responsive transcription |
| 42 | CAATBOX1 | 295 (+) | F286-1.8 | CAAT | tissue-specific expression |
| 43 | CCAATBOX1 | 304 (+) | F286-1.8 | CCAAT | Common sequence found in the 5'-non coding region of eukaryotic genes |
| 44 | CCAATBOX1 | 305 (+) | F286-1.8 | CCAAT | tissue-specific expression |
| 45 | GTGANTG10 | 313 (−) | F286-1.8 | GTGA | Pollen specificity |
| 46 | GTGANTG10 | 325 (−) | F286-1.8 | GTGA | Pollen specificity |
| 47 | RAV1AAT | 334 (+) | F286-1.8 | CAACA | Binding consensus sequence of Arabidopsis transcription factor RAV1 |
| 48 | MYBCORE | 334 (−) | F286-1.8 | CNGTTR | Water stress-related |
| 49 | GT1CONSENSUS | 342 (−) | F286-1.8 | GRWAAW | Binding site in many light regulated genes |
| 50 | IBOXCORE | 343 (−) | F286-1.8 | GATAA | light regulated activities |
| 51 | GATABOX | 344 (−) | F286-1.8 | GATA | Light regulated and tissue-specific expression |
| 52 | CGACGOSAMY3 | 347 (−) | F286-1.8 | CGACG | found in rice Amy3D and Amy3E amylase genes |
| 53 | CAATBOX1 | 381 (−) | F286-1.8 | CAAT | tissue-specific expression |
| 54 | CAATBOX1 | 340 (−) | F286-1.8 | CAAT | tissue-specific expression |
| 55 | -300ELEMENT | 442 (+) | F286-1.8 | TGHAAARK | Endosperm specificity |
| 56 | PROLAMINBOX-OSGL | 442 (+) | F286-1.8 | TGCAAAG | Endosperm specificity |
| 57 | DOFCOREZM | 445 (+) | F286-1.8 | AAAG | tissue-specific expression |
| 58 | CAATBOX1 | 464 (−) | F286-1.8 | CAAT | tissue-specific expression |
| 59 | DOFCOREZM | 472 (+) | F286-1.8 | AAAG | tissue-specific expression |
| 60 | POLLEN1LELAT52 | 473 (−) | F286-1.8 | AGAAA | Pollen specificity |
| 61 | SEF3MOTIFGM | 481 (+) | F286-1.8 | AACCCA | Soybean consensus sequence found in the globulin gene |
| 62 | CAATBOX1 | 501 (+) | F286-1.8 | CAAT | tissue-specific expression |
| 63 | ROOTMOTIFTAPOX1 | 506 (+) | F286-1.8 | ATATTT | Root specificity |
| 64 | SEF1MOTIF | 506 (+) | F286-1.8 | ATATTTAWW | Soybean consensus sequence found in the globulin gene |
| 65 | TATABOXOSPAL | 507 (+) | F286-1.8 | TATTTAA | DNA bending upon binding of OsTBP2, which facilitates transcription of the rice PAL gene (vascular related) |
| 66 | GATABOX | 519 (−) | F286-1.8 | GATA | Light regulated and tissue-specific expression |
| 67 | RAV1AAT | 522 (+) | F286-1.8 | CAACA | Binding consensus sequence of Arabidopsis transcription factor RAV1 |
| 68 | CCA1ATLHCB1 | 523 (+) | F286-1.8 | AAMAATCT | Phytochrome regulation |
| 69 | CAATBOX1 | 525 (+) | F286-1.8 | CAAT | tissue-specific expression |
| 70 | LTRECOREAT-COR15 | 537 (+) | F286-1.8 | CCGAC | Core of low temperature responsive element, stress related |
| 71 | CCAATBOX1 | 541 (+) | F286-1.8 | CCAAT | Common sequence found in the 5'-non coding region of eukaryotic genes |
| 72 | CAATBOX1 | 542 (+) | F286-1.8 | CAAT | tissue-specific expression |
| 73 | GTGANTG10 | 546 (−) | F286-1.8 | GTGA | Pollen specificity |
| 74 | DOFCOREZM | 552 (−) | F286-1.8 | AAAG | tissue-specific expression |
| 75 | SEF3MOTIFGM | 570 (+) | F286-1.8 | AACCCA | Soybean consensus sequence found in the globulin gene |
| 76 | EBOXBNNAPA | 577 (+) | F286-1.8 | CANNTG | Storage protein related |
| 77 | EBOXBNNAPA | 577 (−) | F286-1.8 | CANNTG | Storage protein related |
| 78 | GTGANTG10 | 586 (+) | F286-1.8 | GTGA | Pollen specificity |
| 79 | TBOXATGAPB | 591 (−) | F286-1.8 | ACTTTG | Light regulated |

TABLE 9-continued

Putative regulatory motifs present in the F286 promoter

| # | Regulatory element | Location in F286 promoter | Promoter type | Consensus sequence | Putative regulatory role |
|---|---|---|---|---|---|
| 80 | DOFCOREZM | 592 (+) | F286-1.8 | AAAG | tissue-specific expression |
| 81 | GTGANTG10 | 597 (+) | F286-1.8 | GTGA | Pollen specificity |
| 82 | RAV1AAT | 610 (+) | F286-1.8 | CAACA | Binding consensus sequence of Arabidopsis transcription factor RAV1 |
| 83 | POLLEN1LELAT52 | 643 (−) | F286-1.8 | AGAAA | Pollen specificity |
| 84 | CAATBOX1 | 653 (+) | F286-1.4 | CAAT | tissue-specific expression |
| 85 | CAATBOX1 | 659 (+) | F286-1.4 | CAAT | tissue-specific expression |
| 86 | DOFCOREZM | 690 (−) | F286-1.4 | AAAG | tissue-specific expression |
| 87 | GT1CONSENSUS | 695 (−) | F286-1.4 | GRWAAW | Binding site in many light regulated genes |
| 88 | ROOTMOTIFTAPOX1 | 720 (+) | F286-1.4 | ATATT | Root specificity |
| 89 | CAATBOX1 | 722 (−) | F286-1.4 | CAAT | tissue-specific expression |
| 90 | CCAATBOX1 | 722 (−) | F286-1.4 | CCAAT | Common sequence found in the 5'-non coding region of eukaryotic genes |
| 91 | SEF3MOTIFGM | 724 (−) | F286-1.4 | AACCCA | Soybean consensus sequence found in the globulin gene |
| 92 | GT1CONSENSUS | 728 (−) | F286-1.4 | GRWAAW | Binding site in many light regulated genes |
| 93 | GTGANTG10 | 732 (−) | F286-1.4 | GTGA | Pollen specificity |
| 94 | L1BOXATPDF1 | 751 (+) | F286-1.4 | TAAATGYA | L1 layer-specific gene expression |
| 95 | GATABOX | 757 (−) | F286-1.4 | GATA | Light regulated and tissue-specific expression |
| 96 | DOFCOREZM | 777 (−) | F286-1.4 | AAAG | tissue-specific expression |
| 97 | GTGANTG10 | 780 (−) | F286-1.4 | GTGA | Pollen specificity |
| 98 | DOFCOREZM | 799 (−) | F286-1.4 | AAAG | tissue-specific expression |
| 99 | TAAAGSTKST1 | 799 (−) | F286-1.4 | TAAAG | Guard cell-specific expression |
| 100 | QELEMENTZMZM13 | 816 (−) | F286-1.4 | AGGTCA | pollen specificity |
| 101 | GT1CONSENSUS | 825 (+) | F286-1.4 | GRWAAW | Binding site in many light regulated genes |
| 102 | DOFCOREZM | 854 (+) | F286-1.4 | AAAG | tissue-specific expression |
| 103 | GTGANTG10 | 861 (+) | F286-1.4 | GTGA | Pollen specificity |
| 104 | GT1CONSENSUS | 877 (+) | F286-1.4 | GRWAAW | Binding site in many light regulated genes |
| 105 | CAATBOX1 | 881 (−) | F286-1.4 | CAAT | tissue-specific expression |
| 106 | -10PEHVPSBD | 901 (−) | F286-1.4 | TATTC | Light-responsive promoter element |
| 107 | INRNTPSADB | 915 (+) | F286-1.4 | YTCANTYY | Light responsive transcription |
| 108 | CAATBOX1 | 917 (+) | F286-1.4 | CAAT | tissue-specific expression |
| 109 | MYB2AT | 927 (+) | F286-1.4 | TAACTG | Stress responsive |
| 110 | MYBCORE | 927 (−) | F286-1.4 | CNGTTR | Water stress-related |
| 111 | GATABOX | 940 (+) | F286-1.4 | GATA | Light regulated and tissue-specific expression |
| 112 | ROOTMOTIFTAPOX1 | 941 (+) | F286-1.4 | ATATT | Root specificity |
| 113 | GT1CONSENSUS | 964 (+) | F286-1.4 | GRWAAW | Binding site in many light regulated genes |
| 114 | TATABOX5 | 966 (−) | F286-1.4 | TTATTT | TATA element |
| 115 | GTGANTG10 | 974 (−) | F286-1.4 | GTGA | Pollen specificity |
| 116 | DOFCOREZM | 995 (−) | F286-1.4 | AAAG | tissue-specific expression |
| 117 | INRNTPSADB | 1042 (+) | F286- 1.4 | YTCANTYY | Light responsive transcription |
| 118 | CAATBOX1 | 1044 (+) | F286-1.4 | CAAT | tissue-specific expression |
| 119 | RBCSCONSENSUS | 1045 (+) | F286-1.4 | AATCCAA | rbcS general consensus sequence |
| 120 | INRNTPSADB | 1075 (−) | F286-1.4 | YTCANTYY | Light responsive transcription |
| 121 | RAV1AAT | 1092 (+) | F286-1.0 | CAACA | Binding consensus sequence of Arabidopsis transcription factor RAV1 |
| 122 | GT1CONSENSUS | 1102 (+) | F286-1.0 | GRWAAW | Binding site in many light regulated genes |
| 123 | CAATBOX1 | 1117 (+) | F286-1.0 | CAAT | tissue-specific expression |
| 124 | RAV1AAT | 1156 (+) | F286-1.0 | CAACA | Binding consensus sequence of Arabidopsis transcription factor RAV1 |
| 125 | DOFCOREZM | 1174 (+) | F286-1.0 | AAAG | tissue-specific expression |
| 126 | POLLEN1LELAT52 | 1176 (+) | F286-1.0 | AGAAA | Pollen specificity |
| 127 | CAATBOX1 | 1180 (−) | F286-1.0 | CAAT | tissue-specific expression |
| 128 | CCAATBOX1 | 1180 (−) | F286-1.0 | CCAAT | Common sequence found in the 5'-non coding region of eukaryotic genes |

TABLE 9-continued

Putative regulatory motifs present in the F286 promoter

| # | Regulatory element | Location in F286 promoter | Promoter type | Consensus sequence | Putative regulatory role |
|---|---|---|---|---|---|
| 129 | GATABOX | 1188 (+) | F286-1.0 | GATA | Light regulated and tissue-specific expression |
| 130 | TATA box | 1195 (−) | F286-1.0 | TAAATAA | TATA element |
| 131 | TATABOX5 | 1196 (+) | F286-1.0 | TTATTT | TATA element |
| 132 | CAATBOX1 | 1237 (−) | F286-1.0 | CAAT | tissue-specific expression |
| 133 | GATABOX | 1240 (+) | F286-1.0 | GATA | Light regulated and tissue-specific expression |
| 134 | ROOTMOTIFTAPOX1 | 1241 (+) | F286-1.0 | ATATT | Root specificity |
| 135 | GTGANTG10 | 1253 (−) | F286-1.0 | GTGA | Pollen specificity |
| 136 | ROOTMOTIFTAPOX1 | 1261 (−) | F286-1.0 | ATATT | Root specificity |
| 137 | ROOTMOTIFTAPOX1 | 1262 (+) | F286-1.0 | ATATT | Root specificity |
| 138 | SEF4MOTIFGM7S | 1264 (+) | F286-1.0 | RTTTTTR | Seed specificity |
| 139 | TAAAGSTKST1 | 1269 (+) | F286-1.0 | TAAAG | Guard cell-specific expression |
| 140 | NTBBF1ARROLB | 1269 (−) | F286-1.0 | ACTTTA | tissue-specific expression (including vascular) and auxin induction, found in rolB oncogene |
| 141 | DOFCOREZM | 1270 (+) | F286-1.0 | AAAG | tissue-specific expression |
| 142 | TATABOX4 | 1274 (+) | F286-1.0 | TATATAA | TATA element |
| 143 | ROOTMOTIFTAPOX1 | 1279 (−) | F286-1.0 | ATATT | Root specificity |
| 144 | GATABOX | 1281 (−) | F286-1.0 | GATA | Light regulated and tissue-specific expression |
| 145 | GT1CONSENSUS | 1297 (+) | F286-1.0 | GRWAAW | Binding site in many light regulated genes |
| 146 | TATABOX5 | 1299 (−) | F286-1.0 | TTATTT | TATA element |
| 147 | SEF4MOTIFGM7S | 1302 (−) | F286-1.0 | RTTTTTR | Seed specificity |
| 148 | TATABOX5 | 1312 (−) | F286-1.0 | TTATTT | TATA element |
| 149 | POLASIG3 | 1313 (+) | F286-1.0 | AATAAT | Poly A signal |
| 150 | CAATBOX1 | 1325 (−) | F286-1.0 | CAAT | tissue-specific expression |
| 151 | GATABOX | 1328 (+) | F286-1.0 | GATA | Light regulated and tissue- specific expression |
| 152 | SEF4MOTIFGM7S | 1347 (−) | F286-1.0 | RTTTTTR | Seed specificity |
| 153 | GT1CONSENSUS | 1352 (−) | F286-1.0 | GRWAAW | Binding site in many light regulated genes |
| 154 | MARARS | 1358 (−) | F286-1.0 | WTTTATRTTTW (SEQ ID NO: 32) | "ARS element" found in MAR |
| 155 | ROOTMOTIFTAPOX1 | 1360 (−) | F286-1.0 | ATATT | Root specificity |
| 156 | TATABOX2 | 1362 (+) | F286-1.0 | TATAAAT | TATA box |
| 157 | SEF1MOTIF | 1362 (−) | F286-1.0 | ATATTTAWW | Soybean consensus sequence found in the globulin gene |
| 158 | ROOTMOTIFTAPOX1 | 1366 (−) | F286-1.0 | ATATT | Root specificity |
| 159 | GATABOX | 1368 (−) | F286-1.0 | GATA | Light regulated and tissue- specific expression |
| 160 | ROOTMOTIFTAPOX1 | 1372 (+) | F286-1.0 | ATATT | Root specificity |
| 161 | CAATBOX1 | 1374 (−) | F286-1.0 | CAAT | tissue-specific expression |
| 162 | DOFCOREZM | 1390 (+) | F286-1.0 | AAAG | tissue-specific expression |
| 163 | -10PEHVPSBD | 1392 (+) | F286-1.0 | TATTCT | Light-responsive promoter element |
| 164 | GATABOX | 1398 (+) | F286-1.0 | GATA | Light regulated and tissue- specific expression |
| 165 | ROOTMOTIFTAPOX1 | 1405 (−) | F286-1.0 | ATATT | Root specificity |
| 166 | MYBCORE | 1421 (+) | F286-1.0 | CNGTTR | Water stress-related |
| 167 | RAV1AAT | 1422 (−) | F286-1.0 | CAACA | Binding consensus sequence of Arabidopsis transcription factor RAV1 |
| 168 | MYBPLANT | 1432 (+) | F286-1.0 | MACCWAMC | Plant MYB binding site |
| 169 | REALPHALGLHCB21 | 1433 (+) | F286-1.0 | AACCAA | Phytochrome regulation |
| 170 | 2SSEEDPROTBANAP | 1435 (+) | F286-1.0 | CAAACAC | Conserved in many storage protein |
| 171 | CANBNNAPA | 1435 (+) | F286-1.0 | CNAACAC | Seed specificity |
| 172 | DOFCOREZM | 1477 (+) | F286-1.0 | AAAG | tissue-specific expression |
| 173 | DOFCOREZM | 1483 (+) | F286-1.0 | AAAG | tissue-specific expression |
| 174 | CAATBOX1 | 1495 (+) | F286-1.0 | CAAT | tissue-specific expression |
| 175 | EBOXBNNAPA | 1523 (+) | F286-1.0 | CANNTG | Storage protein related |
| 176 | EBOXBNNAPA | 1523 (−) | F286-1.0 | CANNTG | Storage protein related |
| 177 | DOFCOREZM | 1559 (+) | F286-1.0 | AAAG | tissue-specific expression |
| 178 | POLLEN1LELAT52 | 1561 (+) | F286-1.0 | AGAAA | Pollen specificity |
| 179 | GT1CONSENSUS | 1567 (+) | F286-1.0 | GRWAAW | Binding site in many light regulated genes |

TABLE 9-continued

Putative regulatory motifs present in the F286 promoter

| # | Regulatory element | Location in F286 promoter | Promoter type | Consensus sequence | Putative regulatory role |
|---|---|---|---|---|---|
| 180 | GT1CONSENSUS | 1568 (+) | F286-1.0 | GRWAAW | Binding site in many light regulated genes |
| 181 | INRNTPSADB | 1571 (−) | F286-1.0 | YTCANTYY | Light responsive transcription |
| 182 | CAATBOX1 | 1573 (−) | F286-1.0 | CAAT | tissue-specific expression |
| 183 | _300ELEMENT | 1575 (+) | F286-1.0 | TGHAAARK | Endosperm specificity |
| 184 | DOFCOREZM | 1578 (−) | F286-1.0 | AAAG | tissue-specific expression |
| 185 | INRNTPSADB | 1598 (+) | F286-1.0 | YTCANTYY | Light responsive transcription |
| 186 | CAATBOX1 | 1600 (+) | F286-1.0 | CAAT | tissue-specific expression |
| 187 | POLASIG1 | 1604 (−) | F286-1.0 | AATAAA | Poly A signal |
| 188 | REALPHALGLHCB21 | 1625 (−) | F286-1.0 | AACCAA | Phytochrome regulation |
| 189 | LTRE1HVBLT49 | 1629 (−) | F286-1.0 | CCGAAA | Low temperature responsive element |
| 190 | SEF4MOTIFGM7S | 1645 (−) | F286-1.0 | RTTTTTR | Seed specificity |
| 191 | TATABOX5 | 1648 (−) | F286-1.0 | TTATTT | TATA element |
| 192 | TATABOX4 | 1664 (−) | F286-1.0 | TATATAA | TATA element |
| 193 | TATABOX4 | 1665 (+) | F286-1.0 | TATATAA | TATA element |
| 194 | TATAPVTRNALEU | 1665 (−) | F286-1.0 | TTTATATA | TATA-like motif in plant tRNA gene |
| 195 | SEF4MOTIFGM7S | 1682 (−) | F286-1.0 | RTTTTTR | Seed specificity |
| 196 | TATABOX5 | 1685 (−) | F286-1.0 | TTATTT | TATA element |
| 197 | CAATBOX1 | 1697 (+) | F286-1.0 | CAAT | tissue-specific expression |
| 198 | GATABOX | 1711 (+) | F286-1.0 | GATA | Light regulated and tissue- specific expression |
| 199 | GT1CONSENSUS | 1711 (+) | F286-1.0 | GRWAAW | Binding site in many light regulated genes |
| 200 | IBOXCORE | 1711 (+) | F286-1.0 | GATAA | light regulated activities |
| 201 | SEF4MOTIFGM7S | 1713 (−) | F286-1.0 | RTTTTTR | Seed specificity |
| 202 | ERELEE4 | 1725 (−) | F286-1.0 | AWTTCAAA | Ethylene responsive element |
| 203 | ROOTMOTIFTAPOX1 | 1739 (+) | F286-1.0 | ATATT | Root specificity |
| 204 | GT1CONSENSUS | 1746 (+) | F286-1.0 | GRWAAW | Binding site in many light regulated genes |
| 205 | MARTBOX | 1749 (−) | F286-1.0 | TTWTWTTWTT (SEQ ID NO: 31) | "T-Box" motif found in matrix attachment region |
| 206 | MARTBOX | 1751 (−) | F286-1.0 | TTWTWTTWTT (SEQ ID NO: 31) | "T-Box" motif found in matrix attachment region |
| 207 | TATABOX5 | 1753 (−) | F286-1.0 | TTATTT | TATA element |
| 208 | SEF4MOTIFGM7S | 1756 (−) | F286-1.0 | RTTTTTR | Seed specificity |
| 209 | GT1CONSENSUS | 1761 (−) | F286-1.0 | GRWAAW | Binding site in many light regulated genes |
| 210 | IBOXCORE | 1762 (−) | F286-1.0 | GATAA | light regulated activities |
| 211 | GATABOX | 1763 (−) | F286-1.0 | GATA | Light regulated and tissue- specific expression |
| 212 | EBOXBNNAPA | 1815 (+) | F286-1.0 | CANNTG | Storage protein related |
| 213 | DPBFCOREDCDC3 | 1815 (−) | F286-1.0 | ACACNNG | ABA-responsive and embryo-specification |
| 214 | EBOXBNNAPA | 1816 (−) | F286-1.0 | CANNTG | Storage protein related |
| 215 | -10PEHVPSBD | 1830 (−) | F286-1.0 | TATTCT | Light-responsive promoter element |
| 216 | BOXIINTPATPB | 1833 (+) | F286-1.0 | ATAGAA | found in tobacco plastid atpB gene promoter |
| 217 | RAV1AAT | 1842 (+) | F286-1.0 | CAACA | Binding consensus sequence of Arabidopsis transcription factor RAV1 |
| 218 | DOFCOREZM | 1852 (−) | F286-1.0 | AAAG | tissue-specific expression |
| 219 | TAAAGSTKST1 | 1852 (−) | F286-1.0 | TAAAG | Guard cell-specific expression |
| 220 | DOFCOREZM | 1859 (−) | F286-1.0 | AAAG | tissue-specific expression |
| 221 | WBOXATNPR1 | 1904 (+) | F286-1.0 | TTGAC | "W-box" found in Arabidopsis NPR1 gene |
| 222 | DPBFCOREDCDC3 | 1907 (+) | F286-1.0 | ACACNNG | ABA-responsive and embryo-specification |
| 223 | DPBFCOREDCDC3 | 1910 (−) | F286-1.0 | ACACNNG | ABA-responsive and embryo-specification |
| 224 | GTGANTG10 | 1915 (+) | F286-1.0 | GTGA | Pollen specificity |
| 225 | GTGANTG10 | 1921 (+) | F286-1.0 | GTGA | Pollen specificity |
| 226 | GT1CONSENSUS | 1947 (+) | F286-1.0 | GRWAAW | Binding site in many light regulated genes |
| 227 | INRNTPSADB | 1978 (+) | F286-1.0 | YTCANTYY | Light responsive transcription |
| 228 | GTGANTG10 | 1979 (−) | F286-1.0 | GTGA | Pollen specificity |
| 229 | DOFCOREZM | 1982 (−) | F286-1.0 | AAAG | tissue-specific expression |
| 230 | POLLEN1LELAT52 | 1983 (−) | F286-1.0 | AGAAA | Pollen specificity |
| 231 | CANBNNAPA | 1986 (+) | F286-1.0 | CNAACAC | Seed specificity |
| 232 | DOFCOREZM | 1992 (−) | F286-1.0 | AAAG | tissue-specific expression |
| 233 | GTGANTG10 | 1995 (−) | F286-1.0 | GTGA | Pollen specificity |
| 234 | SEF4MOTIFGM7S | 2008 (−) | F286-1.0 | RTTTTTR | Seed specificity |

TABLE 9-continued

Putative regulatory motifs present in the F286 promoter

| # | Regulatory element | Location in F286 promoter | Promoter type | Consensus sequence | Putative regulatory role |
|---|---|---|---|---|---|
| 235 | DOFCOREZM | 2026 (−) | F286-1.0 | AAAG | tissue-specific expression |
| 236 | TAAAGSTKST1 | 2026 (−) | F286-1.0 | TAAAG | Guard cell-specific expression |
| 237 | DPBFCOREDCDC3 | 2041 (−) | F286-1.0 | ACACNNG | ABA-responsive and embryo-specification |
| 238 | CANBNNAPA | 2044 (−) | F286-1.0 | CNAACAC | Seed specificity |
| 239 | RAV1AAT | 2045 (−) | F286-1.0 | CAACA | Binding consensus sequence of Arabidopsis transcription factor RAV1 |
| 240 | REALPHALGLHCB21 | 2047 (−) | F286-1.0 | AACCCA | Phytochrome regulation |
| 241 | POLLEN1LELAT52 | 2051 (−) | F286-1.0 | AGAAA | Pollen specificity |
| 242 | SEF3MOTIFGM | 2064 (+) | F286-1.0 | AACCCA | Soybean consensus sequence found in the globulin gene |
| 243 | SV40COREENHAN | 2068 (−) | F286-1.0 | GTGGWWHG | SV40 core enhancer |
| 244 | GATABOX | 2096 (−) | F286-1.0 | GATA | Light regulated and tissue-specific expression |
| 245 | DOFCOREZM | 2099 (−) | F286-1.0 | AAAG | tissue-specific expression |
| 246 | GATABOX | 2103 (+) | F286-1.0 | GATA | Light regulated and tissue-specific expression |

Motifs are listed in order of their appearance in the promoter fragments, starting from the 5' end upstream of the F286 coding sequence.
The (+) and (−) in "Location" indicate: for (+), the DNA strand containing the reported F286 promoter sequence; and, for (−), the complementary DNA strand.
The "Promoter Type" indicates that a fragment of that length and all the longer ones will contain the indicated motif.
Motifs found only in the 2.1 kb and 1.8 kb fragments, and not in the shorter 1.4 kb and 1.0 kb ones, are shown in bold.
B: C, G or T;
D: A, G or T;
H: A, C or T;
K: G or T;
M: A or C;
N: A, C, G or T;
R: A or G;
S: C or G;
V: A, C or G;
W: A or T;
Y: C or T.

Figure 9A:
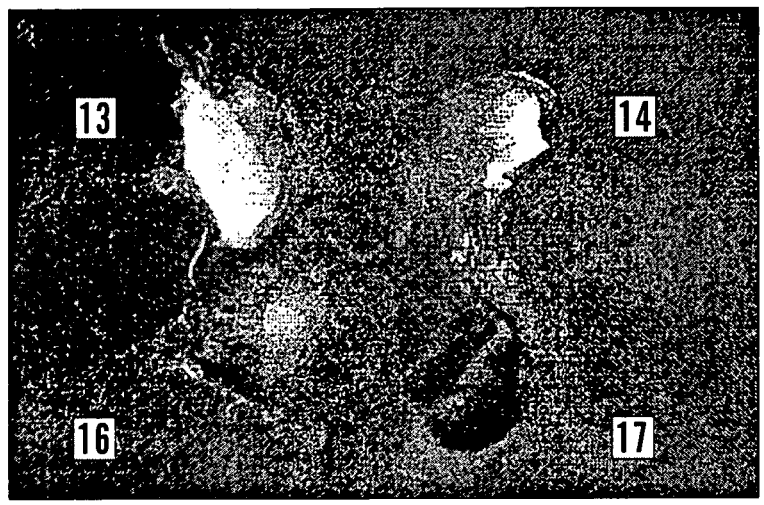
FIGS. 9A–B show cotton seeds with attached fiber from promoter/GUS transformed plants. Seed age (DPA) is noted on the photographs. The 13–17 DPA photograph (FIG. 9A) is from line 1.8-16-17b. The photograph for 21, 27, and 40
Figure 9B:
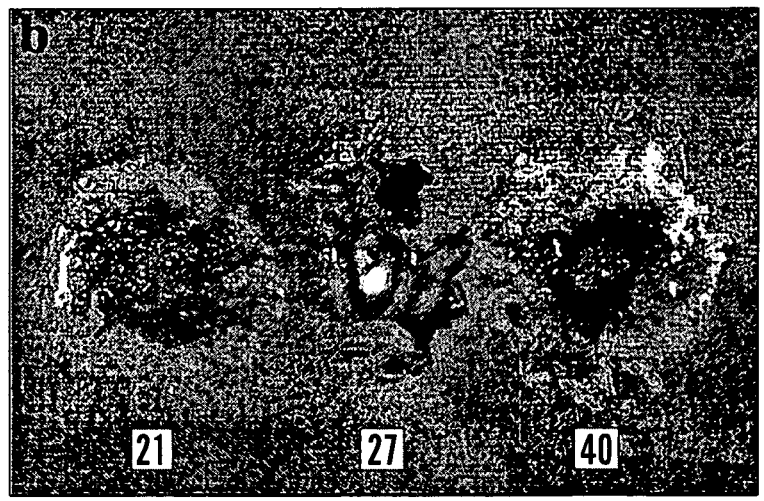

In cotton lint fibers, the promoter drove GUS expression beginning at 14 DPA, with very strong expression by 17 DPA (FIG. 9). Strength of GUS expression in fiber was suggested by the brilliant blue mass of ≧17 DPA fiber observed after ≧30 min incubation in substrate. The non-fiber cells of the outer seed epidermis did not express GUS (FIG. 9; 27 DPA seed). Examination of individual fibers by differential interference contrast (DIC) microscopy showed that the onset of GUS expression corresponds to development of thickened fiber walls containing helical microfibrils, both of which indicate onset of secondary wall deposition. The strong GUS expression at 17 DPA (FIG. 9) likely indicates that all fibers had by then switched to secondary wall deposition, in contrast to a few fibers entering this stage of development between 14–16 DPA. Lint fibers on motes also stained intensely blue by 17 DPA, and microscopic examination confirmed that they had started secondary wall deposition.

The brilliant blue color persisted in living fibers through at least 40 DPA (FIG. 9). Continued GUS expression during this period based was expected based on the expression pattern shown by Northern blots for the F285/F286 genes. These homologous genes were expressed from 15–31 DPA (the last day tested), and histological analysis of GUS was consistent with that finding. Also, quantitative results showed that the amount of GUS increased between 18 and 24 DPA for all three promoter lengths.

GUS was not expressed in linters (also called fuzz fibers) at 27 DPA (FIG. 10). Linters initiate elongation a few days later than lint fibers. Linters manufacture thick cellulosic walls and represent a significant carbon sink (Berlin, "The Outer Epidermis of the Cotton Seed," In: Mauney et al. (eds) Cotton Physiology, pp. 375–414, The Cotton Foundation, Memphis (1986), which is hereby incorporated in its entirety). Changes in cotton fiber quality, especially those requiring more carbon allocation, are preferentially directed to the more valuable lint fibers, and the F286 promoter(s) has additional utility by providing a tool to meet this goal.

In mature T0 plants and/or juvenile T1 plants, GUS was expressed in other secondary walled cells including: (a) those in the inner integument of the seed coat; (b) trichomes on leaves, stems, and developing sepals within young buds; (c) thick-walled vascular cells (in xylem and phloem) of stems, hypocotyls, roots, and the staminal column; (d) the fibrous endothecium of anthers; and (e) the thick cellulosic intine of pollen walls. Xylem tissue separated from a hand section at the cambium and observed in face view clearly showed selective, positive HUS staining in elongated files of fibers. The expression was transient in some cases: older/mature trichomes and vascular cells did not stain positively and sometimes an organ was entirely negative, presumably because it was not growing. Expression intensity in side branches increased as distance away from the main stem increased, which is consistent with increased expression in rapidly growing regions where more secondary walls are forming. There was a consistent linkage between positive staining in cotton fiber and positive staining in vegetative tissues—one was not observed without the other.

No GUS expression was observed in leaf cells other than trichomes despite examination of leaves at many ages (beginning in growing buds) and clearing of chlorophyll in EtOH so that faint blue staining would not be missed. No GUS expression was observed in petal or leaf vascular cells or guard cells (both with secondary walls). The same negative results were obtained for cotyledons and bracts. Guard cells on the seed surface also remained unstained.

Embedding and section of tissue processed for GUS activity confirmed the specific association of promoter activity with cells that were producing thick secondary cell walls (FIG. 11).

Qualitative GUS expression intensity was ranked as 2.1 kb >1.4 kb >1.8 kb, which was consistent with quantitative results. Preliminary results from the 1.0 kb test showed that GUS expression in vegetative and reproductive tissues can be of similar intensity to the three longer promoter fragments. Combining results from mature (m) and juvenile plants (j), qualitative GUS expression intensity in different tissues was: roots (j)>petioles (m)>hypocotyls (j)>side-branches (m)>main-stems (m & j). However, these results may have little relation to expression levels within cells and more relation to the density of secondary-wall-forming cells within a tissue. The data suggested that promoter function was stronger in cotton fiber than in these other fibers because strong staining in cotton fiber at ≧17 DPA was observed in <1 h, whereas ≧4 h was empirically determined as usually necessary for obtaining visible blue color in vegetative tissues (FIG. 12A; a typical result in a moderate-level expressing line). An exception occurred in the strongly expressing line 2.2–47 (see below for quantitative results) where blue color was observed in other tissues after 1 hour (FIG. 12B), but the behavior of the moderate-level expressors is more useful for comparing strength of expression between tissues histologically. Therefore, the F286 promoter(s) had the most highly enhanced expression in cotton lint fiber.

Example 11

Quantitative Methods and Results

Kanamycin-resistant T1 seedlings, as described above, were grown in a greenhouse until flowering. White flowers were tagged on the day of anthesis, and normal-sized bolls were harvested at 18–24 DPA. It was proven that bolls could be snap-frozen in liquid nitrogen and stored at −80° C. without visibly minimizing the histological GUS reaction. Quantitative tests showed that values from frozen bolls were higher, probably because of proteolytic activity that occurred while fresh fibers were cut up with scissors to facilitate GUS extraction. Therefore, the histological and quantitative assays were run in batches from previously collected frozen bolls.

Frozen bolls were cracked open, seeds were separated from boll tissue, and fiber was separated from all of the seeds by gentle grinding before the fibers alone were pulverized by hard grinding under liquid nitrogen. All seeds used in the test were of typical size with typical fiber for their age. Extraction and assay of GUS was as described in Gallagher, (ed) "Gus Protocols: Using the GUS Gene as a Reporter of Gene Expression," 221 pp., Academic Press, New York (1992), which is hereby incorporated by reference in its entirety. GUS activity was measured with the fluorometric substrate 4-methylumbelliferyl-β-D-glucuronide (MUG). MUG is hydrolyzed by GUS, and the reaction is terminated with basic 0.2M $Na_2CO_3$. The carbonate also causes the released moiety, 7-hydroxy-4-methylcoumarin (4-methylumbelliferone; MU) to become fully fluorescent. MU fluorescence was measured in a fluorometer (355 nm excitation/460 nm emission). A standard curve was prepared with purified GUS [type VII-A from $E.\ coli$; Sigma Chem; 0.2–2.0 ng/μl), and protein content was determined in the cotton fiber extracts by Bradford assay to allow expression of data as % GUS in Total Protein. Using purified GUS, it was determined that no quenching of the reaction was caused by endogenous components of cotton fiber extracts. As a control, the assay was performed on fibers of untransformed cotton, and the background value corresponding to 0.112% GUS in total protein was subtracted from all reported values.

On 18 DPA, one day after uniform blue was observed in fibers, the 1.4, 1.8, and 2.1 kb tests showed similar means for Avg % GUS/plant (TABLE 10). The individual data sets contained largely overlapping values. As an exception, the highest values (1.256 and 1.357% GUS) were observed for two individual plants in the 2.1 test, 2.1-2-2a-1 and 2.1-47-1a-1. These lines showed T1 segregation counts at T1 of 14:0 and 19:0, respectively, which indicates multiple gene insertion sites. Other plants tested within each of these lines had lower levels of GUS, consistent with their having fewer copies of the foreign gene expression cassette. Therefore, the 2.1 kb promoter may drive highest protein expression when present within multiple copies of an expression cassette. The 2.1 kb promoter may be a preferred length to drive highest gene expression. Both the 1.4 and 1.8 kb tests included lines with T1 segregation counts showing multiple gene insertion sites (e.g. 1.4-32-2a, 1.4-41-6a, and 1.8-16-11a), and the number of 1.4 kb lines tested gave the same chance as for the 2.1 kb test for high expression to show up. However, it is possible that plants with the highest copy numbers of the 1.4 and 1.8 kb cassettes were not tested due to the random way seedlings were placed into the tests (based only on Kanamycin resistance of lateral root formation). Lines with segregation counts generally consistent with one gene insertion site (e.g. 1.4-11-3b, 5b; 1.4-32-1a; 1.4-43-5a; 1.4-44-1a, 1.8-16-12a, 2.1-2-3a, 2.2-55-8a) had a range of individual plant GUS % of 0.187–0.756, with no obvious differences between the 1.4, 1.8, and 2.1 kb tests. These values presumably arose from one or two copies of the foreign gene expression cassette in the segregating T1 populations.

TABLE 10

Quantitative Analysis of GUS as % GUS in Total Protein

| Line | T1 Plant | | | DPA | % GUS in Protein | Avg % GUS/ plant | Avg % GUS/ embryo | Avg % GUS/ test | T1 Seg Counts |
|---|---|---|---|---|---|---|---|---|---|
| 1.4 | 2 | 8 | a | 2 | 18 | 0.289 | | | 2:4 |
| 1.4 | 2 | 8 | a | 2 | 18 | 0.197 | 0.243 | 0.243 | |
| 1.4 | 8 | 14 | a | 1 | 18 | 0.582 | | | 8:4 |
| 1.4 | 8 | 14 | a | 1 | 18 | 0.397 | 0.490 | 0.490 | |
| 1.4 | 11 | 3 | b | 1 | 18 | 0.806 | | | 11:5 |
| 1.4 | 11 | 3 | b | 1 | 18 | 0.705 | 0.756 | 0.756 | |
| 1.4 | 11 | 5 | b | 2 | 18 | 0.445 | | | 10:6 |
| 1.4 | 11 | 5 | b | 2 | 18 | 0.779 | 0.612 | 0.612 | |
| 1.4 | 32 | 1 | a | 1 | 18 | 0.471 | | | 13:5 |
| 1.4 | 32 | 1 | a | 1 | 18 | 0.481 | 0.476 | | |
| 1.4 | 32 | 1 | a | 2 | 18 | 0.401 | | | |
| 1.4 | 32 | 1 | a | 2 | 18 | 0.425 | 0.413 | 0.444 | |
| 1.4 | 32 | 2 | a | 1 | 18 | 0.577 | | | 14:1 |
| 1.4 | 32 | 2 | a | 1 | 18 | 0.646 | 0.612 | | |
| 1.4 | 32 | 2 | a | 2 | 18 | 0.547 | | | |
| 1.4 | 32 | 2 | a | 2 | 18 | 0.403 | 0.475 | 0.544 | |
| 1.4 | 34 | 5 | a | 1 | 18 | 0.187 | 0.187 | 0.187 | 17:5 |
| 1.4 | 34 | 7 | a | 1 | 18 | 0.348 | 0.348 | | 4:5 |
| 1.4 | 34 | 7 | a | 2 | 18 | 0.475 | 0.475 | 0.412 | |
| 1.4 | 36 | 3 | a | 1 | 18 | 0.141 | | | 3:11 |
| 1.4 | 36 | 3 | a | 1 | 18 | 0.192 | 0.167 | 0.167 | |
| 1.4 | 41 | 6 | a | 2 | 18 | 0.676 | | | 11:1 |
| 1.4 | 41 | 6 | a | 2 | 18 | 0.439 | | | |
| 1.4 | 41 | 6 | a | 2 | 18 | 0.574 | 0.563 | 0.563 | |
| 1.4 | 41 | 7 | a | 1 | 18 | 0.525 | | | |
| 1.4 | 41 | 7 | a | 1 | 18 | 0.556 | 0.540 | 0.540 | |
| 1.4 | 44 | 1 | a | 1 | 18 | 0.658 | | | 11:3 |
| 1.4 | 44 | 1 | a | 1 | 18 | 0.559 | 0.608 | 0.608 | 0.464 |
| 1.8 | 8 | 3 | a | 1 | 18 | 0.516 | 0.516 | | 4:5 |
| 1.8 | 8 | 3 | a | 2 | 18 | 0.110 | | | |
| 1.8 | 8 | 3 | a | 2 | 18 | 0.180 | 0.145 | 0.330 | |
| 1.8 | 8 | 17 | a | 1 | 18 | 0.236 | 0.236 | 0.236 | 5:5 |
| 1.8 | 16 | 11 | a | 2 | 18 | 0.482 | | | 17:1 |
| 1.8 | 16 | 11 | a | 2 | 18 | 0.376 | | | |
| 1.8 | 16 | 11 | a | 2 | 18 | 0.660 | 0.506 | 0.506 | |
| 1.8 | 16 | 12 | a | 1 | 18 | 0.292 | | | 14:3 |
| 1.8 | 16 | 12 | a | 1 | 18 | 0.373 | 0.332 | | |
| 1.8 | 16 | 12 | a | 2 | 18 | 0.442 | | | |
| 1.8 | 16 | 12 | a | 2 | 18 | 0.467 | 0.455 | 0.394 | 0.367 |
| 2.1 | 2 | 2 | a | 1 | 18 | 1.331 | | | 14:0 |
| 2.1 | 2 | 2 | a | 1 | 18 | 1.181 | 1.256 | | |
| 2.1 | 2 | 2 | a | 2 | 18 | 0.451 | | | |
| 2.1 | 2 | 2 | a | 2 | 18 | 0.573 | 0.512 | 0.884 | |
| 2.1 | 2 | 3 | a | 2 | 18 | 0.603 | 0.603 | 0.603 | 13:5 |
| 2.1 | 28 | 1 | a | 2 | 18 | 0.176 | 0.176 | 0.176 | 3:7 |
| 2.1 | 28 | 3 | b | 2 | 18 | 0.275 | 0.275 | 0.275 | 9:4 |
| 2.1 | 38 | 4 | a | 1 | 18 | 0.227 | 0.227 | 0.227 | 5:1 |
| 2.1 | 39 | 13 | a | 2 | 18 | 0.444 | | | 5:1 |
| 2.1 | 39 | 13 | a | 2 | 18 | 0.380 | 0.412 | 0.412 | |
| 2.1 | 47 | 1 | a | 1 | 18 | 1.351 | | | 19:0 |
| 2.1 | 47 | 1 | a | 1 | 18 | 1.363 | 1.357 | | |
| 2.1 | 47 | 1 | a | 2 | 18 | 0.937 | | | |
| 2.1 | 47 | 1 | a | 2 | 18 | 0.690 | 0.813 | 1.085 | |
| 2.1 | 47 | 4 | a | 1 | 18 | 0.587 | | | 14:1 |
| 2.1 | 47 | 4 | a | 1 | 18 | 0.692 | 0.640 | 0.640 | |
| 2.1 | 55 | 8 | a | 1 | 18 | 0.407 | 0.407 | | 17:5 |
| 2.1 | 55 | 8 | a | 2 | 18 | 0.573 | 0.573 | 0.490 | |
| 2.1 | 55 | 10 | a | 1 | 18 | 0.378 | | | 18:3 |
| 2.1 | 55 | 10 | a | 1 | 18 | 0.421 | 0.399 | 0.399 | |
| 2.1 | 93 | 1 | a | 1 | 18 | 0.387 | 0.387 | 0.387 | 4:12 |
| 2.1 | 101 | 1 | b | 1 | 18 | 0.728 | | | 4:0 |
| 2.1 | 101 | 1 | b | 1 | 18 | 0.713 | 0.720 | 0.720 | 0.525 |

TABLE 10-continued

Quantitative Analysis of GUS as % GUS in Total Protein

| 35S | 25 | 16 |   | 1 | 18 | 2.463 |       |       |       |
|-----|----|----|---|---|----|-------|-------|-------|-------|
| 35S | 25 | 16 |   | 1 | 18 | 2.288 | 2.375 |       |       |
| 35S | 25 | 16 |   | 3 | 18 | 1.974 |       |       |       |
| 35S | 25 | 16 |   | 3 | 18 | 2.437 | 2.205 | 2.290 |       |
| 35S | 30 | 11 |   | 2 | 18 | 1.817 |       |       |       |
| 35S | 30 | 11 |   | 2 | 18 | 2.226 | 2.022 | 2.022 |       |
| 35S | 39 | 17 |   | 1 | 18 | 1.958 | 1.958 |       |       |
| 35S | 39 | 17 |   | 2 | 18 | 1.037 |       |       |       |
| 35S | 39 | 17 |   | 2 | 18 | 1.089 | 1.063 | 1.510 | 1.940 |

| Line |    |    |   | T1 Plant | DPA | % GUS in Protein | Avg % GUS/ plant | Avg % GUS/ embryo | Avg % GUS/ test | T1 Seg Counts (repeat) |
|------|----|----|---|----------|-----|------------------|------------------|-------------------|-----------------|------------------------|
| 1.4  | 2  | 8  | a | 1        | 24  | 1.217            | 1.217            |                   |                 | 2:4                    |
| 1.4  | 11 | 3  | b | 1        | 24  | 1.271            | 1.271            | 1.271             |                 | 11:5                   |
| 1.4  | 32 | 1  | a | 2        | 24  | 0.598            | 0.598            | 0.598             |                 | 13:5                   |
| 1.4  | 32 | 2  | a | 2        | 24  | 0.731            | 0.731            | 0.731             |                 | 14:1                   |
| 1.4  | 34 | 7  | a | 2        | 24  | 0.711            | 0.711            | 0.711             |                 | 4:5                    |
| 1.4  | 36 | 3  | a | 1        | 24  | 0.510            | 0.510            | 0.510             |                 | 3:11                   |
| 1.4  | 41 | 6  | a | 2        | 24  | 0.497            | 0.497            | 0.497             |                 |                        |
| 1.4  | 44 | 1  | a | 1        | 24  | 0.518            | 0.518            | 0.518             | 0.757           | 11:3                   |
| 1.8  | 16 | 12 | a | 1        | 24  | 0.508            | 0.508            |                   |                 | 14:3                   |
| 1.8  | 16 | 12 | a | 2        | 24  | 0.765            | 0.765            | 0.636             | 0.636           |                        |
| 2.1  | 2  | 2  | a | 1        | 24  | 0.845            |                  |                   |                 | 14:0                   |
| 2.1  | 2  | 2  | a | 1        | 24  | 1.171            | 1.008            | 1.008             |                 |                        |
| 2.1  | 39 | 13 | a | 2        | 24  | 0.356            | 0.356            | 0.356             |                 | 5:1                    |
| 2.1  | 47 | 1  | a | 1        | 24  | 1.142            | 1.142            |                   |                 | 19:0                   |
| 2.1  | 47 | 1  | a | 2        | 24  | 1.341            | 1.341            | 1.241             |                 |                        |
| 2.1  | 47 | 4  | a | 1        | 24  | 0.602            |                  |                   |                 |                        |
| 2.1  | 47 | 4  | a | 1        | 24  | 1.095            | 0.848            |                   |                 |                        |
| 2.1  | 47 | 4  | a | 2        | 24  | 0.846            | 0.846            | 0.847             |                 |                        |
| 2.1  | 55 | 10 | a | 1        | 24  | 0.491            | 0.491            | 0.491             |                 | 18:3                   |
| 2.1  | 101| 1  | b | 1        | 24  | 0.927            | 0.927            | 0.927             | 0.812           | 4:0                    |
| 35S  | 25 | 16 |   | 1        | 24  | 0.864            |                  |                   |                 |                        |
| 35S  | 25 | 16 |   | 1        | 24  | 1.271            | 1.068            |                   |                 |                        |
| 35S  | 25 | 16 |   | 2        | 24  | 1.539            | 1.539            | 1.304             |                 |                        |
| 35S  | 30 | 11 |   | 2        | 24  | 1.120            | 1.120            | 1.120             | 1.212           |                        |

A line name, e.g. 1.4-2-8a, has the following components: '1.4' = the length of the F286 promoter used for the transformation. '2' = a unique piece of callus. '8a' = a particular embryo arising from that piece of callus. Multiple embryos from the same line may or may not represent the same transformation event.
Alternating gray shading highlights different transgenic lines.
T1 Seg Counts = Kan-Resistant: Kan Sensitive from lateral root formation on Kanamycin medium.

On 18 DPA, the 35S CaMV promoter test showed 3.70–5.29 times higher % GUS than any length of the F286 promoter tested (TABLE 11). However, this result is not an indication of relative promoter strength, since the 35S CaMV promoter drives gene expression from the very beginning of cotton fiber development, as demonstrated by its use as a control promoter in previous experiments (Dang, "Expression of a Cotton Fiber 'Specific' Gene Promoter in Tobacco and Cotton," 96 pp., Ph.D. dissertation, Texas Tech University, Lubbock, Tex. (1996), which is hereby incorporated by reference in its entirety). Consequently, the gusA gene has been turned on for 18 days in the fiber from the 35S CaMV test, but uniformly for only one day in the F286 promoter tests. As previously described, the GUS protein is very stable and accumulates over time, making it difficult to distinguish between earlier onset of transcription and stronger promoter activity. However, the 1.4, 1.8, and 2.1 kb F286 promoter tests showed increased % GUS (average=0.283% increase) between 18 DPA and 24 DPA, whereas the 35S CaMV promoter test showed a decrease over the same period (−0.728%). Therefore, in addition to restricting gene expression to the secondary wall stage of the fiber development, the F286 promoters are preferred to maintain more consistent levels of gene expression for a longer period of secondary wall deposition.

TABLE 11

Means for % GUS in Total Protein on 18 and 24 DPA for 3 lengths of the F286 promoter and the 35S CaMV promoter

| | Promoter Tested | | | |
|---|---|---|---|---|
| DPA | F286-2.1 kb | F286-1.8 kb | F286-1.4 kb | 35S CaMV |
| 18 | 0.525 | 0.367 | 0.464 | 1.940 |
| 24 | 0.812 | 0.636 | 0.757 | 1.212 |
| Percent change | +0.287% | +0.269% | +0.293% | −0.728% |

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA promoter suitable for inducing expression of a protein encoded by a second DNA operably associated with the DNA promoter, said DNA promoter being isolated from cotton and suitable for driving expression preferentially in secondary walled cells during secondary wall deposition, wherein the DNA promoter comprises the nucleotide sequence of SEQ ID NO: 8.

2. A DNA construct comprising:
   a DNA promoter suitable for inducing expression of a protein encoded by a second DNA operably associated with the DNA promoter, said DNA promoter being isolated from cotton and suitable for driving expression preferentially in secondary walled cells during secondary wall deposition;
   a second DNA encoding a protein or polypeptide, wherein the DNA promoter is operably linked 5' to the second DNA to induce transcription of the second DNA; and
   a 3' regulatory region operably linked to the second DNA, wherein the DNA promoter comprises the nucleotide sequence of SEQ ID NO: 8.

* * * * *

SEQUENCE LISTING

<160> NUMBER OF SEQ ID NOS: 32

<210> SEQ ID NO 1
<211> LENGTH: 957
<212> TYPE: DNA
<213> ORGANISM: Gossypium hirsutum

<400> SEQUENCE: 1

```
atggaggcca aatggctgct atgttttaca atggcagcac taatggcagt gtcaaatggc      60
caggaatcag tgaagccatt ggtgaagata gttaaaggca agaaactttg gataaaggg     120
tgggaatgta aagggtggtc acagttttgt tgtaaccaaa ccatttctga ttatttccga    180
acttatcaat ttgagaacct tttcgctaaa cgtaatacac cggtggcaca tgcggttggg    240
ttctgggatt accattcttt cattacggcg gcggctcagt atcagcctca tggttttggt    300
accaccggcg gtaagctgca gagcatgaag gaagtggcag cttttcttgg acatgtcggc    360
agcaaaactt catgtggtta tggagtggca actgggggac cattggcttg ggtctatgc    420
tacaacaagg aaatgagtcc tagcaaattg tattgtgatg attactacaa atacacctac    480
ccttgcactc ctggagtttc ttaccatggc cgtggtgcct tgcctatcta ttggaactac    540
aactatggag aaacaggcga cgcattgaag gtggacttat tgaaccaccc tgaatacata    600
gaaaacaatg caaccttagc tttccaggca gcactctgga gatggatgac accggtgaag    660
aaacaccaac cgtcggccca cgacgtgttt gtcggcagct ggaaaccgac caagaacgac    720
acgttggcca gcgggtcccc ggggtttgga gccaccatga atgtgctcta tggagatcaa    780
gtttgtgggc gaggtgatgt tgacaccatg aacaacatca tctctcatta cctttcttac    840
cttgacctaa tgggagttgg gagagaagag gcaggacccc atgaagtgct cacatgtgaa    900
gaacaaaagc ctttcactgt atctccttct tctgcatcat catcatcatc atcttga       957
```

<210> SEQ ID NO 2
<211> LENGTH: 318
<212> TYPE: PRT
<213> ORGANISM: Gossypium hirsutum

<400> SEQUENCE: 2

```
Met Glu Ala Lys Trp Leu Leu Cys Phe Thr Met Ala Ala Leu Met Ala
 1               5                  10                  15

Val Ser Asn Gly Gln Glu Ser Val Lys Pro Leu Val Lys Ile Val Lys
            20                  25                  30

Gly Lys Lys Leu Cys Asp Lys Gly Trp Glu Cys Lys Gly Trp Ser Gln
        35                  40                  45

Phe Cys Cys Asn Gln Thr Ile Ser Asp Tyr Phe Arg Thr Tyr Gln Phe
    50                  55                  60

Glu Asn Leu Phe Ala Lys Arg Asn Thr Pro Val Ala His Ala Val Gly
65                  70                  75                  80

Phe Trp Asp Tyr His Ser Phe Ile Thr Ala Ala Gln Tyr Gln Pro
                85                  90                  95

His Gly Phe Gly Thr Thr Gly Gly Lys Leu Gln Ser Met Lys Glu Val
            100                 105                 110

Ala Ala Phe Leu Gly His Val Gly Ser Lys Thr Ser Cys Gly Tyr Gly
        115                 120                 125

Val Ala Thr Gly Gly Pro Leu Ala Trp Gly Leu Cys Tyr Asn Lys Glu
    130                 135                 140
```

```
Met Ser Pro Ser Lys Leu Tyr Cys Asp Asp Tyr Lys Tyr Thr Tyr
145                 150                 155                 160

Pro Cys Thr Pro Gly Val Ser Tyr His Gly Arg Gly Ala Leu Pro Ile
                165                 170                 175

Tyr Trp Asn Tyr Asn Tyr Gly Glu Thr Gly Asp Ala Leu Lys Val Asp
            180                 185                 190

Leu Leu Asn His Pro Glu Tyr Ile Glu Asn Asn Ala Thr Leu Ala Phe
        195                 200                 205

Gln Ala Ala Leu Trp Arg Trp Met Thr Pro Val Lys Lys His Gln Pro
    210                 215                 220

Ser Ala His Asp Val Phe Val Gly Ser Trp Lys Pro Thr Lys Asn Asp
225                 230                 235                 240

Thr Leu Ala Lys Arg Val Pro Gly Phe Gly Ala Thr Met Asn Val Leu
                245                 250                 255

Tyr Gly Asp Gln Val Cys Gly Arg Gly Asp Val Asp Thr Met Asn Asn
            260                 265                 270

Ile Ile Ser His Tyr Leu Ser Tyr Leu Asp Leu Met Gly Val Gly Arg
        275                 280                 285

Glu Glu Ala Gly Pro His Glu Val Leu Thr Cys Glu Glu Gln Lys Pro
    290                 295                 300

Phe Thr Val Ser Pro Ser Ser Ala Ser Ser Ser Ser Ser
305                 310                 315

<210> SEQ ID NO 3
<211> LENGTH: 951
<212> TYPE: DNA
<213> ORGANISM: Gossypium hirsutum

<400> SEQUENCE: 3
atggaagcca aatggctggt tcttttttca gtggcggcaa tgctggtggc actggccaac      60
tgccaggaat cgttgaagcc attggtgaag atggtaaagg gcaagaagct gtgtgacaaa     120
gggtgggaat gtaaagggtg gtcaaagtat tgttgcaacc ataccatttc tgattacttc     180
caaacttacc agtttgagga ccttttttgcg aagcgtaaca cgccggtagc acatgcggtt     240
gggttctggg attaccattc cttcattact gctgctgctc agtatcagcc tcatggattt     300
ggtaccaccg gggaaaagct ccagaatatg aaggaagtcg ctgctttttct ggacatgtc      360
ggcagcaaaa cttcatgtgg ctatggagtc gctaccgggg gaccattggc ttggggtctt     420
tgctacaaca agaaaatgag ccctagcaaa atatattgcg atgattacta taaatacacc     480
tatccttgca caccaggagt ctcatatcat ggccgtggtg ccttgcctat ctactggaac     540
tacaactatg gggaaactgg agaggctttg aaggtggact tgttgaacca cccagaatac     600
ttagaagaca acgcaacctt ggctttccag acagcaatgt ggaggtggat gacgccgatg     660
aagaaacacc aaccctcagc ccatgacgtt tcgttggca actggaaacc aaccaagaac      720
gacaccttgg ccaagagggt tccaggtttt ggaaccacca tgaatgttct ttatggtgac     780
caagtttgtg gtcaaggtga tagtgattcc atgaacaata tgatctctca ttacctttat     840
taccttgacc ttttgggagt tggccgagaa gaagctggtc ctcatgatat gctcacctgt     900
gaagaacaag aacccttcac tgtttctccc tcatctgcaa catcatcatg a               951

<210> SEQ ID NO 4
<211> LENGTH: 316
<212> TYPE: PRT
<213> ORGANISM: Gossypium hirsutum
```

```
<400> SEQUENCE: 4

Met Glu Ala Lys Trp Leu Val Leu Phe Ser Val Ala Ala Met Leu Val
  1               5                  10                  15

Ala Leu Ala Asn Cys Gln Glu Ser Leu Lys Pro Leu Val Lys Met Val
             20                  25                  30

Lys Gly Lys Lys Leu Cys Asp Lys Gly Trp Glu Cys Lys Gly Trp Ser
         35                  40                  45

Lys Tyr Cys Cys Asn His Thr Ile Ser Asp Tyr Phe Gln Thr Tyr Gln
     50                  55                  60

Phe Glu Asp Leu Phe Ala Lys Arg Asn Thr Pro Val Ala His Ala Val
 65                  70                  75                  80

Gly Phe Trp Asp Tyr His Ser Phe Ile Thr Ala Ala Gln Tyr Gln
                 85                  90                  95

Pro His Gly Phe Gly Thr Thr Gly Glu Lys Leu Gln Asn Met Lys Glu
                100                 105                 110

Val Ala Ala Phe Leu Gly His Val Gly Ser Lys Thr Ser Cys Gly Tyr
            115                 120                 125

Gly Val Ala Thr Gly Gly Pro Leu Ala Trp Gly Leu Cys Tyr Asn Lys
        130                 135                 140

Glu Met Ser Pro Ser Lys Ile Tyr Cys Asp Asp Tyr Tyr Lys Tyr Thr
145                 150                 155                 160

Tyr Pro Cys Thr Pro Gly Val Ser Tyr His Gly Arg Gly Ala Leu Pro
                165                 170                 175

Ile Tyr Trp Asn Tyr Asn Tyr Gly Glu Thr Gly Glu Ala Leu Lys Val
                180                 185                 190

Asp Leu Leu Asn His Pro Glu Tyr Leu Glu Asp Asn Ala Thr Leu Ala
            195                 200                 205

Phe Gln Thr Ala Met Trp Arg Trp Met Thr Pro Met Lys Lys His Gln
        210                 215                 220

Pro Ser Ala His Asp Val Phe Val Gly Asn Trp Lys Pro Thr Lys Asn
225                 230                 235                 240

Asp Thr Leu Ala Lys Arg Val Pro Gly Phe Gly Thr Thr Met Asn Val
                245                 250                 255

Leu Tyr Gly Asp Gln Val Cys Gly Gln Gly Asp Ser Asp Ser Met Asn
                260                 265                 270

Asn Met Ile Ser His Tyr Leu Tyr Tyr Leu Asp Leu Leu Gly Val Gly
            275                 280                 285

Arg Glu Glu Ala Gly Pro His Asp Met Leu Thr Cys Glu Glu Gln Glu
        290                 295                 300

Pro Phe Thr Val Ser Pro Ser Ser Ala Thr Ser Ser
305                 310                 315

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence:  Consensus
      sequence

<400> SEQUENCE: 5

Gly Arg Gly Ala Leu Pro Ile Tyr Trp Asn Tyr Asn Tyr Gly Glu Thr
  1               5                  10                  15

Gly Asp Ala Leu
             20
```

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Consensus sequence

<400> SEQUENCE: 6

Met Lys Glu Val Ala Ala Phe Leu Gly His Val Gly Ser Lys Thr Ser
 1               5                  10                  15
Cys Gly Tyr Gly Val Ala Thr Gly Gly Pro Leu Ala Trp Gly Leu Cys
            20                  25                  30
Tyr Asn Lys Glu Met Ser Pro
        35

<210> SEQ ID NO 7
<211> LENGTH: 1029
<212> TYPE: DNA
<213> ORGANISM: Gossypium hirsutum

<400> SEQUENCE: 7
ctgagaccag cgttcaacat cgatgaaaat ttgttttaac aatgagaact gcaaatcctc      60
catagtcttc taacatttca acattcgaaa tctcgaaaag aaattggctt gatatgattt     120 atttaggtg ttaattttat gtattataat aatgcacaaa ttgatatttt atgcatcaca      180
tttaatattt ttaaagtata taatatcaaa tcattttatg aaaataaaaa taccaaataa     240
tacataaatt gatagttcaa gtatttcatt aaaaattttc aaaatataaa tatcatattg     300
aaacatttta taaagaata gataccaaat atgacatcat cccctgttga gagtaaccaa      360
acactgtttt catccagccc atgagaagta tttggcccaa agcaaaagt ttcagtacaa      420 tgaattatga atcccaaaaa aaccccaagt ggtccaggtc caagccagtc tagggctgag     480
gaaagaaatg gaaaaattga aaagtaattc cagggtctga ttcaattta ttaaatttag      540 tttgattttg gtttcggttc ataaattaa aaataattt aaaatgttat ataaaactgt       600 ttttttaaaaa taaattaatc aataatctaa acgataaaa atggcgattt gaattaagct     660
catattttga aaaaaaaata aaaattatct catccagaac tgattaaaac cgaaccgatg     720
aatcctagaa gccaagccaa gtgtgcagag taagaataga acatcaacat tttgctttaa     780
gcttttcgtt gcttgcactc taagaagcat aaaacgcaag caaaacttga cactagtgtg     840
agtgtgagtg cccatcattc atcaaccctg aaaatcgccc ttcccctaat cagttctaac     900
ctcactttct aacactttca ctgcagcact caaaaacatt cgccgaatct ttactataaa     960
ctcccagtgt tggtttctcc actccaaacc caaaccacga ccaccacatt ttgcttcgta    1020
tctttgata                                                            1029

<210> SEQ ID NO 8
<211> LENGTH: 1403
<212> TYPE: DNA
<213> ORGANISM: Gossypium hirsutum

<400> SEQUENCE: 8
aacctctcga gctgccatat tgggtttttc actacccacc tcttcattaa atgtatcttc      60
aacctctcaa ctcctttcac caccagacga atcttcttta gcaaaatcaa aatgacctta    120
tgaaaattta gcacgtccac ctccagattc aaaggctgtg aatccccaac ttcggaaatt    180
gttcatctcc acattcaaga ataatgagtt cctcaatttg ttttaactga ttagccgata    240

-continued

| | |
|---|---|
| ttaagcgagt tagactccat ggaaataaaa tcaccctaat aaatagcaac gcttttgaac | 300 |
| gtctctaggt tccaagcgtg ctaaggagcg ccagtaactt caatccaagt tgtgcgaaaa | 360 |
| cgtatgaaat ggaactgaga ccagcgttca acatcgatga aaatttgttt taacaatgag | 420 |
| aactgcaaat cctccatagt cttctaacat ttcaacattc gaaatctcga aaagaaattg | 480 |
| gcttgatatg atttatttag ggtgttaatt ttatgtatta taataatgca caaattgata | 540 |
| ttttatgcat cacatttaat attttttaaag tatataatat caaatcattt tatgaaaata | 600 |
| aaaataccaa ataatacata aattgatagt tcaagtattt cattaaaaat tttcaaaata | 660 |
| taaatatcat attgaaacat tttataaaag aatagatacc aaatatgaca tcatcccctg | 720 |
| ttgagagtaa ccaaacactg ttttcatcca gcccatgaga agtatttggc ccaaaagcaa | 780 |
| aagtttcagt acaatgaatt atgaatccca aaaaacccc aagtggtcca ggtccaagcc | 840 |
| agtctagggc tgaggaaaga atggaaaaa ttgaaaagta attccagggt ctgattcaat | 900 |
| tttattaaat ttagtttgat tttggtttcg gttcataaat ttaaaaataa ttttaaaatg | 960 |
| ttatataaaa ctgttttta aaaataaatt aatcaataat ctaaaacgat aaaaatggcg | 1020 |
| atttgaatta agctcatatt ttgaaaaaaa aataaaaatt atctcatcca gaactgatta | 1080 |
| aaaccgaacc gatgaatcct agaagccaag ccaagtgtgc agagtaagaa tagaacatca | 1140 |
| acattttgct ttaagctttt cgttgcttgc actctaagaa gcataaaacg caagcaaaac | 1200 |
| ttgacactag tgtgagtgtg agtgcccatc attcatcaac cctgaaaatc gcccttcccc | 1260 |
| taatcagttc taacctcact ttctaacact ttcactgcag cactcaaaaa cattcgccga | 1320 |
| atctttacta taaactccca gtgttggttt ctccactcca aacccaaacc acgaccacca | 1380 |
| cattttgctt cgtatctttg ata | 1403 |

<210> SEQ ID NO 9
<211> LENGTH: 1815
<212> TYPE: DNA
<213> ORGANISM: Gossypium hirsutum

<400> SEQUENCE: 9

| | |
|---|---|
| cttcaatctc tgccaatgat ctcaccttct tcttcacacc atcaacagta attatcgtcg | 60 |
| aatagggatt atgcactaca gtgttttgca ttgctactcc catggagtcc tccaccctaa | 120 |
| ctctacttgt aggactccta actaacgaat tgcaaagggt ttcgcgaccc gaattgttcc | 180 |
| ctttctgaca acccaagtcc acttaggttc aatcatattt aaattcgtat caacaatctc | 240 |
| ctcagccgac caattcacag ctttcaaatc tgctccgcaa cccaccattt gatcgtgacc | 300 |
| aaagtgtgaa cttgccttca acaaatcagg cccagagcct cgttctaatc atttctcgag | 360 |
| gcaatagcaa tagttgggtc taagttctct gctaattcct ttgatttcct agaacctctc | 420 |
| gagctgccat attgggtttt tcactaccca cctcttcatt aaatgtatct tcaacctctc | 480 |
| aactcctttc accaccagac gaatcttctt tagcaaaatc aaaatgacct tatgaaaatt | 540 |
| tagcacgtcc acctccagat tcaaaggctg tgaatcccca acttcggaaa ttgttcatct | 600 |
| ccacattcaa gaataatgag ttcctcaatt tgttttaact gattagccga tattaagcga | 660 |
| gttagactcc atggaaataa aatcacccta taaatagca acgcttttga acgtctctag | 720 |
| gttccaagcg tgctaaggag cgccagtaac ttcaatccaa gttgtgcgaa aacgtatgaa | 780 |
| atggaactga gaccagcgtt caacatcgat gaaaatttgt tttaacaatg agaactgcaa | 840 |
| atcctccata gtcttctaac atttcaacat tcgaaatctc gaaagaaat tggcttgata | 900 |
| tgatttattt agggtgttaa ttatgtat tataataatg cacaaattga tatttatgc | 960 |

-continued

| | | | | |
|---|---|---|---|---|
| atcacattta | atattttaa | agtatataat | atcaaatcat | tttatgaaaa taaaaatacc | 1020 |
| aaataataca | taaattgata | gttcaagtat | ttcattaaaa | attttcaaaa tataaatatc | 1080 |
| atattgaaac | attttataaa | agaatagata | ccaaatatga | catcatcccc tgttgagagt | 1140 |
| aaccaaacac | tgttttcatc | cagcccatga | gaagtatttg | gcccaaaagc aaaagtttca | 1200 |
| gtacaatgaa | ttatgaatcc | caaaaaaacc | ccaagtggtc | caggtccaag ccagtctagg | 1260 |
| gctgaggaaa | gaaatggaaa | aattgaaaag | taattccagg | gtctgattca attttattaa | 1320 |
| atttagttg | attttggttt | cggttcataa | atttaaaaat | aattttaaaa tgttatataa | 1380 |
| aactgttttt | taaaaataaa | ttaatcaata | atctaaaacg | ataaaaatgg cgatttgaat | 1440 |
| taagctcata | ttttgaaaaa | aaaataaaaa | ttatctcatc | cagaactgat taaaaccgaa | 1500 |
| ccgatgaatc | ctagaagcca | agccaagtgt | gcagagtaag | aatagaacat caacattttg | 1560 |
| ctttaagctt | ttcgttgctt | gcactctaag | aagcataaaa | cgcaagcaaa acttgacact | 1620 |
| agtgtgagtg | tgagtgccca | tcattcatca | accctgaaaa | tcgcccttcc cctaatcagt | 1680 |
| tctaacctca | cttctaaca | ctttcactgc | agcactcaaa | acattcgcc gaatctttac | 1740 |
| tataaactcc | cagtgttggt | ttctccactc | caaacccaaa | ccacgaccac cacattttgc | 1800 |
| ttcgtatctt | tgata | | | | 1815 |

<210> SEQ ID NO 10
<211> LENGTH: 2105
<212> TYPE: DNA
<213> ORGANISM: Gossypium hirsutum

<400> SEQUENCE: 10

| | | | | | |
|---|---|---|---|---|---|
| atgaaacatc | ttcgtactca | tatctgaaac | tccagcttct | tgatcctcaa tgataattaa | 60 |
| atcctcacta | tcactcgcat | tcacctcgag | cagcttcgca | aattgaaatg tttccttagc | 120 |
| ttccttcact | atacttgcga | ttcccaatga | cagagtcagt | aagggaacca ttaacaatac | 180 |
| gatcatccgt | tctttgcttc | ttcaccagac | accacacctt | tagatatgat tggttttcta | 240 |
| cctctacgtt | tttgcttctt | ttttttttt | aaccaaagtc | atcacttttt cttcaatctc | 300 |
| tgccaatgat | ctcaccttct | tcttcacacc | atcaacagta | attatcgtcg aatagggatt | 360 |
| atgcactaca | gtgttttgca | ttgctactcc | catggagtcc | tccaccctaa ctctacttgt | 420 |
| aggactccta | actaacgaat | tgcaaagggt | ttcgcgaccc | gaattgttcc ctttctgaca | 480 |
| acccaagtcc | acttaggttc | aatcatattt | aaattcgtat | caacaatctc ctcagccgac | 540 |
| caattcacag | ctttcaaatc | tgctccgcaa | cccaccattt | gatcgtgacc aaagtgtgaa | 600 |
| cttgccttca | acaaatcagg | cccagagcct | cgttctaatc | atttctcgag gcaatagcaa | 660 |
| tagttgggtc | taagttctct | gctaattcct | ttgatttcct | agaacctctc gagctgccat | 720 |
| attgggtttt | tcactaccca | cctcttcatt | aaatgtatct | tcaacctctc aactcctttc | 780 |
| accaccagac | gaatcttctt | tagcaaaatc | aaaatgacct | tatgaaaatt tagcacgtcc | 840 |
| acctccagat | tcaaggctg | tgaatcccca | acttcggaaa | ttgttcatct ccacattcaa | 900 |
| gaataatgag | ttcctcaatt | tgttttaact | gattagccga | tattaagcga gttagactcc | 960 |
| atggaaataa | aatcacccta | ataaatagca | acgcttttga | acgtctctag gttccaagcg | 1020 |
| tgctaaggag | cgccagtaac | ttcaatccaa | gttgtgcgaa | aacgtatgaa atggaactga | 1080 |
| gaccagcgtt | caacatcgat | gaaaatttgt | tttaacaatg | agaactgcaa atcctccata | 1140 |
| gtcttctaac | atttcaacat | tcgaaatctc | gaaagaaat | tggcttgata tgatttattt | 1200 |
| agggtgttaa | ttttatgtat | tataataatg | cacaaattga | tattttatgc atcacattta | 1260 |

-continued

```
atatttttaa agtatataat atcaaatcat tttatgaaaa taaaaatacc aaataataca      1320
taaattgata gttcaagtat ttcattaaaa attttcaaaa tataaatatc atattgaaac      1380
attttataaa agaatagata ccaaatatga catcatcccc tgttgagagt aaccaaacac      1440
tgttttcatc cagcccatga gaagtatttg gcccaaaagc aaaagtttca gtacaatgaa      1500
ttatgaatcc caaaaaaacc ccaagtggtc caggtccaag ccagtctagg gctgaggaaa      1560
gaaatggaaa aattgaaaag taattccagg gtctgattca attttattaa atttagtttg      1620
attttggttt cggttcataa atttaaaaat aattttaaaa tgttatataa aactgttttt      1680
taaaaataaa ttaatcaata atctaaaacg ataaaaatgg cgatttgaat taagctcata      1740
ttttgaaaaa aaataaaaa ttatctcatc cagaactgat taaaaccgaa ccgatgaatc      1800
ctagaagcca agccaagtgt gcagagtaag aatagaacat caacattttg ctttaagctt      1860
ttcgttgctt gcactctaag aagcataaaa cgcaagcaaa acttgacact agtgtgagtg      1920
tgagtgccca tcattcatca accctgaaaa tcgcccttcc cctaatcagt tctaacctca      1980 cttttctaaca ctttcactgc agcactcaaa acattcgcc gaatctttac tataaactcc      2040
cagtgttggt ttctccactc caaacccaaa ccacgaccac cacattttgc ttcgtatctt      2100
tgata                                                                 2105
```

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:
      Random 10-mer (W17) from a 10mer kit from Operon Technologies
      (Almeda, CA)

<400> SEQUENCE: 11
gtcctgggtt                                                                10

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 12
caatggctat atgtgactca ttcaatcaca c                                        31

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
cgctctagaa ctagtggatc                                                     20

<210> SEQ ID NO 14
<211> LENGTH: 59
<212> TYPE: PRT
<213> ORGANISM: Arabidopsis thaliana
<220> FEATURE:
<221> NAME/KEY: SIMILAR
<222> LOCATION: (18)
<223> OTHER INFORMATION: X at position 18 is an amino acid that is
      weakly or strongly similar to I

```
<220> FEATURE:
<221> NAME/KEY: SIMILAR
<222> LOCATION: (26)
<223> OTHER INFORMATION: X at position 26 is an amino acid that is
      weakly or strongly similar to E
<220> FEATURE:
<221> NAME/KEY: SIMILAR
<222> LOCATION: (29)
<223> OTHER INFORMATION: X at position 29 is an amino acid that is
      weakly or strongly similar to D
<220> FEATURE:
<221> NAME/KEY: SIMILAR
<222> LOCATION: (37)
<223> OTHER INFORMATION: X at position 37 is an amino acid that is
      weakly or strongly similar to N
<220> FEATURE:
<221> NAME/KEY: SIMILAR
<222> LOCATION: (42)
<223> OTHER INFORMATION: X at position 42 is an amino acid that is
      weakly or strongly similar to I
<220> FEATURE:
<221> NAME/KEY: SIMILAR
<222> LOCATION: (54)
<223> OTHER INFORMATION: X at position 54 is an amino acid that is
      weakly or strongly similar to L

<400> SEQUENCE: 14

Thr Tyr Pro Cys Thr Pro Gly Val Ser Tyr His Gly Arg Gly Ala Leu
  1               5                  10                  15

Pro Xaa Tyr Trp Asn Tyr Asn Tyr Gly Xaa Thr Gly Xaa Ala Leu Lys
             20                  25                  30

Val Asp Leu Leu Xaa His Pro Glu Tyr Xaa Glu Asn Asn Ala Thr Leu
         35                  40                  45

Ala Phe Gln Ala Ala Xaa Trp Arg Trp Met Thr
     50                  55

<210> SEQ ID NO 15
<211> LENGTH: 59
<212> TYPE: PRT
<213> ORGANISM: Arabis microphylla
<220> FEATURE:
<221> NAME/KEY: SIMILAR
<222> LOCATION: (2)
<223> OTHER INFORMATION: X at position 2 is an amino acid that is
      weakly or strongly similar to Y
<220> FEATURE:
<221> NAME/KEY: SIMILAR
<222> LOCATION: (5)
<223> OTHER INFORMATION: X at position 5 is an amino acid that is
      weakly or strongly similar to T
<220> FEATURE:
<221> NAME/KEY: SIMILAR
<222> LOCATION: (11)
<223> OTHER INFORMATION: X at position 11 is an amino acid that
      is weakly or strongly similar to H
<220> FEATURE:
<221> NAME/KEY: SIMILAR
<222> LOCATION: (15)
<223> OTHER INFORMATION: X at position 15 is an amino acid that
      is weakly or strongly similar to A
<220> FEATURE:
<221> NAME/KEY: SIMILAR
<222> LOCATION: (16)
<223> OTHER INFORMATION: X at position 16 is an amino acid that
      is weakly or strongly similar to L
<220> FEATURE:
<221> NAME/KEY: SIMILAR
<222> LOCATION: (18)
<223> OTHER INFORMATION: X at position 18 is an amino acid that
      is weakly or strongly similar to I
```

```
<220> FEATURE:
<221> NAME/KEY: SIMILAR
<222> LOCATION: (31)
<223> OTHER INFORMATION: X at position 31 is an amino acid that
      is weakly or strongly similar to L
<220> FEATURE:
<221> NAME/KEY: SIMILAR
<222> LOCATION: (38)
<223> OTHER INFORMATION: X at position 38 is an amino acid that
      is weakly or strongly similar to H
<220> FEATURE:
<221> NAME/KEY: SIMILAR
<222> LOCATION: (40)
<223> OTHER INFORMATION: X at position 40 is an amino acid that
      is weakly or strongly similar to E
<220> FEATURE:
<221> NAME/KEY: SIMILAR
<222> LOCATION: (42)
<223> OTHER INFORMATION: X at position 42 is an amino acid that
      is weakly or strongly similar to I
<220> FEATURE:
<221> NAME/KEY: SIMILAR
<222> LOCATION: (45)
<223> OTHER INFORMATION: X at position 45 is an amino acid that
      is weakly or strongly similar to N
<220> FEATURE:
<221> NAME/KEY: SIMILAR
<222> LOCATION: (47)
<223> OTHER INFORMATION: X at position 47 is an amino acid that
      is weakly or strongly similar to T
<220> FEATURE:
<221> NAME/KEY: SIMILAR
<222> LOCATION: (48)
<223> OTHER INFORMATION: X at position 48 is an amino acid that
      is weakly or strongly similar to L
<220> FEATURE:
<221> NAME/KEY: SIMILAR
<222> LOCATION: (51)
<223> OTHER INFORMATION: X at position 51 is an amino acid that
      is weakly or strongly similar to Q
<220> FEATURE:
<221> NAME/KEY: SIMILAR
<222> LOCATION: (54)
<223> OTHER INFORMATION: X at position 54 is an amino acid that
      is weakly or strongly similar to L

<400> SEQUENCE: 15

Thr Xaa Pro Cys Xaa Pro Gly Lys Arg Tyr Xaa Gly Arg Gly Xaa Xaa
 1               5                  10                  15

Gln Xaa Ser Trp Asn Tyr Asn Tyr Gly Leu Cys Gly Arg Ala Xaa Gly
             20                  25                  30

Val Asp Leu Leu Asn Xaa Pro Xaa Leu Xaa Ala Asn Xaa Ala Xaa Xaa
         35                  40                  45

Ala Phe Xaa Ala Ala Xaa Trp Phe Trp Met Thr
     50                  55

<210> SEQ ID NO 16
<211> LENGTH: 59
<212> TYPE: PRT
<213> ORGANISM: Gossypium hirsutum
<220> FEATURE:
<221> NAME/KEY: SIMILAR
<222> LOCATION: (1)
<223> OTHER INFORMATION: X at position 1 is an amino acid that is
      weakly or strongly similar to T
<220> FEATURE:
<221> NAME/KEY: SIMILAR
<222> LOCATION: (5)
<223> OTHER INFORMATION: X at position 5 is an amino acid that is
      weakly or strongly similar to T
```

-continued

```
<220> FEATURE:
<221> NAME/KEY: SIMILAR
<222> LOCATION: (9)
<223> OTHER INFORMATION: X at position 9 is an amino acid that is
      weakly or strongly similar to S
<220> FEATURE:
<221> NAME/KEY: SIMILAR
<222> LOCATION: (11)
<223> OTHER INFORMATION: X at position 11 is an amino acid that
      is weakly or strongly similar to H
<220> FEATURE:
<221> NAME/KEY: SIMILAR
<222> LOCATION: (15)
<223> OTHER INFORMATION: X at position 15 is an amino acid that
      is weakly or strongly similar to A
<220> FEATURE:
<221> NAME/KEY: SIMILAR
<222> LOCATION: (16)
<223> OTHER INFORMATION: X at position 16 is an amino acid that
      is weakly or strongly similar to L
<220> FEATURE:
<221> NAME/KEY: SIMILAR
<222> LOCATION: (18)
<223> OTHER INFORMATION: X at position 18 is an amino acid that
      is weakly or strongly similar to I
<220> FEATURE:
<221> NAME/KEY: SIMILAR
<222> LOCATION: (26)
<223> OTHER INFORMATION: X at position 26 is an amino acid that
      is weakly or strongly similar to E
<220> FEATURE:
<221> NAME/KEY: SIMILAR
<222> LOCATION: (31)
<223> OTHER INFORMATION: X at position 31 is an amino acid that
      is weakly or strongly similar to L
<220> FEATURE:
<221> NAME/KEY: SIMILAR
<222> LOCATION: (32)
<223> OTHER INFORMATION: X at position 32 is an amino acid that
      is weakly or strongly similar to K
<220> FEATURE:
<221> NAME/KEY: SIMILAR
<222> LOCATION: (38)
<223> OTHER INFORMATION: X at position 38 is an amino acid that
      is weakly or strongly similar to H
<220> FEATURE:
<221> NAME/KEY: SIMILAR
<222> LOCATION: (40)
<223> OTHER INFORMATION: X at position 40 is an amino acid that
      is weakly or strongly similar to E
<220> FEATURE:
<221> NAME/KEY: SIMILAR
<222> LOCATION: (42)
<223> OTHER INFORMATION: X at position 42 is an amino acid that
      is weakly or strongly similar to I
<220> FEATURE:
<221> NAME/KEY: SIMILAR
<222> LOCATION: (43)
<223> OTHER INFORMATION: X at position 43 is an amino acid that
      is weakly or strongly similar to E
<220> FEATURE:
<221> NAME/KEY: SIMILAR
<222> LOCATION: (44)..(45)
<223> OTHER INFORMATION: X at positions 44 and 45 is an amino acid
      that is weakly or strongly similar to N
<220> FEATURE:
<221> NAME/KEY: SIMILAR
<222> LOCATION: (46)
<223> OTHER INFORMATION: X at position 46 is an amino acid that
      is weakly or strongly similar to A
<220> FEATURE:
<221> NAME/KEY: SIMILAR
<222> LOCATION: (48)
<223> OTHER INFORMATION: X at position 48 is an amino acid that
      is weakly or strongly similar to L
```

```
<220> FEATURE:
<221> NAME/KEY: SIMILAR
<222> LOCATION: (49)
<223> OTHER INFORMATION: X at position 49 is an amino acid that
      is weakly or strongly similar to A
<220> FEATURE:
<221> NAME/KEY: SIMILAR
<222> LOCATION: (51)
<223> OTHER INFORMATION: X at position 51 is an amino acid that
      is weakly or strongly similar to Q
<220> FEATURE:
<221> NAME/KEY: SIMILAR
<222> LOCATION: (52)
<223> OTHER INFORMATION: X at position 52 is an amino acid that
      is weakly or strongly similar to A
<220> FEATURE:
<221> NAME/KEY: SIMILAR
<222> LOCATION: (54)
<223> OTHER INFORMATION: X at position 54 is an amino acid that
      is weakly or strongly similar to L
<220> FEATURE:

<400> SEQUENCE: 16

Xaa Tyr Pro Cys Xaa Pro Gly Lys Xaa Tyr Xaa Gly Arg Gly Xaa Xaa
 1               5                  10                  15

Gln Xaa Ser Trp Asn Tyr Asn Tyr Gly Xaa Cys Gly Arg Ala Xaa Xaa
            20                  25                  30

Val Asp Leu Leu Asn Xaa Pro Xaa Leu Xaa Xaa Xaa Xaa Xaa Thr Xaa
        35                  40                  45

Xaa Phe Xaa Xaa Ala Xaa Trp Phe Trp Met Thr
    50                  55

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 17

Gly Arg Gly Pro Ile Gln Leu Ser Trp Asn Tyr Asn Tyr Gly Pro Ala
 1               5                  10                  15

Gly Arg Ala Ile
            20

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Signature
      sequence of putatively unchanging amino acids

<400> SEQUENCE: 18

Lys Arg Glu Val Ala Ala Phe Leu Ala Gln Thr Ser His Glu Thr Thr
 1               5                  10                  15

Gly Gly Trp Ala Thr Ala Pro Asp Gly Ala Phe Ala Trp Gly Tyr Cys
            20                  25                  30

Phe Lys Gln Glu Arg Gly Ala
            35

<210> SEQ ID NO 19
<211> LENGTH: 39
<212> TYPE: PRT
<213> ORGANISM: Arabis microphylla
```

```
<400> SEQUENCE: 19

Lys Lys Glu Ile Ala Ala Phe Phe Gly Gln Thr Ser His Glu Thr Thr
  1               5                  10                  15

Gly Gly Trp Ala Ser Ala Pro Asp Gly Pro Phe Ser Trp Gly Tyr Cys
             20                  25                  30

Phe Lys Gln Glu Gln Asn Pro
         35

<210> SEQ ID NO 20
<211> LENGTH: 39
<212> TYPE: PRT
<213> ORGANISM: Arabidopsis thaliana

<400> SEQUENCE: 20

Met Lys Glu Val Ala Ala Phe Leu Gly His Val Gly Ser Lys Thr Ser
  1               5                  10                  15

Cys Gly Tyr Gly Val Ala Thr Gly Gly Pro Leu Ala Trp Gly Leu Cys
             20                  25                  30

Tyr Asn Lys Glu Met Ser Pro
         35

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 21
gctgagtcga cgatatcgaa ttcctgcagc c                            31

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
gctgagtcga ccttcaatct ctgccaatga tc                           32

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 23
gctgagtcga caacctctcg agctgccata t                            31

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 24
gctgagtcga cctgagacca gcgttcaaca t                            31
```

```
<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:  Primer

<400> SEQUENCE: 25
gctagtctag atatcaaaga tacgaagcaa aatg                              34

<210> SEQ ID NO 26
<211> LENGTH: 39
<212> TYPE: PRT
<213> ORGANISM: Arabidopsis thaliana

<400> SEQUENCE: 26

Gln Lys Glu Met Ala Ala Phe Leu Gly His Val Ala Ser Lys Thr Ser
 1               5                  10                  15

Cys Gly Tyr Gly Val Ala Thr Gly Gly Pro Leu Ala Trp Gly Leu Cys
            20                  25                  30

Tyr Asn Arg Glu Met Ser Pro
        35

<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence:  Consensus
      sequence

<400> SEQUENCE: 27

Lys Glu Ala Ala Phe Leu Gly His Val Ser Lys Thr Ser Cys Gly Tyr
 1               5                  10                  15

Gly Val Ala Thr Gly Gly Pro Leu Ala Trp Gly Leu Cys Tyr Asn Glu
            20                  25                  30

Met Ser Pro
        35

<210> SEQ ID NO 28
<211> LENGTH: 20
<212> TYPE: PRT
<213> ORGANISM: Arabidopsis thaliana

<400> SEQUENCE: 28

Gly Arg Gly Ala Leu Pro Ile Tyr Trp Asn Phe Asn Tyr Gly Ala Ala
 1               5                  10                  15

Gly Glu Ala Leu
            20

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:  Consensus
      sequence

<400> SEQUENCE: 29

Gly Arg Gly Ala Leu Pro Tyr Trp Asn Asn Tyr Gly Gly Ala Leu
 1               5                  10                  15
```

```
<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence:  Consensus
      sequence

<400> SEQUENCE: 30 caannnnatc                                                          10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence:  Consensus
      sequence

<400> SEQUENCE: 31 ttwtwttwtt                                                          10

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence:  Consensus
      sequence

<400> SEQUENCE: 32
wtttatrttt w                                                        11
```